US008030043B2

(12) United States Patent
Yamamoto et al.

(10) Patent No.: US 8,030,043 B2
(45) Date of Patent: Oct. 4, 2011

(54) β-GALACTOSIDE-α2,3-SIALYLTRANSFERASE, A GENE ENCODING THEREOF, AND A METHOD FOR PRODUCING THEREOF

(75) Inventors: Takeshi Yamamoto, Iwata (JP); Hiroshi Tsukamoto, Iwata (JP); Yoshimitsu Takakura, Iwata (JP)

(73) Assignee: Japan Tobacco Inc., Tokyo (JP)

( * ) Notice: Subject to any disclaimer, the term of this patent is extended or adjusted under 35 U.S.C. 154(b) by 517 days.

(21) Appl. No.: 11/918,328

(22) PCT Filed: Mar. 31, 2006

(86) PCT No.: PCT/JP2006/306896
§ 371 (c)(1),
(2), (4) Date: Dec. 23, 2008

(87) PCT Pub. No.: WO2006/112253
PCT Pub. Date: Oct. 26, 2006

(65) Prior Publication Data
US 2010/0291631 A1    Nov. 18, 2010

(30) Foreign Application Priority Data

Apr. 15, 2005  (WO) .................. PCT/JP2005/007340
Jun. 13, 2005  (WO) .................. PCT/JP2005/010814

(51) Int. Cl.
| C12N 9/10 | (2006.01) |
| C12N 9/00 | (2006.01) |
| C12N 15/00 | (2006.01) |
| C12N 1/20 | (2006.01) |
| C12P 21/06 | (2006.01) |
| C12P 19/34 | (2006.01) |
| C12P 19/44 | (2006.01) |
| C07H 21/04 | (2006.01) |

(52) U.S. Cl. ...... 435/193; 435/183; 435/69.1; 435/91.1; 435/320.1; 435/252.1; 435/252.3; 435/74; 536/23.2; 536/23.1; 536/23.7

(58) Field of Classification Search .................. 435/193, 435/183, 69.1, 91.1, 320.1, 252.1, 252.3, 435/74; 536/23.2, 23.1, 23.7
See application file for complete search history.

(56) References Cited

FOREIGN PATENT DOCUMENTS

| EP | 0915153 A1 | 5/1999 |
| EP | 0915163 A1 | 5/1999 |
| EP | 0 906 432 B1 | 6/2004 |
| JP | 10-234373 A | 9/1998 |
| JP | 2001-503961 A | 3/2001 |
| WO | WO-97/47749 A1 | 12/1997 |
| WO | WO-99/49051 A1 | 9/1999 |
| WO | WO-01/77314 A1 | 10/2001 |
| WO | WO-03/027297 A1 | 4/2003 |

OTHER PUBLICATIONS

Broun et al., Catalytic plasticity of fatty acid modification enzymes underlying chemical diversity of plant lipids. Science, 1998, vol. 282: 1315-1317.*
Chica et al., Semi-rational approaches to engineering enzyme activity: combining the benefits of directed evolution and rational design. Curr. Opi. Biotechnol., 2005, vol. 16: 378-384.*
Devos et al., Practical limits of function prediction. Proteins: Structure, Function, and Genetics. 2000, vol. 41: 98-107.*
Guo et al., Protein tolerance to random amino acid change. PNAS., 2004, vol. 101 (25): 9205-9210.*
Seffernick et al., Melamine deaminase and Atrazine chlorohydrolase: 98 percent identical but functionally different. J. Bacteriol.,2001, vol. 183 (8): 2405-2410.*
Sen et al., Developments in directed evolution for improving enzyme functions. Appl. Biochem. Biotechnol., 2007, vol. 143: 212-223.*
Wishart et al., A single mutation converts a novel phosphotyrosine binding domain into a dual-specificity phosphatase. J. Biol. Chem., 1995, vol. 270(45): 26782-26785.*
Whisstock et al., Prediction of protein function from protein sequence. Q. Rev. Biophysics., 2003, vol. 36 (3): 307-340.*
Witkowski et al., Conversion of b-ketoacyl synthase to a Malonyl Decarboxylase by replacement of the active cysteine with glutamine. Biochemistry, 1999, vol. 38: 11643-11650.*
Cameron ER., Recent advances in transgenic technology. 1997, vol. 7: 253-265.*
Kappel et al., Regulating gene expression in transgenic animals. Current Opinion in Biotechnology 1992, vol. 3: 548-553.*
Mullins et al., Transgenesis in nonmurine species. Hypertension, 1993, vol. 22 (4): 630-633.*
Mullins et al., Transgenesis in the rat and larger mammals. J. Clin. Invest., 1996, vol. 97 (7): 1557-1560.*
Wigley et al., Site-specific transgene insertion: an approach. Reprod. Fert. Dev., 1994, vol. 6: 585-588.*
Tsukamoto et al., Purification, cloning, and expression of an a/b-Galactoside a-2,3-sialyltransferase from a luminous marine bacterium, *Photobacterium phosphoreum*. J. Biol. Chem., 2007, vol. 282 (41): 29794-29802.*
Takakura Y et al., "Molecular Cloning and Production of a Beta-Galactoside Alpha 2,3-Sialyltransferase of Vibrio sp. JT-FAJ-16", Glycobiology, vol. 15, No. 11, p. 1206, 2005, Oxford University Press. XP008109319.

(Continued)

*Primary Examiner* — Ganapathirama Raghu
(74) *Attorney, Agent, or Firm* — Birch, Stewart, Kolasch & Birch, LLP

(57) ABSTRACT

The present invention provides a novel β-galactoside-α2,3-sialyltransferase and a nucleic acid encoding the sialyltransferase. The present invention also provides a microorganism producing the sialyltransferase, as well as a method for producing the sialyltransferase using such a microorganism. The present invention further provides a vector carrying a nucleic acid encoding the sialyltransferase, and a host cell transformed with the vector, as well as a method for producing a recombinant β-galactoside-α2,3-sialyltransferase. The present invention further provides a method for preparing a sialylsugar chain, which uses the sialyltransferase of the present invention.

19 Claims, 7 Drawing Sheets

OTHER PUBLICATIONS

Tsukamoto Hiroshi et al., "Purification, cloning, and expression of an alpha/beta-galactoside alpha-2,3-sialyltransferase from a luminous bacterium, *Photobacterium phosphoreum*" Journal of Biological Chemistry, vol. 282, No. 41, pp. 29794-29802, 2007. XP002540676.

Takakura Yoshimitsu et al., "Molecular Cloning, Expression and Properties of an alpha/beta-galactoside alpha 2, 3-sialyltransferase from Vibrio sp. JT-FAJ-16" Journal of Biochemistry, vol. 142, No. 3, pp. 403-412, 2007. XP002540661.

Tsukamoto Hiroshi et al., "*Photobacterium* sp JT-ISH-224 produces two sialyltransferase, alpha-/beta-galactoside alpha 2,3-sialyltransferase", Journal of Biochemistry, vol. 143, No. 2, pp. 187-197, 2008. XP002540660.

Harduin-Lepers et al., Biochem. J., vol. 352, pp. 37-48 (2000).

Lee et al., The Journal of Biological Chemistry, vol. 274, No. 17, pp. 11958-11967 (1999).

Lee et al., Eur. J. Biochem., vol. 216, pp. 377-385 (1993).

Chang et al., Glycobiology, vol. 5, No. 3, pp. 319-325 (1995).

Gillespie et al., J. Biol. Chem., vol. 267, No. 29, pp. 21004-21010 (1992).

* cited by examiner

Figure 2

SEQUENCE LISTING

<160> NUMBER OF SEQ ID NOS: 47

<210> SEQ ID NO 1
<211> LENGTH: 1230
<212> TYPE: DNA
<213> ORGANISM: Photobacterium phosphoreum
<220> FEATURE:
<221> NAME/KEY: CDS
<222> LOCATION: (1)..(1230)
<223> OTHER INFORMATION: /gene="467-23ST" /product="Beta-galactoside-alpha 2,3-sialyltransferase"

-continued

```
<400> SEQUENCE: 1 atg ttc gtt ttt tgt aaa aaa ata ttt ttt ttg att ttt att tca cta      48
Met Phe Val Phe Cys Lys Lys Ile Phe Phe Leu Ile Phe Ile Ser Leu
1               5                   10                  15 atg att ctg ggg ggc tgt aat agt gac tct aag cac aat aac tca gat      96
Met Ile Leu Gly Gly Cys Asn Ser Asp Ser Lys His Asn Asn Ser Asp
            20                  25                  30 ggt aat att aca aaa aat aaa aca ata gaa gtt tat gtt gat aga gca     144
Gly Asn Ile Thr Lys Asn Lys Thr Ile Glu Val Tyr Val Asp Arg Ala
        35                  40                  45 aca tta cca act att caa caa atg act cag att att aat gaa aat tca     192
Thr Leu Pro Thr Ile Gln Gln Met Thr Gln Ile Ile Asn Glu Asn Ser
    50                  55                  60 aat aat aag aaa ctt att tct tgg tct cga tac cct att aat gat gaa     240
Asn Asn Lys Lys Leu Ile Ser Trp Ser Arg Tyr Pro Ile Asn Asp Glu
65                  70                  75                  80 acg tta tta gaa tca att aat gga tca ttt ttt aaa aat agg cca gag     288
Thr Leu Leu Glu Ser Ile Asn Gly Ser Phe Phe Lys Asn Arg Pro Glu
                85                  90                  95 cta att aaa tct ctt gat tct atg ata ctt act aat gag att aaa aaa     336
Leu Ile Lys Ser Leu Asp Ser Met Ile Leu Thr Asn Glu Ile Lys Lys
            100                 105                 110 gta atc att aat ggt aat acc tta tgg gca gta gat gtc gtt aat att     384
Val Ile Ile Asn Gly Asn Thr Leu Trp Ala Val Asp Val Val Asn Ile
        115                 120                 125 ata aaa tca att gaa gct ctt gga aaa aaa aca gag att gaa cta aat     432
Ile Lys Ser Ile Glu Ala Leu Gly Lys Lys Thr Glu Ile Glu Leu Asn
    130                 135                 140 ttt tat gat gac ggt agt gca gaa tat gtt cga tta tat gac ttt tca     480
Phe Tyr Asp Asp Gly Ser Ala Glu Tyr Val Arg Leu Tyr Asp Phe Ser
145                 150                 155                 160 aga tta cct gaa tca gaa caa gaa tat aaa ata tcc tta tca aag gat     528
Arg Leu Pro Glu Ser Glu Gln Glu Tyr Lys Ile Ser Leu Ser Lys Asp
                165                 170                 175 aac att caa tca agt ata aat gga act caa cca ttt gat aac tca att     576
Asn Ile Gln Ser Ser Ile Asn Gly Thr Gln Pro Phe Asp Asn Ser Ile
            180                 185                 190 gaa aat atc tat ggc ttt tcg cag tta tac cca aca aca tat cat atg     624
Glu Asn Ile Tyr Gly Phe Ser Gln Leu Tyr Pro Thr Thr Tyr His Met
        195                 200                 205 ctc aga gca gat att ttt gaa act aat tta cct ttg acc tct ttg aaa     672
Leu Arg Ala Asp Ile Phe Glu Thr Asn Leu Pro Leu Thr Ser Leu Lys
    210                 215                 220 aga gta ata tca aat aat att aag caa atg aaa tgg gat tat ttt aca     720
Arg Val Ile Ser Asn Asn Ile Lys Gln Met Lys Trp Asp Tyr Phe Thr
225                 230                 235                 240 act ttt aat tcc caa cag aag aat aaa ttc tat aat ttc acg gga ttt     768
Thr Phe Asn Ser Gln Gln Lys Asn Lys Phe Tyr Asn Phe Thr Gly Phe
                245                 250                 255 aac cca gaa aaa att aag gaa caa tat aaa gca agc cct cat gaa aat     816
Asn Pro Glu Lys Ile Lys Glu Gln Tyr Lys Ala Ser Pro His Glu Asn
            260                 265                 270 ttt att ttt atc gga act aat tca gga aca gca acg gca gag caa caa     864
Phe Ile Phe Ile Gly Thr Asn Ser Gly Thr Ala Thr Ala Glu Gln Gln
        275                 280                 285 ata gat att ctt aca gaa gct aaa aag cca gat agc ccg ata ata act     912
Ile Asp Ile Leu Thr Glu Ala Lys Lys Pro Asp Ser Pro Ile Ile Thr
    290                 295                 300 aat tca att caa gga ttg gat ttg ttt ttc aaa gga cat ccg agt gca     960
```

```
Asn Ser Ile Gln Gly Leu Asp Leu Phe Phe Lys Gly His Pro Ser Ala
305                 310                 315                 320 act tat aat caa caa atc att gat gct cat aat atg att gaa att tat      1008
Thr Tyr Asn Gln Gln Ile Ile Asp Ala His Asn Met Ile Glu Ile Tyr
                325                 330                 335 aat aag ata cca ttt gaa gct cta ata atg act gat gca ttg cct gat      1056
Asn Lys Ile Pro Phe Glu Ala Leu Ile Met Thr Asp Ala Leu Pro Asp
            340                 345                 350 gct gtc ggt gga atg gga agt tcg gta ttt ttt agc ttg cca aat aca      1104
Ala Val Gly Gly Met Gly Ser Ser Val Phe Phe Ser Leu Pro Asn Thr
        355                 360                 365 gta gag aat aaa ttt att ttt tat aaa agt gat acg gat att gaa aat      1152
Val Glu Asn Lys Phe Ile Phe Tyr Lys Ser Asp Thr Asp Ile Glu Asn
    370                 375                 380 aat gct ctt ata caa gta atg att gaa ctg aat atc gtt aat aga aat      1200
Asn Ala Leu Ile Gln Val Met Ile Glu Leu Asn Ile Val Asn Arg Asn
385                 390                 395                 400 gat gtt aag ttg ata agt gat ttg cag taa                              1230
Asp Val Lys Leu Ile Ser Asp Leu Gln
                405
```

<210> SEQ ID NO 2
<211> LENGTH: 409
<212> TYPE: PRT
<213> ORGANISM: Photobacterium phosphoreum

<400> SEQUENCE: 2

```
Met Phe Val Phe Cys Lys Lys Ile Phe Phe Leu Ile Phe Ile Ser Leu
1               5                   10                  15

Met Ile Leu Gly Gly Cys Asn Ser Asp Ser Lys His Asn Asn Ser Asp
            20                  25                  30

Gly Asn Ile Thr Lys Asn Lys Thr Ile Glu Val Tyr Val Asp Arg Ala
        35                  40                  45

Thr Leu Pro Thr Ile Gln Gln Met Thr Gln Ile Ile Asn Glu Asn Ser
    50                  55                  60

Asn Asn Lys Lys Leu Ile Ser Trp Ser Arg Tyr Pro Ile Asn Asp Glu
65                  70                  75                  80

Thr Leu Leu Glu Ser Ile Asn Gly Ser Phe Phe Lys Asn Arg Pro Glu
                85                  90                  95

Leu Ile Lys Ser Leu Asp Ser Met Ile Leu Thr Asn Glu Ile Lys Lys
            100                 105                 110

Val Ile Ile Asn Gly Asn Thr Leu Trp Ala Val Asp Val Asn Ile
        115                 120                 125

Ile Lys Ser Ile Glu Ala Leu Gly Lys Lys Thr Glu Ile Glu Leu Asn
    130                 135                 140

Phe Tyr Asp Asp Gly Ser Ala Glu Tyr Val Arg Leu Tyr Asp Phe Ser
145                 150                 155                 160

Arg Leu Pro Glu Ser Gln Glu Tyr Lys Ile Ser Leu Ser Lys Asp
                165                 170                 175

Asn Ile Gln Ser Ser Ile Asn Gly Thr Gln Pro Phe Asp Asn Ser Ile
            180                 185                 190

Glu Asn Ile Tyr Gly Phe Ser Gln Leu Tyr Pro Thr Tyr His Met
        195                 200                 205

Leu Arg Ala Asp Ile Phe Glu Thr Asn Leu Pro Leu Thr Ser Leu Lys
    210                 215                 220

Arg Val Ile Ser Asn Asn Ile Lys Gln Met Lys Trp Asp Tyr Phe Thr
225                 230                 235                 240
```

```
Thr Phe Asn Ser Gln Gln Lys Asn Lys Phe Tyr Asn Phe Thr Gly Phe
                245                 250                 255

Asn Pro Glu Lys Ile Lys Glu Gln Tyr Lys Ala Ser Pro His Glu Asn
            260                 265                 270

Phe Ile Phe Ile Gly Thr Asn Ser Gly Thr Ala Thr Ala Glu Gln Gln
        275                 280                 285

Ile Asp Ile Leu Thr Glu Ala Lys Lys Pro Asp Ser Pro Ile Ile Thr
    290                 295                 300

Asn Ser Ile Gln Gly Leu Asp Leu Phe Phe Lys Gly His Pro Ser Ala
305                 310                 315                 320

Thr Tyr Asn Gln Gln Ile Ile Asp Ala His Asn Met Ile Glu Ile Tyr
                325                 330                 335

Asn Lys Ile Pro Phe Glu Ala Leu Ile Met Thr Asp Ala Leu Pro Asp
            340                 345                 350

Ala Val Gly Gly Met Gly Ser Ser Val Phe Phe Ser Leu Pro Asn Thr
        355                 360                 365

Val Glu Asn Lys Phe Ile Phe Tyr Lys Ser Asp Thr Asp Ile Glu Asn
    370                 375                 380

Asn Ala Leu Ile Gln Val Met Ile Glu Leu Asn Ile Val Asn Arg Asn
385                 390                 395                 400

Asp Val Lys Leu Ile Ser Asp Leu Gln
                405

<210> SEQ ID NO 3
<211> LENGTH: 1397
<212> TYPE: DNA
<213> ORGANISM: Photobacterium phosphoreum

<400> SEQUENCE: 3
gctgacgagc ggcggacggg tgagtaatgc ctgggaatat accctgatgt ggggggataac    60
tattggaaac gatagctaat accgcataat ctcttcggag caaagagggg gaccttcggg   120
cctctcgcgt caggattagc ccaggtggga ttagctagtt ggtggggtaa tggctcacca   180
aggcgacgat ccctagctgg tctgagagga tgatcagcca cactggaact gagacacggt   240
ccagactcct acgggaggca gcagtgggga atattgcaca atgggggaaa ccctgatgca   300
gccatgccgc gtgtatgaag aaggccttcg ggttgtaaag tactttcagt tgtgaggaag   360
gcgttggagt taatagcttc agcgcttgac gttagcaaca gaagaagcac cggctaactc   420
cgtgccagca gccgcggtaa tacgagggt gcgagcgtta tcggaatta ctgggcgtaa   480
agcgcatgca ggcggtctgt taagcaagat gtgaaagccc ggggctcaac ctcggaacag   540
cattttgaac tggcagacta gagtcttgta gaggggggta gaatttcagg tgtagcggtg   600
aaatgcgtag agatctgaag gaataccggt ggcgaaggcg gcccctgga caaagactga   660
cgctcagatg cgaaagcgtg gggagcaaac aggattagat accctggtag tccacgccgt   720
aaacgatgtc tacttgaagg ttgtggcctt gagccgtggc tttcggagct aacgcgttaa   780
gtagaccgcc tggggagtac ggtcgcaaga ttaaaactca atgaattga cgggggcccg   840
cacaagcggt ggagcatgtg gtttaattcg atgcaacgcg aagaacctta cctactcttg   900
acatccagag aattcgctag agatagctta gtgccttcgg gaactctgag acaggtgctg   960
catggctgtc gtcagctcgt gttgtgaaat gttgggttaa gtcccgcaac gagcgcaacc  1020
cttatccttg tttgccagca cgtaatggtg gaactccag ggagactgcc ggtgataaac  1080
cggaggaagg tggggacgac gtcaagtcat catggccctt acgagtaggg ctacacacgt  1140
gctacaatgg cgtatacaga gggctgcaag ctagcgatag tgagcgaatc ccacaaagta  1200
```

```
cgtcgtagtc cggattggag tctgcaactc gactccatga agtcggaatc gctagtaatc   1260
gtgaatcaga atgtcacggt gaatacgttc ccgggccttg tacacaccgc ccgtcacacc   1320
atgggagtgg gctgcaccag aagtagatag cttaaccttc gggagggcgt ttaccacggt   1380
gtggttcatg actgggg                                                  1397

<210> SEQ ID NO 4
<211> LENGTH: 10
<212> TYPE: PRT
<213> ORGANISM: Photobacterium phosphoreum
<220> FEATURE:
<221> NAME/KEY: MISC_FEATURE
<222> LOCATION: (1)..(1)
<223> OTHER INFORMATION: Xaa refers to any amino acid

<400> SEQUENCE: 4

Xaa Asn Ser Asp Ser Lys His Asn Asn Ser
1               5                   10

<210> SEQ ID NO 5
<211> LENGTH: 12
<212> TYPE: PRT
<213> ORGANISM: Photobacterium phosphoreum

<400> SEQUENCE: 5

Ser Leu Asp Ser Met Ile Leu Thr Asn Glu Ile Lys
1               5                   10

<210> SEQ ID NO 6
<211> LENGTH: 10
<212> TYPE: PRT
<213> ORGANISM: Photobacterium phosphoreum

<400> SEQUENCE: 6

Phe Tyr Asn Phe Thr Gly Phe Asn Pro Glu
1               5                   10

<210> SEQ ID NO 7
<211> LENGTH: 21
<212> TYPE: PRT
<213> ORGANISM: Photobacterium phosphoreum

<400> SEQUENCE: 7

Gly His Pro Ser Ala Thr Tyr Asn Gln Gln Ile Ile Asp Ala His Asn
1               5                   10                  15

Met Ile Glu Ile Tyr
            20

<210> SEQ ID NO 8
<211> LENGTH: 23
<212> TYPE: DNA
<213> ORGANISM: Artificial Sequence
<220> FEATURE:
<223> OTHER INFORMATION: Synthetic primer: 467N-RV
<220> FEATURE:
<221> NAME/KEY: misc_feature
<222> LOCATION: (6)..(6)
<223> OTHER INFORMATION: n at position 6 is inosine
<220> FEATURE:
<221> NAME/KEY: misc_feature
<222> LOCATION: (12)..(12)
<223> OTHER INFORMATION: n at position 12 is inosine

<400> SEQUENCE: 8
aaywsngayw snaarcayaa yaa                                              23
```

```
<210> SEQ ID NO 9
<211> LENGTH: 20
<212> TYPE: DNA
<213> ORGANISM: Artificial Sequence
<220> FEATURE:
<223> OTHER INFORMATION: Synthetic primer: 467N-RV2
<220> FEATURE:
<221> NAME/KEY: misc_feature
<222> LOCATION: (6)..(6)
<223> OTHER INFORMATION: n at position 6 refers to inosine

<400> SEQUENCE: 9
gaywsnaarc ayaayaayws                                              20

<210> SEQ ID NO 10
<211> LENGTH: 23
<212> TYPE: DNA
<213> ORGANISM: Artificial Sequence
<220> FEATURE:
<223> OTHER INFORMATION: Synthetic primer: 467N-RV3
<220> FEATURE:
<221> NAME/KEY: misc_feature
<222> LOCATION: (6)..(6)
<223> OTHER INFORMATION: n at position 6 refers to any nucleobase
<220> FEATURE:
<221> NAME/KEY: misc_feature
<222> LOCATION: (12)..(12)
<223> OTHER INFORMATION: n at position 6 refers to inosine

<400> SEQUENCE: 10
aaywsngayw snaarcayaa yaa                                          23

<210> SEQ ID NO 11
<211> LENGTH: 21
<212> TYPE: DNA
<213> ORGANISM: Artificial Sequence
<220> FEATURE:
<223> OTHER INFORMATION: Synthetic primer: 467in1RV
<220> FEATURE:
<221> NAME/KEY: misc_feature
<222> LOCATION: (12)..(12)
<223> OTHER INFORMATION: n at position 12 refers to any nucleobase

<400> SEQUENCE: 11
athathgayg cncayaayat g                                            21

<210> SEQ ID NO 12
<211> LENGTH: 21
<212> TYPE: DNA
<213> ORGANISM: Artificial Sequence
<220> FEATURE:
<223> OTHER INFORMATION: Synthetic primer: 467in1FW
<220> FEATURE:
<221> NAME/KEY: misc_feature
<222> LOCATION: (10)..(10)
<223> OTHER INFORMATION: n at position 10 refers to any nucleobase

<400> SEQUENCE: 12
catrttrtgn gcrtcdatda t                                            21

<210> SEQ ID NO 13
<211> LENGTH: 23
<212> TYPE: DNA
<213> ORGANISM: Artificial Sequence
<220> FEATURE:
<223> OTHER INFORMATION: Synthetic primer: 467in1RV2

<400> SEQUENCE: 13
tayaaycarc arathathga ygc                                          23
```

```
<210> SEQ ID NO 14
<211> LENGTH: 23
<212> TYPE: DNA
<213> ORGANISM: Artificial Sequence
<220> FEATURE:
<223> OTHER INFORMATION: Synthetic primer: 467in1FW2

<400> SEQUENCE: 14
gcrtcdatda tytgytgrtt rta                                              23

<210> SEQ ID NO 15
<211> LENGTH: 23
<212> TYPE: DNA
<213> ORGANISM: Artificial Sequence
<220> FEATURE:
<223> OTHER INFORMATION: Synthetic primer: 467in2RV
<220> FEATURE:
<221> NAME/KEY: misc_feature
<222> LOCATION: (12)..(12)
<223> OTHER INFORMATION: n at position 12 refers to any nucleobase
<220> FEATURE:
<221> NAME/KEY: misc_feature
<222> LOCATION: (15)..(15)
<223> OTHER INFORMATION: n at position 15 refers to any nucleobase

<400> SEQUENCE: 15
tayaayttya cnggnttyaa ycc                                              23

<210> SEQ ID NO 16
<211> LENGTH: 23
<212> TYPE: DNA
<213> ORGANISM: Artificial Sequence
<220> FEATURE:
<223> OTHER INFORMATION: Synthetic primer: 467in2FW
<220> FEATURE:
<221> NAME/KEY: misc_feature
<222> LOCATION: (9)..(9)
<223> OTHER INFORMATION: n at position 9 refers to any nucleobase
<220> FEATURE:
<221> NAME/KEY: misc_feature
<222> LOCATION: (12)..(12)
<223> OTHER INFORMATION: n at position 12 refers to any nucleobase

<400> SEQUENCE: 16
ggrttraanc cngtraartt rta                                              23

<210> SEQ ID NO 17
<211> LENGTH: 929
<212> TYPE: DNA
<213> ORGANISM: Photobacterium phosphoreum
<220> FEATURE:
<221> NAME/KEY: misc_feature
<222> LOCATION: (39)..(39)
<223> OTHER INFORMATION: n at position 39 refers to any nucleobase

<400> SEQUENCE: 17
aactggactg gaagcattat aactcagatg gtaatattnc aaaaaataaa ccaatagaag       60
tttatgttga tagagcaaca ttaccaacta ttcaacaaat gactcagatt attaatgaaa      120
attcaaataa taagaaactt atttcttggt ctcgataccc tattaatgat gaaacgttat      180
tagaatcaat taatggatca ttttttaaaa ataggccaga gctaattaaa tctcttgatt      240
ctatgatact tactaatgag attaaaaaag taatcattaa tggtaatacc ttatgggcag      300
tagatgtcgt taatattata aaatcaattg aagctcttgg aaaaaaaaca gagattgaac      360
taaattttta tgatgacggt agtgcagaat atgttcgatt atatgacttt tcaagattac      420
ctgaatcaga acaagaatat aaaatatcct tatcaaagga taacattcaa tcaagtataa      480
```

```
atggaactca accatttgat aactcaattg aaaatatcta tggcttttcg cagttatacc      540
caacaacata tcatatgctc agagcagata tttttgaaac taatttacct ttgacctctt      600
tgaaaagagt aatatcaaat aatattaagc aaatgaaatg ggattatttt acaacttttta    660 attcccaaca gaagaataaa ttctataatt tcacgggatt taacccagaa aaaattaagg     720
aacaatataa agcaagccct catgaaaatt ttattttttat cggaactaat tcaggaacag    780
caacggcaga gcaacaaata gatattctta cagaagctaa aaagccagat agcccgataa     840
taactaattc aattcaagga ttggatttgt ttttcaaagg acatccgagt gcaacttata    900
atcaacaaat catcgacgcg cacaacatg                                       929
```

<210> SEQ ID NO 18
<211> LENGTH: 21
<212> TYPE: DNA
<213> ORGANISM: Artificial Sequence
<220> FEATURE:
<223> OTHER INFORMATION: Synthetic primer: 467-23STinRV1

<400> SEQUENCE: 18

```
tgttgataga gcaacattac c                                               21
```

<210> SEQ ID NO 19
<211> LENGTH: 20
<212> TYPE: DNA
<213> ORGANISM: Artificial Sequence
<220> FEATURE:
<223> OTHER INFORMATION: Synthetic primer: 467-23STinRV2

<400> SEQUENCE: 19

```
tggtaatacc ttatgggcag                                                 20
```

<210> SEQ ID NO 20
<211> LENGTH: 18
<212> TYPE: DNA
<213> ORGANISM: Artificial Sequence
<220> FEATURE:
<223> OTHER INFORMATION: Synthetic primer: 467-23STinRV3

<400> SEQUENCE: 20

```
gaacagcaac ggcagagc                                                   18
```

<210> SEQ ID NO 21
<211> LENGTH: 21
<212> TYPE: DNA
<213> ORGANISM: Artificial Sequence
<220> FEATURE:
<223> OTHER INFORMATION: Synthetic primer: 467-23STinRV4

<400> SEQUENCE: 21

```
ctaattcaat tcaaggattg g                                               21
```

<210> SEQ ID NO 22
<211> LENGTH: 21
<212> TYPE: DNA
<213> ORGANISM: Artificial Sequence
<220> FEATURE:
<223> OTHER INFORMATION: Synthetic primer: 467-23STinFW1

<400> SEQUENCE: 22

```
tggtaatgtt gctctatcaa c                                               21
```

<210> SEQ ID NO 23
<211> LENGTH: 20
<212> TYPE: DNA

```
<213> ORGANISM: Artificial Sequence
<220> FEATURE:
<223> OTHER INFORMATION: Synthetic primer: 467-23STinFW2

<400> SEQUENCE: 23
actgcccata aggtattacc                                              20

<210> SEQ ID NO 24
<211> LENGTH: 18
<212> TYPE: DNA
<213> ORGANISM: Artificial Sequence
<220> FEATURE:
<223> OTHER INFORMATION: Synthetic primer: 467-23STinFW3

<400> SEQUENCE: 24
gctctgccgt tgctgttc                                                18

<210> SEQ ID NO 25
<211> LENGTH: 35
<212> TYPE: DNA
<213> ORGANISM: Artificial Sequence
<220> FEATURE:
<223> OTHER INFORMATION: Synthetic primer: 467-23ST-N2-Nco

<400> SEQUENCE: 25
gggctgtacc atggactcta agcacaataa ctcag                             35

<210> SEQ ID NO 26
<211> LENGTH: 36
<212> TYPE: DNA
<213> ORGANISM: Artificial Sequence
<220> FEATURE:
<223> OTHER INFORMATION: Synthetic primer: 467-23ST-CO-Bm

<400> SEQUENCE: 26
cttagaatgg atccttactg caaatcactt atcaac                            36

<210> SEQ ID NO 27
<211> LENGTH: 34
<212> TYPE: DNA
<213> ORGANISM: Artificial sequence
<220> FEATURE:
<223> OTHER INFORMATION: Synthetic primer: 467-23ST-N0-Pci

<400> SEQUENCE: 27
aagggaatac atgttcgttt tttgtaaaaa aata                              34

<210> SEQ ID NO 28
<211> LENGTH: 1230
<212> TYPE: DNA
<213> ORGANISM: Photobacterium sp.
<220> FEATURE:
<221> NAME/KEY: CDS
<222> LOCATION: (1)..(1230)
<223> OTHER INFORMATION: /gene="224-23ST"
     /product="Beta-galactoside-alpha-2,3-sialyltransferase"

<400> SEQUENCE: 28 atg ctc gtt ttt tgt aaa aaa atg ttt ttt tca gtt ttt att tca cta    48
Met Leu Val Phe Cys Lys Lys Met Phe Phe Ser Val Phe Ile Ser Leu
1               5                   10                  15 atg att ctt ggg gga tgt aat agt gac tct aat cac aat aac tca gat    96
Met Ile Leu Gly Gly Cys Asn Ser Asp Ser Asn His Asn Asn Ser Asp
            20                  25                  30 gga aat att aca aaa aat aaa aca ata gaa gtt tat gtt gat aga gca   144
Gly Asn Ile Thr Lys Asn Lys Thr Ile Glu Val Tyr Val Asp Arg Ala
        35                  40                  45
```

| | | |
|---|---|---|
| aca tta cca act att caa caa atg act cag att att aat gaa aat tca<br>Thr Leu Pro Thr Ile Gln Gln Met Thr Gln Ile Ile Asn Glu Asn Ser<br>50                          55                       60 | 192 |
| aat aac aaa aaa ctg att tct tgg tca cga tac cct att aat gat gaa<br>Asn Asn Lys Lys Leu Ile Ser Trp Ser Arg Tyr Pro Ile Asn Asp Glu<br>65                     70                  75                    80 | 240 |
| gag tta ttg gaa tca att aat ggc tca ttt ttt aaa aat aat tca gag<br>Glu Leu Leu Glu Ser Ile Asn Gly Ser Phe Phe Lys Asn Asn Ser Glu<br>                    85                  90                      95 | 288 |
| cta att aag tct ctt gat tct atg ata ctt act aat gat ata aaa aaa<br>Leu Ile Lys Ser Leu Asp Ser Met Ile Leu Thr Asn Asp Ile Lys Lys<br>                 100                 105                 110 | 336 |
| gta atc atc aac ggt aat acc tta tgg gca gca gat gtc gtt aat att<br>Val Ile Ile Asn Gly Asn Thr Leu Trp Ala Ala Asp Val Val Asn Ile<br>               115                 120                 125 | 384 |
| ata aaa tca att gaa gct ttt gga aaa aaa aca gaa ata gaa cta aat<br>Ile Lys Ser Ile Glu Ala Phe Gly Lys Lys Thr Glu Ile Glu Leu Asn<br>130                        135                 140 | 432 |
| ttt tat gat gat ggt agt gcg gaa tat gtt cgt tta tat gac ttt tca<br>Phe Tyr Asp Asp Gly Ser Ala Glu Tyr Val Arg Leu Tyr Asp Phe Ser<br>145                        150                 155                 160 | 480 |
| aaa tta cca gaa tca gaa cag gaa tat aaa att tct ttg tca aag gat<br>Lys Leu Pro Glu Ser Glu Gln Glu Tyr Lys Ile Ser Leu Ser Lys Asp<br>                     165                 170                 175 | 528 |
| aac att ctt tca agt ata aat gga act caa cca ttt gaa aat gtt gtt<br>Asn Ile Leu Ser Ser Ile Asn Gly Thr Gln Pro Phe Glu Asn Val Val<br>                 180                 185                 190 | 576 |
| gaa aac att tat ggt ttt tct cag tta tac cca acg aca tat cat atg<br>Glu Asn Ile Tyr Gly Phe Ser Gln Leu Tyr Pro Thr Thr Tyr His Met<br>               195                 200                 205 | 624 |
| ctc aga gct gat att ttt gaa act aat tta cca ttg aga tcc ttg aaa<br>Leu Arg Ala Asp Ile Phe Glu Thr Asn Leu Pro Leu Arg Ser Leu Lys<br>210                        215                 220 | 672 |
| ggg gta tta tca aat aat att aag caa atg aaa tgg gac tac ttt aaa<br>Gly Val Leu Ser Asn Asn Ile Lys Gln Met Lys Trp Asp Tyr Phe Lys<br>225                        230                 235                 240 | 720 |
| act ttc aat tca cag cag aag gat aaa ttt tat aat ttt aca ggc ttt<br>Thr Phe Asn Ser Gln Gln Lys Asp Lys Phe Tyr Asn Phe Thr Gly Phe<br>                     245                 250                 255 | 768 |
| aac cca gac gaa att atg gag caa tat aaa gca agt cct aat aaa aac<br>Asn Pro Asp Glu Ile Met Glu Gln Tyr Lys Ala Ser Pro Asn Lys Asn<br>               260                 265                 270 | 816 |
| ttt att ttt gtc ggt act aat tca gga act gca aca gca gag caa caa<br>Phe Ile Phe Val Gly Thr Asn Ser Gly Thr Ala Thr Ala Glu Gln Gln<br>             275                 280                 285 | 864 |
| att gat att ctg aca gaa gct aaa aat cca aat agt cct ata ata act<br>Ile Asp Ile Leu Thr Glu Ala Lys Asn Pro Asn Ser Pro Ile Ile Thr<br>290                        295                 300 | 912 |
| aaa tca att caa ggg ttt gat ttg ttt ttt aaa gga cat cct agt gca<br>Lys Ser Ile Gln Gly Phe Asp Leu Phe Phe Lys Gly His Pro Ser Ala<br>305                        310                 315                 320 | 960 |
| act tat aat aaa caa atc ata gat gct cat aat atg att gaa att tat<br>Thr Tyr Asn Lys Gln Ile Ile Asp Ala His Asn Met Ile Glu Ile Tyr<br>                     325                 330                 335 | 1008 |
| aat aag ata cca ttt gaa gct cta atc atg act gat gca ttg cct gat<br>Asn Lys Ile Pro Phe Glu Ala Leu Ile Met Thr Asp Ala Leu Pro Asp<br>                     340                 345                 350 | 1056 |
| gct gtc ggt gga atg gga agt tcg gta ttt ttt agc ttg cca aat aca<br>Ala Val Gly Gly Met Gly Ser Ser Val Phe Phe Ser Leu Pro Asn Thr<br>               355                 360                 365 | 1104 |

```
gta gag aat aaa ttt att ttt tat aaa agt gat acg gat att gaa aat    1152
Val Glu Asn Lys Phe Ile Phe Tyr Lys Ser Asp Thr Asp Ile Glu Asn
    370                 375                 380 aat gct ctt ata caa gtt atg att gaa cta aat att gtc aat aga aat    1200
Asn Ala Leu Ile Gln Val Met Ile Glu Leu Asn Ile Val Asn Arg Asn
385                 390                 395                 400 gat gtt aag ttg ata agt gat ttg cag taa                            1230
Asp Val Lys Leu Ile Ser Asp Leu Gln
                405
```

<210> SEQ ID NO 29
<211> LENGTH: 409
<212> TYPE: PRT
<213> ORGANISM: Photobacterium sp.

<400> SEQUENCE: 29

```
Met Leu Val Phe Cys Lys Lys Met Phe Phe Ser Val Phe Ile Ser Leu
1               5                   10                  15

Met Ile Leu Gly Gly Cys Asn Ser Asp Ser Asn His Asn Asn Ser Asp
            20                  25                  30

Gly Asn Ile Thr Lys Asn Lys Thr Ile Glu Val Tyr Val Asp Arg Ala
        35                  40                  45

Thr Leu Pro Thr Ile Gln Gln Met Thr Gln Ile Ile Asn Glu Asn Ser
    50                  55                  60

Asn Asn Lys Lys Leu Ile Ser Trp Ser Arg Tyr Pro Ile Asn Asp Glu
65                  70                  75                  80

Glu Leu Leu Glu Ser Ile Asn Gly Ser Phe Phe Lys Asn Asn Ser Glu
                85                  90                  95

Leu Ile Lys Ser Leu Asp Ser Met Ile Leu Thr Asn Asp Ile Lys Lys
            100                 105                 110

Val Ile Ile Asn Gly Asn Thr Leu Trp Ala Ala Asp Val Val Asn Ile
        115                 120                 125

Ile Lys Ser Ile Glu Ala Phe Gly Lys Lys Thr Glu Ile Glu Leu Asn
    130                 135                 140

Phe Tyr Asp Asp Gly Ser Ala Glu Tyr Val Arg Leu Tyr Asp Phe Ser
145                 150                 155                 160

Lys Leu Pro Glu Ser Glu Gln Glu Tyr Lys Ile Ser Leu Ser Lys Asp
                165                 170                 175

Asn Ile Leu Ser Ser Ile Asn Gly Thr Gln Pro Phe Glu Asn Val Val
            180                 185                 190

Glu Asn Ile Tyr Gly Phe Ser Gln Leu Tyr Pro Thr Thr Tyr His Met
        195                 200                 205

Leu Arg Ala Asp Ile Phe Glu Thr Asn Leu Pro Leu Arg Ser Leu Lys
    210                 215                 220

Gly Val Leu Ser Asn Asn Ile Lys Gln Met Lys Trp Asp Tyr Phe Lys
225                 230                 235                 240

Thr Phe Asn Ser Gln Gln Lys Asp Lys Phe Tyr Asn Phe Thr Gly Phe
                245                 250                 255

Asn Pro Asp Glu Ile Met Glu Gln Tyr Lys Ala Ser Pro Asn Lys Asn
            260                 265                 270

Phe Ile Phe Val Gly Thr Asn Ser Gly Thr Ala Thr Ala Glu Gln Gln
        275                 280                 285

Ile Asp Ile Leu Thr Glu Ala Lys Asn Pro Asn Ser Pro Ile Ile Thr
    290                 295                 300

Lys Ser Ile Gln Gly Phe Asp Leu Phe Phe Lys Gly His Pro Ser Ala
305                 310                 315                 320
```

```
Thr Tyr Asn Lys Gln Ile Ile Asp Ala His Asn Met Ile Glu Ile Tyr
            325                 330                 335

Asn Lys Ile Pro Phe Glu Ala Leu Ile Met Thr Asp Ala Leu Pro Asp
            340                 345                 350

Ala Val Gly Gly Met Gly Ser Ser Val Phe Phe Ser Leu Pro Asn Thr
            355                 360                 365

Val Glu Asn Lys Phe Ile Phe Tyr Lys Ser Asp Thr Asp Ile Glu Asn
            370                 375                 380

Asn Ala Leu Ile Gln Val Met Ile Glu Leu Asn Ile Val Asn Arg Asn
385                 390                 395                 400

Asp Val Lys Leu Ile Ser Asp Leu Gln
            405

<210> SEQ ID NO 30
<211> LENGTH: 1209
<212> TYPE: DNA
<213> ORGANISM: Vibrio sp.
<220> FEATURE:
<221> NAME/KEY: CDS
<222> LOCATION: (1)..(1209)
<223> OTHER INFORMATION: /gene="FAJ16-23ST" /product="Beta-galactoside-
      alpha 2,3-sialyltransferase"

<400> SEQUENCE: 30
```

| | | |
|---|---|---|
| atg aaa aac att ata aca aaa aga atg cta att att ctt tct tct cta<br>Met Lys Asn Ile Ile Thr Lys Arg Met Leu Ile Ile Leu Ser Ser Leu<br>1               5                   10                  15 | 48 |
| ttc act att atc gga tgc aac aat gat aac agc act acc aca aat aac<br>Phe Thr Ile Ile Gly Cys Asn Asn Asp Asn Ser Thr Thr Thr Asn Asn<br>                20                  25                  30 | 96 |
| aat gcg ata gaa ata tat gtt gat aga gcc act ctt cca act att cag<br>Asn Ala Ile Glu Ile Tyr Val Asp Arg Ala Thr Leu Pro Thr Ile Gln<br>            35                  40                  45 | 144 |
| caa atg aca aaa ata gtc agt caa aaa aca agt aat aaa aaa ctt att<br>Gln Met Thr Lys Ile Val Ser Gln Lys Thr Ser Asn Lys Lys Leu Ile<br>        50                  55                  60 | 192 |
| tca tgg tct aga tac cca ata act gat aaa tcg tta tta aaa aaa att<br>Ser Trp Ser Arg Tyr Pro Ile Thr Asp Lys Ser Leu Leu Lys Lys Ile<br>65                  70                  75                  80 | 240 |
| aat gca gaa ttt ttt aaa gaa caa ttt gaa tta act gaa tca cta aaa<br>Asn Ala Glu Phe Phe Lys Glu Gln Phe Glu Leu Thr Glu Ser Leu Lys<br>                85                  90                  95 | 288 |
| aac atc ata tta agt gaa aat atc gac aac ctt ata atc cat ggt aat<br>Asn Ile Ile Leu Ser Glu Asn Ile Asp Asn Leu Ile Ile His Gly Asn<br>            100                 105                 110 | 336 |
| aca ctc tgg tct ata gat gta gta gat ata ata aaa gaa gtt aat ctc<br>Thr Leu Trp Ser Ile Asp Val Val Asp Ile Ile Lys Glu Val Asn Leu<br>        115                 120                 125 | 384 |
| ctc ggg aaa aac ata cca att gaa tta cat ttt tat gac gat ggt tca<br>Leu Gly Lys Asn Ile Pro Ile Glu Leu His Phe Tyr Asp Asp Gly Ser<br>    130                 135                 140 | 432 |
| gct gaa tat gtg aga ata tac gaa ttt tca aaa ctg cct gag tca gaa<br>Ala Glu Tyr Val Arg Ile Tyr Glu Phe Ser Lys Leu Pro Glu Ser Glu<br>145                 150                 155                 160 | 480 |
| caa aaa tac aaa acg tca cta tct aaa aac aac ata aaa ttc agc ata<br>Gln Lys Tyr Lys Thr Ser Leu Ser Lys Asn Asn Ile Lys Phe Ser Ile<br>                165                 170                 175 | 528 |
| gat ggg act gat tca ttt aaa aac aca ata gaa aac att tat gga ttc<br>Asp Gly Thr Asp Ser Phe Lys Asn Thr Ile Glu Asn Ile Tyr Gly Phe<br>            180                 185                 190 | 576 |

```
tca caa tta tac cca aca aca tat cac atg tta aga gcg gat ata ttc      624
Ser Gln Leu Tyr Pro Thr Thr Tyr His Met Leu Arg Ala Asp Ile Phe
        195                 200                 205 gat aca aca tta aaa ata aac cca ttg aga gag ttg ctt tca aat aat      672
Asp Thr Thr Leu Lys Ile Asn Pro Leu Arg Glu Leu Leu Ser Asn Asn
210                 215                 220 ata aaa caa atg aaa tgg gat tac ttt aaa gac ttt aat tat aaa caa      720
Ile Lys Gln Met Lys Trp Asp Tyr Phe Lys Asp Phe Asn Tyr Lys Gln
225                 230                 235                 240 aaa gat att ttt tac tct ttg act aac ttc aac cca aaa gaa ata cag      768
Lys Asp Ile Phe Tyr Ser Leu Thr Asn Phe Asn Pro Lys Glu Ile Gln
            245                 250                 255 gaa gat ttc aac aaa aac tca aat aaa aac ttc att ttt ata gga agt      816
Glu Asp Phe Asn Lys Asn Ser Asn Lys Asn Phe Ile Phe Ile Gly Ser
        260                 265                 270 aat agt gct aca gca aca gca gaa gag caa ata aat att att tca gaa      864
Asn Ser Ala Thr Ala Thr Ala Glu Glu Gln Ile Asn Ile Ile Ser Glu
    275                 280                 285 gca aaa aaa gaa aat agt agc att ata aca aac tct ata tca gac tat      912
Ala Lys Lys Glu Asn Ser Ser Ile Ile Thr Asn Ser Ile Ser Asp Tyr
290                 295                 300 gat tta ttt ttc aaa ggc cac cca agc gcc aca ttc aac gaa caa ata      960
Asp Leu Phe Phe Lys Gly His Pro Ser Ala Thr Phe Asn Glu Gln Ile
305                 310                 315                 320 att aat gca cac gat atg atc gaa att aac aac aag atc cca ttc gaa     1008
Ile Asn Ala His Asp Met Ile Glu Ile Asn Asn Lys Ile Pro Phe Glu
            325                 330                 335 gcg tta ata atg aca gga ata cta cct gat gct gta ggt ggg atg ggt     1056
Ala Leu Ile Met Thr Gly Ile Leu Pro Asp Ala Val Gly Gly Met Gly
        340                 345                 350 agt tct gtt ttc ttt agc att cca aaa gaa gtg aaa aac aaa ttt gtt     1104
Ser Ser Val Phe Phe Ser Ile Pro Lys Glu Val Lys Asn Lys Phe Val
    355                 360                 365 ttt tat aaa agc ggt acg gat ata gaa aac aat agc cta ata caa gta     1152
Phe Tyr Lys Ser Gly Thr Asp Ile Glu Asn Asn Ser Leu Ile Gln Val
370                 375                 380 atg cta aaa ctt aac tta ata aat cgt gac aat ata aaa cta atc agc     1200
Met Leu Lys Leu Asn Leu Ile Asn Arg Asp Asn Ile Lys Leu Ile Ser
385                 390                 395                 400 gac att taa                                                         1209
Asp Ile <210> SEQ ID NO 31
<211> LENGTH: 402
<212> TYPE: PRT
<213> ORGANISM: Vibrio sp.

<400> SEQUENCE: 31

Met Lys Asn Ile Ile Thr Lys Arg Met Leu Ile Ile Leu Ser Ser Leu
1               5                   10                  15

Phe Thr Ile Ile Gly Cys Asn Asn Asp Asn Ser Thr Thr Asn Asn
            20                  25                  30

Asn Ala Ile Glu Ile Tyr Val Asp Arg Ala Thr Leu Pro Thr Ile Gln
        35                  40                  45

Gln Met Thr Lys Ile Val Ser Gln Lys Thr Ser Asn Lys Lys Leu Ile
    50                  55                  60

Ser Trp Ser Arg Tyr Pro Ile Thr Asp Lys Ser Leu Leu Lys Ile
65                  70                  75                  80

Asn Ala Glu Phe Phe Lys Glu Gln Phe Glu Leu Thr Glu Ser Leu Lys
                85                  90                  95
```

Asn Ile Ile Leu Ser Glu Asn Ile Asp Asn Leu Ile Ile His Gly Asn
            100                 105                 110

Thr Leu Trp Ser Ile Asp Val Val Asp Ile Ile Lys Glu Val Asn Leu
            115                 120                 125

Leu Gly Lys Asn Ile Pro Ile Glu Leu His Phe Tyr Asp Asp Gly Ser
130                 135                 140

Ala Glu Tyr Val Arg Ile Tyr Glu Phe Ser Lys Leu Pro Glu Ser Glu
145                 150                 155                 160

Gln Lys Tyr Lys Thr Ser Leu Ser Lys Asn Asn Ile Lys Phe Ser Ile
                165                 170                 175

Asp Gly Thr Asp Ser Phe Lys Asn Thr Ile Glu Asn Ile Tyr Gly Phe
            180                 185                 190

Ser Gln Leu Tyr Pro Thr Thr Tyr His Met Leu Arg Ala Asp Ile Phe
            195                 200                 205

Asp Thr Thr Leu Lys Ile Asn Pro Leu Arg Glu Leu Leu Ser Asn Asn
210                 215                 220

Ile Lys Gln Met Lys Trp Asp Tyr Phe Lys Asp Phe Asn Tyr Lys Gln
225                 230                 235                 240

Lys Asp Ile Phe Tyr Ser Leu Thr Asn Phe Asn Pro Lys Glu Ile Gln
                245                 250                 255

Glu Asp Phe Asn Lys Asn Ser Asn Lys Asn Phe Ile Phe Ile Gly Ser
            260                 265                 270

Asn Ser Ala Thr Ala Thr Ala Glu Glu Gln Ile Asn Ile Ile Ser Glu
            275                 280                 285

Ala Lys Lys Glu Asn Ser Ser Ile Ile Thr Asn Ser Ile Ser Asp Tyr
290                 295                 300

Asp Leu Phe Phe Lys Gly His Pro Ser Ala Thr Phe Asn Glu Gln Ile
305                 310                 315                 320

Ile Asn Ala His Asp Met Ile Glu Ile Asn Asn Lys Ile Pro Phe Glu
                325                 330                 335

Ala Leu Ile Met Thr Gly Ile Leu Pro Asp Ala Val Gly Gly Met Gly
            340                 345                 350

Ser Ser Val Phe Phe Ser Ile Pro Lys Glu Val Lys Asn Lys Phe Val
            355                 360                 365

Phe Tyr Lys Ser Gly Thr Asp Ile Glu Asn Asn Ser Leu Ile Gln Val
370                 375                 380

Met Leu Lys Leu Asn Leu Ile Asn Arg Asp Asn Ile Lys Leu Ile Ser
385                 390                 395                 400

Asp Ile

<210> SEQ ID NO 32
<211> LENGTH: 1500
<212> TYPE: DNA
<213> ORGANISM: Photobacterium sp.

<400> SEQUENCE: 32
attgaacgct ggcggcaggc ctaacacatg caagtcgagc ggtaacagat tgatagcttg     60
ctatcaatgc tgacgagcgg cggacgggtg agtaatgcct gggaatatac cctgatgtgg    120
gggataacta ttggaaacga tagctaatac cgcataatct cttcggagca aagaggggga    180
ccttcgggcc tctcgcgtca ggattagccc aggtgggatt agctagttgg tggggtaatg    240
gctcaccaag cgacgatccc tagctggtc tgagaggatg atcagccaca ctggaactga    300
gacacggtcc agactcctac gggaggcagc agtggggaat attgcacaat ggggga aacc    360

```
ctgatgcagc catgccgcgt gtatgaagaa ggccttcggg ttgtaaagta ctttcagttg    420
tgaggaaggc agttaagtta atagcttagy tgtttgacgt tagcaacaga agaagcaccg    480
gctaactccg tgccagcagc cgcggtaata cggagggtgc gagcgttaat cggaattact    540
gggcgtaaag cgcatgcagg cggtctgtta agcaagatgt gaaagcccgg ggctcaacct    600
cggaacagca ttttgaactg gcagactaga gtcttgtaga ggggggtaga atttcaggtg    660
tagcggtgaa atgcgtagag atctgaagga ataccgtgg cgaaggcggc cccctggaca    720
aagactgacg ctcagatgcg aaagcgtggg gagcaaacag gattagatac cctggtagtc    780
cacgccgtaa acgatgtcta cttgaaggtt gtggccttga gccgtggctt tcggagctaa    840
cgcgttaagt agaccgcctg gggagtacgg tcgcaagatt aaaactcaaa tgaattgacg    900
ggggcccgca caagcggtgg agcatgtggt ttaattcgat gcaacgcgaa gaaccttacc    960
tactcttgac atccagagaa ttcgctagag atagcttagt gccttcggga actctgagac   1020
aggtgctgca tggctgtcgt cagctcgtgt tgtgaaatgt tgggttaagt cccgcaacga   1080
gcgcaaccct tatccttgtt tgccagcacg taatggtggg aactccaggg agactgccgg   1140
tgataaaccg gaggaaggtg gggacgacgt caagtcatca tggcccttac gagtagggct   1200
acacacgtgc tacaatggcg tatacagagg gctgcaaact agcgatagta agcgaatccc   1260
acaaagtacg tcgtagtccg gattggagtc tgcaactcga ctccatgaag tcggaatcgc   1320
tagtaatcgt gaatcagaat gtcacggtga atacgttccc gggccttgta cacaccgccc   1380
gtcacaccat gggagtgggc tgcaccagaa gtagatagct taaccttcgg gagggcgttt   1440
accacggtgt ggttcatgac tggggtgaag tcgtaacaag gtagcccttag ggaacctgg   1500
```

<210> SEQ ID NO 33
<211> LENGTH: 1498
<212> TYPE: DNA
<213> ORGANISM: Vibrio sp.

<400> SEQUENCE: 33

```
attgaacgct ggcggcaggc ctaacacatg caagtcgagc ggaaacgaga agtagcttgc     60
tacttcggcg tcgagcggcg gacgggtgag taatgcatag gaagttgccc agtagagggg    120
gataaccatt ggaaacgatg gctaataccg cataacctct tcggagcaaa gcggggggacc    180 ttcgggcctc gcgctactgg atacgcctat gtgggattag ctagttggtg aggtaatggc    240
tcaccaaggc gacgatccct agctggtctg agaggatgat cagccacact gggactgaga    300
cacggcccag actcctacgg gaggcagcag tggggaatat tgcacaatgg gcgaaagcct    360
gatgcagcca tgccgcgtgt atgaagaagg ccttcgggtt gtaaagtact ttcagttgtg    420
aggaagggtg tgtagttaat aactgcgcat tttgacgtta gcaacagaag aagcaccggc    480
taactccgtg ccagcagccg cggtaatacg gagggtgcga gcgttaatcg gaattactgg    540
gcgtaaagcg catgcaggtg gtttgttaag tcagatgtga aagcccgggg ctcaacctcg    600
gaaggtcatt tgaaactggc aaactagagt actgtagagg ggggtagaat tcaggtgta    660 gcggtgaaat gcgtagagat ctgaaggaat accagtggcg aaggcggccc cctggacaga    720
tactgacact cagatgcgaa agcgtgggga gcaaacagga ttagataccc tggtagtcca    780
cgccgtaaac gatgtctact ggaggttgt ggccttgagc cgtggctttc ggagctaacg    840
cgttaagtag accgcctggg gagtacggtc gcaagattaa aactcaaatg aattgacggg    900
ggcccgcaca agcggtggag catgtggttt aattcgatgc aacgcgaaga accttaccta    960
ctcttgacat ccagagaact ttccagagat ggattggtgc cttcgggaac tctgagacag   1020
```

| | | |
|---|---|---|
| gtgctgcatg gctgtcgtca gctcgtgttg tgaaatgttg ggttaagtcc cgcaacgagc | 1080 |
| gcaaccctta tccttgtttg ccagcgagta atgtcgggaa ctccaggag actgccggtg | 1140 |
| ataaaccgga ggaaggtggg gacgacgtca agtcatcatg gcccttacga gtagggctac | 1200 |
| acacgtgcta caatggcgca tacagagggc agcaagctag cgatagtgag cgaatcccaa | 1260 |
| aaagtgcgtc gtagtccgga ttggagtctg caactcgact ccatgaagtc ggaatcgcta | 1320 |
| gtaatcgtgg atcagaatgc cacggtgaat acgttcccgg gccttgtaca caccgcccgt | 1380 |
| cacaccatgg gagtgggctg caaaagaagt aggtagttta accttcggga ggacgcttac | 1440 |
| cactttgtgg ttcatgactg gggtgaagtc gtaacaaggt agccctaggg gaacctgg | 1498 |

<210> SEQ ID NO 34
<211> LENGTH: 20
<212> TYPE: DNA
<213> ORGANISM: Artificial Sequence
<220> FEATURE:
<223> OTHER INFORMATION: Synthetic primer: 224-23ST-inRV1

<400> SEQUENCE: 34
caggaactgc aacagcagag                                               20

<210> SEQ ID NO 35
<211> LENGTH: 34
<212> TYPE: DNA
<213> ORGANISM: Artificial Sequence
<220> FEATURE:
<223> OTHER INFORMATION: Synthetic primer: 224-23ST-N0-Pci

<400> SEQUENCE: 35
aagggaatac atgttcgttt tttgtaaaaa aatg                               34

<210> SEQ ID NO 36
<211> LENGTH: 35
<212> TYPE: DNA
<213> ORGANISM: Artificial Sequence
<220> FEATURE:
<223> OTHER INFORMATION: Synthetic primer: 224-23ST-N1-Nco

<400> SEQUENCE: 36
gggatgtacc atggactcta atcacaataa ctcag                              35

<210> SEQ ID NO 37
<211> LENGTH: 36
<212> TYPE: DNA
<213> ORGANISM: Artificial sequence
<220> FEATURE:
<223> OTHER INFORMATION: Synthetic primer: 224-23ST-C0new-Bm

<400> SEQUENCE: 37
attaaaatgg atccttactg caaatcactt atcaac                             36

<210> SEQ ID NO 38
<211> LENGTH: 20
<212> TYPE: DNA
<213> ORGANISM: Artificial Sequence
<220> FEATURE:
<223> OTHER INFORMATION: Synthetic primer: FAJEc3.6RV1

<400> SEQUENCE: 38
ttcaaaactg cctgagtcag                                               20

<210> SEQ ID NO 39
<211> LENGTH: 20
<212> TYPE: DNA

<210> SEQ ID NO 39
<211> LENGTH: 20
<212> TYPE: DNA
<213> ORGANISM: Artificial Sequence
<220> FEATURE:
<223> OTHER INFORMATION: Synthetic primer: FAJEc3.6RV2

<400> SEQUENCE: 39
atttcatggt ctagataccc                                               20

<210> SEQ ID NO 40
<211> LENGTH: 20
<212> TYPE: DNA
<213> ORGANISM: Artificial Sequence
<220> FEATURE:
<223> OTHER INFORMATION: Synthetic primer: FAJ23STinFW3

<400> SEQUENCE: 40
ctgactcagg cagttttgaa                                               20

<210> SEQ ID NO 41
<211> LENGTH: 21
<212> TYPE: DNA
<213> ORGANISM: Artificial Sequence
<220> FEATURE:
<223> OTHER INFORMATION: Synthetic primer: FAJ23STinFW4

<400> SEQUENCE: 41
gaaagcaact ctctcaatgg g                                             21

<210> SEQ ID NO 42
<211> LENGTH: 21
<212> TYPE: DNA
<213> ORGANISM: Artificial Sequence
<220> FEATURE:
<223> OTHER INFORMATION: Synthetic primer: FAJ23STinRV3

<400> SEQUENCE: 42
ataaacccat tgagagagtt g                                             21

<210> SEQ ID NO 43
<211> LENGTH: 37
<212> TYPE: DNA
<213> ORGANISM: Artificial Sequence
<220> FEATURE:
<223> OTHER INFORMATION: Synthetic primer: FAJ23STN0-BspHI

<400> SEQUENCE: 43
tggataactc atgaaaaaca ttataacaaa aagaatg                            37

<210> SEQ ID NO 44
<211> LENGTH: 34
<212> TYPE: DNA
<213> ORGANISM: Artificial Sequence
<220> FEATURE:
<223> OTHER INFORMATION: Synthetic primer: FAJ23STN1-BspHI

<400> SEQUENCE: 44
tattatcgtc atgaacaatg ataacagcac tacc                               34

<210> SEQ ID NO 45
<211> LENGTH: 38
<212> TYPE: DNA
<213> ORGANISM: Artificial Sequence
<220> FEATURE:
<223> OTHER INFORMATION: Synthetic primer: FAJ23STC0-BamHI

<400> SEQUENCE: 45 tcttttagg atccttaaat gtcgctgatt agttttat                            38

<210> SEQ ID NO 46
<211> LENGTH: 675
<212> TYPE: PRT
<213> ORGANISM: Photobacterium damselae

<400> SEQUENCE: 46

```
Met Lys Lys Ile Leu Thr Val Leu Ser Ile Phe Ile Leu Ser Ala Cys
1               5                   10                  15

Asn Ser Asp Asn Thr Ser Leu Lys Glu Thr Val Ser Ser Asn Ser Ala
            20                  25                  30

Asp Val Val Glu Thr Glu Thr Tyr Gln Leu Thr Pro Ile Asp Ala Pro
        35                  40                  45

Ser Ser Phe Leu Ser His Ser Trp Glu Gln Thr Cys Gly Thr Pro Ile
    50                  55                  60

Leu Asn Glu Ser Asp Lys Gln Ala Ile Ser Phe Asp Phe Val Ala Pro
65                  70                  75                  80

Glu Leu Lys Gln Asp Glu Lys Tyr Cys Phe Thr Phe Lys Gly Ile Thr
                85                  90                  95

Gly Asp His Arg Tyr Ile Thr Asn Thr Thr Leu Thr Val Val Ala Pro
            100                 105                 110

Thr Leu Glu Val Tyr Ile Asp His Ala Ser Leu Pro Ser Leu Gln Gln
        115                 120                 125

Leu Ile His Ile Ile Gln Ala Lys Asp Glu Tyr Pro Ser Asn Gln Arg
    130                 135                 140

Phe Val Ser Trp Lys Arg Val Thr Val Asp Ala Asp Asn Ala Asn Lys
145                 150                 155                 160

Leu Asn Ile His Thr Tyr Pro Leu Lys Gly Asn Asn Thr Ser Pro Glu
                165                 170                 175

Met Val Ala Ala Ile Asp Glu Tyr Ala Gln Ser Lys Asn Arg Leu Asn
            180                 185                 190

Ile Glu Phe Tyr Thr Asn Thr Ala His Val Phe Asn Asn Leu Pro Pro
        195                 200                 205

Ile Ile Gln Pro Leu Tyr Asn Asn Glu Lys Val Lys Ile Ser His Ile
    210                 215                 220

Ser Leu Tyr Asp Asp Gly Ser Ser Glu Tyr Val Ser Leu Tyr Gln Trp
225                 230                 235                 240

Lys Asp Thr Pro Asn Lys Ile Glu Thr Leu Glu Gly Glu Val Ser Leu
                245                 250                 255

Leu Ala Asn Tyr Leu Ala Gly Thr Ser Pro Asp Ala Pro Lys Gly Met
            260                 265                 270

Gly Asn Arg Tyr Asn Trp His Lys Leu Tyr Asp Thr Asp Tyr Tyr Phe
        275                 280                 285

Leu Arg Glu Asp Tyr Leu Asp Val Glu Ala Asn Leu His Asp Leu Arg
    290                 295                 300

Asp Tyr Leu Gly Ser Ser Ala Lys Gln Met Pro Trp Asp Glu Phe Ala
305                 310                 315                 320

Lys Leu Ser Asp Ser Gln Gln Thr Leu Phe Leu Asp Ile Val Gly Phe
                325                 330                 335

Asp Lys Glu Gln Leu Gln Gln Gln Tyr Ser Gln Ser Pro Leu Pro Asn
            340                 345                 350

Phe Ile Phe Thr Gly Thr Thr Thr Trp Ala Gly Gly Glu Thr Lys Glu
        355                 360                 365

Tyr Tyr Ala Gln Gln Gln Val Asn Val Ile Asn Asn Ala Ile Asn Glu
    370                 375                 380
```

Thr Ser Pro Tyr Tyr Leu Gly Lys Asp Tyr Asp Leu Phe Phe Lys Gly
385 390 395 400

His Pro Ala Gly Gly Val Ile Asn Asp Ile Ile Leu Gly Ser Phe Pro
405 410 415

Asp Met Ile Asn Ile Pro Ala Lys Ile Ser Phe Glu Val Leu Met Met
420 425 430

Thr Asp Met Leu Pro Asp Thr Val Ala Gly Ile Ala Ser Ser Leu Tyr
435 440 445

Phe Thr Ile Pro Ala Asp Lys Val Asn Phe Ile Val Phe Thr Ser Ser
450 455 460

Asp Thr Ile Thr Asp Arg Glu Glu Ala Leu Lys Ser Pro Leu Val Gln
465 470 475 480

Val Met Leu Thr Leu Gly Ile Val Lys Glu Lys Asp Val Leu Phe Trp
485 490 495

Ala Asp His Lys Val Asn Ser Met Glu Val Ala Ile Asp Glu Ala Cys
500 505 510

Thr Arg Ile Ile Ala Lys Arg Gln Pro Thr Ala Ser Asp Leu Arg Leu
515 520 525

Val Ile Ala Ile Ile Lys Thr Ile Thr Asp Leu Glu Arg Ile Gly Asp
530 535 540

Val Ala Glu Ser Ile Ala Lys Val Ala Leu Glu Ser Phe Ser Asn Lys
545 550 555 560

Gln Tyr Asn Leu Leu Val Ser Leu Glu Ser Leu Gly Gln His Thr Val
565 570 575

Arg Met Leu His Glu Val Leu Asp Ala Phe Ala Arg Met Asp Val Lys
580 585 590

Ala Ala Ile Glu Val Tyr Gln Glu Asp Asp Arg Ile Asp Gln Glu Tyr
595 600 605

Glu Ser Ile Val Arg Gln Leu Met Ala His Met Met Glu Asp Pro Ser
610 615 620

Ser Ile Pro Asn Val Met Lys Val Met Trp Ala Ala Arg Ser Ile Glu
625 630 635 640

Arg Val Gly Asp Arg Cys Gln Asn Ile Cys Glu Tyr Ile Ile Tyr Phe
645 650 655

Val Lys Gly Lys Asp Val Arg His Thr Lys Pro Asp Asp Phe Gly Thr
660 665 670

Met Leu Asp
675

<210> SEQ ID NO 47
<211> LENGTH: 412
<212> TYPE: PRT
<213> ORGANISM: Pasteurella multocida

<400> SEQUENCE: 47

Met Lys Asn Arg Arg Leu Asn Phe Lys Leu Phe Phe Leu Ile Ile Phe
1 5 10 15

Ser Leu Phe Ser Thr Leu Ser Trp Ser Lys Thr Ile Thr Leu Tyr Leu
20 25 30

Asp Pro Ala Ser Leu Pro Ala Leu Asn Gln Leu Met Asp Phe Thr Gln
35 40 45

Asn Asn Glu Asp Lys Thr His Pro Arg Ile Phe Gly Leu Ser Arg Phe
50 55 60

Lys Ile Pro Asp Asn Ile Ile Thr Gln Tyr Gln Asn Ile His Phe Val
65 70 75 80

-continued

```
Glu Leu Lys Asp Asn Arg Pro Thr Glu Ala Leu Phe Thr Ile Leu Asp
                 85                  90                  95
Gln Tyr Pro Gly Asn Ile Glu Leu Asn Ile His Leu Asn Ile Ala His
            100                 105                 110
Ser Val Gln Leu Ile Arg Pro Ile Leu Ala Tyr Arg Phe Lys His Leu
            115                 120                 125
Asp Arg Val Ser Ile Gln Gln Leu Asn Leu Tyr Asp Asp Gly Ser Met
        130                 135                 140
Glu Tyr Val Asp Leu Glu Lys Glu Glu Asn Lys Asp Ile Ser Ala Glu
145                 150                 155                 160
Ile Lys Gln Ala Glu Lys Gln Leu Ser His Tyr Leu Leu Thr Gly Lys
                165                 170                 175
Ile Lys Phe Asp Asn Pro Thr Ile Ala Arg Tyr Val Trp Gln Ser Ala
            180                 185                 190
Phe Pro Val Lys Tyr His Phe Leu Ser Thr Asp Tyr Phe Glu Lys Ala
            195                 200                 205
Glu Phe Leu Gln Pro Leu Lys Glu Tyr Leu Ala Glu Asn Tyr Gln Lys
        210                 215                 220
Met Asp Trp Thr Ala Tyr Gln Gln Leu Thr Pro Glu Gln Gln Ala Phe
225                 230                 235                 240
Tyr Leu Thr Leu Val Gly Phe Asn Asp Glu Val Lys Gln Ser Leu Glu
                245                 250                 255
Val Gln Gln Ala Lys Phe Ile Phe Thr Gly Thr Thr Thr Trp Glu Gly
            260                 265                 270
Asn Thr Asp Val Arg Glu Tyr Tyr Ala Gln Gln Gln Leu Asn Leu Leu
        275                 280                 285
Asn His Phe Thr Gln Ala Glu Gly Asp Leu Phe Ile Gly Asp His Tyr
290                 295                 300
Lys Ile Tyr Phe Lys Gly His Pro Arg Gly Gly Glu Ile Asn Asp Tyr
305                 310                 315                 320
Ile Leu Asn Asn Ala Lys Asn Ile Thr Asn Ile Pro Ala Asn Ile Ser
                325                 330                 335
Phe Glu Val Leu Met Met Thr Gly Leu Leu Pro Asp Lys Val Gly Gly
            340                 345                 350
Val Ala Ser Ser Leu Tyr Phe Ser Leu Pro Lys Glu Lys Ile Ser His
            355                 360                 365
Ile Ile Phe Thr Ser Asn Lys Gln Val Lys Ser Lys Glu Asp Ala Leu
        370                 375                 380
Asn Asn Pro Tyr Val Lys Val Met Arg Arg Leu Gly Ile Ile Asp Glu
385                 390                 395                 400
Ser Gln Val Ile Phe Trp Asp Ser Leu Lys Gln Leu
                405                 410
```

β-GALACTOSIDE-α2,3-SIALYLTRANSFERASE, A GENE ENCODING THEREOF, AND A METHOD FOR PRODUCING THEREOF

TECHNICAL FIELD

The present invention relates to a novel β-galactoside-α2, 3-sialyltransferase, a gene encoding the enzyme, a microorganism producing the enzyme and a method for producing the enzyme.

BACKGROUND ART

Glycosyltransferases are enzymes involved in in vivo biosynthesis of sugar chains on glycoproteins, glycolipids and the like. Their reaction products, i.e., sugar chains on glycoproteins, glycolipids and the like (hereinafter referred to as "complex carbohydrate sugar chains") have very important functions in the body. For example, sugar chains have been shown to be important molecules primarily in mammalian cells, which play a role in cell-cell and cell-extracellular matrix signaling and serve as tags for complex carbohydrates during differentiation and/or development.

As described above, sugar chains have very important functions. Erythropoietin can be presented as a specific example where sugar chains are applied. Although erythropoietin is inherently a glycoprotein, further attempts have been made to increase the number of sugar chains on erythropoietin, as a result of which recombinant erythropoietin proteins with an extended life span have been produced and are now commercially available.

It can also be expected that in the future, further developments will take place for such products in which sugar chains are applied, including pharmaceuticals and functional foods. For this reason, glycosyltransferases will increase in importance as a means for synthesizing and producing sugar chains.

Until now, about 150 or more glycosyltransferase genes have been isolated from eukaryotic organisms including humans, mice, rats and yeast, and proteins having glycosyltransferase activity have also been expressed in production systems where CHO or E. coli cells are used as host cells. On the other hand, several glycosyltransferase genes have also been isolated from bacteria which are prokaryotic organisms. Moreover, proteins having glycosyltransferase activity have been expressed in recombinant production systems using E. coli and identified for their substrate specificity and/or various enzymatic properties.

Among sugars constituting sugar chains, sialic acid that is often located at the nonreducing termini is a very important sugar in terms of sugar chain functions, and hence sialyltransferase is one of the most in demand enzymes among glycosyltransferases, which are now increasing in importance.

As to α2,3-sialyltransferases and their genes, many reports have been issued for those derived from animals, particularly mammals (see, e.g., Harduin-Lepers, A. et al., Biochem J., 15; 352 Pt 1:37-48 (2000); Young-Choon Lee et al., J. Biol. Chem., 23; 274(17):11958-67 (1999); Lee, Y-C. et al., J. Biochem., 216, 377-385 (19.93); Chang, M-L. et al., Glycobiology, 5, 319-325 (1995); and Gillespie, W. et al., J. Biol. Chem., 267, 21004-21010 (1992)). However, such animal-derived enzymes are very expensive because they are difficult to purify and hence cannot be obtained in large amounts. Moreover, such enzymes have a problem in that they have poor stability as enzymes.

In contrast, as microorganism-derived α2,3-sialyltransferases and their genes, those obtained from microorganisms belonging to the genera Neisseria, Campylobacter, Haemophilus and Pasteurella have been reported (see, e.g., WO97/047749, WO99/049051, WO01/077314, WO03/027297). However, there is no report showing that α2,3-sialyltransferase has been obtained from microorganisms belonging to the Vibrionaceae, and there is also no report showing that a protein having α2,3-sialyltransferase activity is present in microorganisms belonging to the Vibrionaceae.

Patent Document 1: International Publication No. WO97/047749A

Patent Document 2: International Publication No. WO99/049051A

Patent Document 3: International Publication No. WO01/077314A

Patent Document 4: International Publication No. WO03/027297A

Non-patent Document 1: Harduin-Lepers, A. et al., Biochem. J., 15; 352 Pt 1:37-48 (2000)

Non-patent Document 2: Young-Choon Lee at al., J. Biol. Chem., 23; 274(17):11958-67 (1999)

Non-patent Document 3: Lee, Y-C. et al., J. Biochem., 216, 377-385 (1993)

Non-patent Document 4: Chang, M-L. et al., Glycobiology, 5, 319-325 (1995)

Non-patent Document 5: Gillespie, W. et al., J. Biol. Chem., 267, 21004-21010 (1992)

DISCLOSURE OF THE INVENTION

Problems to be Solved by the Invention

One problem to be solved by the present invention is to provide a novel β-galactoside-α2,3-sialyltransferase derived from a microorganism of the Vibrionaceae, and a gene encoding the same. Another problem to be solved by the present invention is to provide a method for high production of this enzyme by gene recombination technology using the gene of the present invention encoding β-galactoside-α2,3-sialyltransferase.

Means for Solving the Problems

As a result of extensive and intensive efforts, the inventors of the present invention have found that microorganisms belonging to the Vibrionaceae produce novel enzymes capable of transferring sialic acid in α-2,3 linkage to a galactose, glucose, mannose, fucose, N-acetylglucosamine or N-acetylgalactosamine residue in sugar chains. This finding led to the completion of the present invention. The present invention provides a novel β-galactoside-α2,3-sialyltransferase and a nucleic acid encoding the same, as well as a method for producing the sialyltransferase.

The present invention will now be illustrated in detail below.

β-Galactoside-α2,3-sialyltransferase

The present invention provides a novel β-galactoside-α2, 3-sialyltransferase. As used herein, the term "β-galactoside-α2,3-sialyltransferase" is intended to mean a protein having the ability to transfer sialic acid from cytidine monophosphate (CMP)-sialic acid to the 3-position of a galactose residue in complex carbohydrate sugar chains or free sugar chains, to the 3-position of galactose present in oligosaccharides such as lactose or N-acetyllactosamine, or to the 3-position of a monosaccharide (e.g., galactose, glucose, mannose, fucose, N-acetylglucosamine or N-acetylgalactosamine) which may be used as a constituting member of complex carbohydrates and has a hydroxyl group on the carbon at the 3-position. As used herein, the term "β-galactoside-α2,3-sialyltransferase activity" is intended to mean the ability described above for β-galactoside-α2,3-sialyltransferase. The term "sialic acid" as used herein refers to a neuraminic acid derivative belonging to the sialic acid family. More specifically, it refers to N-acetylneuraminic acid (Neu5Ac), N-glycolylneuraminic acid (Neu5Gc), 5-deamino-5-hydroxyneuraminic acid (KDN), disialic acid or the like.

The β-galactoside-α2,3-sialyltransferase of the present invention is a protein comprising the amino acid sequence shown in SEQ ID NO: 2, SEQ ID NO: 29 or SEQ ID NO: 31. Alternatively, the β-galactoside-α2,3-sialyltransferase of the present invention is a protein encoded by a nucleic acid comprising the nucleotide sequence shown in SEQ ID NO: 1, SEQ ID NO: 28 or SEQ ID NO: 30.

In the β-galactoside-α2,3-sialyltransferase of the present invention comprising the amino acid sequence shown in SEQ ID NO: 2, amino acids 1-21 of SEQ ID NO: 2 constitutes a signal sequence. Thus, the β-galactoside-α2,3-sialyltransferase of the present invention may be a protein comprising an amino acid sequence covering amino acids 22-409 of SEQ ID NO: 2. Alternatively, the β-galactoside-α2,3-sialyltransferase of the present invention may be a protein encoded by a nucleic acid comprising a nucleotide sequence covering nucleotides 64-1230 of SEQ ID NO: 1.

In the β-galactoside-α2,3-sialyltransferase of the present invention comprising the amino acid sequence shown in SEQ ID NO: 29, amino acids 1-24 of SEQ ID NO: 29 are expected to constitute a signal sequence. Thus, the 3-galactoside-α2,3-sialyltransferase of the present invention may be a protein comprising an amino acid sequence covering amino acids 25-409 of SEQ ID NO: 29. Alternatively, the β-galactoside-α2,3-sialyltransferase of the present invention may be a protein encoded by a nucleic acid comprising a nucleotide sequence covering nucleotides 73-1230 of SEQ ID NO: 28.

In the β-galactoside-α2,3-sialyltransferase of the present invention comprising the amino acid sequence shown in SEQ ID NO: 31, amino acids 1-22 of SEQ ID NO: 31 are expected to constitute a signal sequence. Thus, the β-galactoside-α2,3-sialyltransferase of the present invention may be a protein comprising an amino acid sequence covering amino acids 23-402 of SEQ ID NO: 31. Alternatively, the β-galactoside-α2,3-sialyltransferase of the present invention may be a protein encoded by a nucleic acid comprising a nucleotide sequence covering nucleotides 67-1209 of SEQ ID NO: 30.

The present invention also encompasses mutants of the above β-galactoside-α2,3-sialyltransferases of the present invention, i.e., mutated proteins having β-galactoside-α2,3-sialyltransferase activity. Such mutated proteins also fall within the β-galactoside-α2,3-sialyltransferase of the present invention.

The mutant protein of the present invention may be a protein having β-galactoside-α2,3-sialyltransferase activity, which comprises an amino acid sequence comprising deletion, substitution, insertion and/or addition of one or more amino acids in an amino acid sequence selected from the group consisting of SEQ ID NO. 2, amino acids 22-409 of SEQ ID NO: 2, SEQ ID NO: 29, amino acids 25-409 of SEQ ID NO: 29, SEQ ID NO: 31, and amino acids 23-402 of SEQ ID NO: 31. The substitution may be conservative, which means the replacement of a certain amino acid residue by another residue having similar physical and chemical characteristics. Non-limiting examples of conservative substitution include replacement between aliphatic group-containing amino acid residues such as Ile, Val, Leu or Ala, and replacement between polar residues such as Lys-Arg, Glu-Asp or Gln-Asn replacement.

Mutants derived by amino acid deletion, substitution, insertion and/or addition can be prepared when DNAs encoding their wild-type proteins are subjected to, for example, well-known site-directed mutagenesis (see, e.g., Nucleic Acid Research, Vol. 10, No. 20, p. 6487-6500, 1982, which is hereby incorporated by reference in its entirety). As used herein, the term "one or more amino acids" is intended to mean a possible number of amino acids which may be deleted, substituted, inserted and/or added by site-directed mutagenesis.

Site-directed mutagenesis may be accomplished, for example, as follows using a synthetic oligonucleotide primer that is complementary to single-stranded phage DNA to be mutated, except for having a specific mismatch (i.e., a desired mutation). Namely, the above synthetic oligonucleotide is used as a primer to cause synthesis of a complementary strand by phages, and the resulting duplex DNA is then used to transform host cells. The transformed bacterial culture is plated on agar, whereby plaques are allowed to form from phage-containing single cells. As a result, in theory, 50% of new colonies contain phages with the mutation as a single strand, while the remaining 50% have the original sequence. At a temperature which allows hybridization with DNA completely identical to one having the above desired mutation, but not with DNA having the original strand, the resulting plaques are allowed to hybridize with a synthetic probe labeled by kinase treatment. Subsequently, plaques hybridized with the probe are picked up and cultured for collection of their DNA.

Techniques for allowing deletion, substitution, insertion and/or addition of one or more amino acids in the amino acid sequences of biologically active peptides such as enzymes while retaining their activity include site-specific mutagenesis mentioned above, as well as other techniques such as those for treating a gene with a mutagen, and those in which a gene is selectively cleaved to remove, substitute, insert or add a selected nucleotide or nucleotides, and then ligated.

The mutant protein of the present invention may also be a protein having β-galactoside-α2,3-sialyltransferase activity, which is encoded by a nucleic acid comprising a nucleotide sequence hybridizable under stringent conditions or highly stringent conditions with the complementary strand of a nucleotide sequence selected from the group consisting of SEQ ID NO: 1, nucleotides 64-1230 of SEQ ID NO: 1, SEQ ID NO: 28, nucleotides 73-1230 of SEQ ID NO: 28, SEQ ID NO: 30, and nucleotides 67-1209 of SEQ ID NO: 30.

Stringent hybridization conditions for this purpose include, but are not limited to, hybridization at 55° C. in 0.5 M sodium phosphate pH 7.2, 1 mM EDTA, 7% SDS, 1% BSA, followed by washing twice at 55° C. for 15 minutes in 40 mM sodium phosphate buffer pH 7.2, 1 mM EDTA, 5% SDS, 0.5% BSA and twice at 55° C. for 15 minutes in 40 mM sodium phosphate buffer pH 7.2, 1 mM EDTA, 1% SDS, or alternatively, hybridization at 42° C. in 30% deionized formamide, 0.6 M NaCl, 40 mM sodium phosphate pH 7.4, 2.5 mM EDTA, 1% SDS, followed by washing twice at room temperature for 10 minutes in 2×SSC, 0.1% SDS and further at 55° C. for 1 hour in the same buffer, as described in, e.g., Molecular Cloning: A Laboratory Manual, second edition, vol. 1, pp. 1.101-104, Cold Spring Harbor Laboratory Press (1989) (which is hereby incorporated by reference in its entirety). Likewise, hybridization under highly stringent conditions includes, for example, hybridization at 65° C. in 0.5 M sodium phosphate pH 7.2, 1 mM EDTA, 7% SDS, 1% BSA, followed by washing at 65° C. in 40 mM sodium phosphate buffer pH 7.2, 1 mM EDTA, 5% SDS, 0.5% BSA and at 65°

C. in 40 mM sodium phosphate buffer pH 7.2, 1 mM EDTA, 1% SDS, as described in, e.g., Molecular Cloning (supra).

The mutant protein of the present invention may further be a protein having (β-galactoside-α2,3-sialyltransferase activity, which comprises an amino acid sequence sharing an amino acid homology of at least 60% or more, preferably 65% or more, 70% or more, 75% or more, 80% or more, 85% or more, 90% or more, 95% or more, 98% or more, or 99% or more, and more preferably 99.5% or more with an amino acid sequence selected from the group consisting of SEQ ID NO: 2, amino acids 22-409 of SEQ ID NO: 2, SEQ ID NO: 29, amino acids 25-409 of SEQ ID NO: 29, SEQ ID NO: 31, and amino acids 23-402 of SEQ ID NO: 31.

Alternatively, the mutant protein of the present invention may be a protein having β-galactoside-α2,3-sialyltransferase activity, which is encoded by a nucleic acid sharing a homology of at least 60% or more, preferably 65% or more, 70% or more, 75% or more, 80% or more, 85% or more, 90% or more, 95% or more, 98% or more, or 99% or more, and more preferably 99.5% or more with a nucleotide sequence selected from the group consisting of SEQ ID NO: 1, nucleotides 64-1230 of SEQ ID NO: 1, SEQ ID NO: 28, nucleotides 73-1230 of SEQ ID NO: 28, SEQ ID NO: 30, and nucleotides 67-1209 of SEQ ID NO: 30.

The percent homology between amino acid sequences or between nucleic acid and nucleotide sequence may be determined by visual inspection and mathematical calculation. For example, the percent homology of two amino acid sequences may be determined by comparing their sequence information using a program such as genetic information processing software GENETYX Ver. 7 (Genetyx Corporation, Japan) or using an algorithm such as FASTA or BLAST.

Sialyltransferase activity may be measured by known procedures, e.g., those described in J. Biochem., 120, 104-110 (1996) (which is hereby incorporated by reference in its entirety). For example, the enzyme activity can be evaluated by effecting an enzymatic reaction using CMP-NeuAc (N-acetylneuraminic acid) as a glycosyl donor substrate and lactose as a glycosyl acceptor substrate, followed by evaluating the amount of the reaction product sialyllactose.

Determination of the binding mode of sialic acid transferred to a glycosyl acceptor substrate may be accomplished by using, but not limited to, any procedure known to those skilled in the art, such as those using a pyridylaminated sugar chain or reaction product analysis by nuclear magnetic resonance spectrometry (NMR). Procedures using a pyridylaminated sugar chain comprise effecting an enzymatic reaction using a pyridylaminated sugar chain as a glycosyl acceptor substrate. More specifically, an enzymatic reaction is effected using pyridylaminated lactose (Galβ1-4Glc-PA, Takara Bio Inc., Japan) as a glycosyl acceptor substrate and CMP-NeuAc as a glycosyl donor substrate, and the reaction product is subjected to high performance liquid chromatography (HPLC) analysis. From the retention time of the reaction product, the position at which sialic acid was transferred is identified.

In an embodiment of the present invention, the enzyme of the present invention is an enzyme derived from microorganisms belonging to the Vibrionaceae, preferably derived from microorganisms belonging to *Vibrio* spp., or alternatively, preferably derived from microorganisms belonging to *Photobacterium* spp., and more preferably derived from microorganisms belonging to *Photobacterium phosphoreum*.

As to enzymological properties as well as physical and chemical properties, the β-galactoside-α2,3-sialyltransferase of the present invention is not only characterized by having β-galactoside-α2,3-sialyltransferase activity as defined above, but also has additional properties including, but not limited to: an optimum pH ranging from 5 to 11, 5 to 10, 5 to 9, or 5 to 7; an optimum temperature of 5° C. to 35° C., 10° C. to 35° C., 20° C. to 35° C., or 20° C. to 30° C.; and a molecular weight of about 42,000±3,000 Da, as measured by SDS-PAGE analysis.

Nucleic Acid Encoding β-galactoside-α2,3-sialyltransferase

The present invention provides a nucleic acid encoding β-galactoside-α2,3-sialyltransferase.

The nucleic acid of the present invention is a nucleic acid encoding a protein comprising an amino acid sequence selected from the group consisting of SEQ ID NO: 2, amino acids 22-409 of SEQ ID NO: 2, SEQ ID NO: 29, amino acids 25-409 of SEQ ID NO: 29, SEQ ID NO: 31, and amino acids 23-402 of SEQ ID NO: 31. Alternatively, the nucleic acid of the present invention is a nucleic acid comprising a nucleotide sequence selected from the group consisting of SEQ ID NO: 1, nucleotides 64-1230 of SEQ ID NO: 1, SEQ ID NO: 28, nucleotides 73-1230 of SEQ ID NO: 28, SEQ ID NO: 30, and nucleotides 67-1209 of SEQ ID NO: 30.

The nucleic acid of the present invention may be a mutant of the above nucleic acid as long as it is a nucleic acid encoding a protein having β-galactoside-α2,3-sialyltransferase activity. Such a nucleic acid also falls within the scope of the nucleic acid of the present invention encoding β-galactoside-α2,3-sialyltransferase.

Such a nucleic acid mutant is a nucleic acid encoding a protein having β-galactoside-α2,3-sialyltransferase activity, wherein the protein comprises an amino acid sequence comprising deletion, substitution, insertion and/or addition of one or more amino acids in an amino acid sequence selected from the group consisting of SEQ ID NO: 2, amino acids 22-409 of SEQ ID NO: 2, SEQ ID NO: 29, amino acids 25-409 of SEQ ID NO: 29, SEQ ID NO: 31, and amino acids 23-402 of SEQ ID NO: 31.

Such a nucleic acid mutant is also a nucleic acid encoding a protein having β-galactoside-α2,3-sialyltransferase activity, wherein the nucleic acid comprises a nucleotide sequence hybridizable under stringent conditions or highly stringent conditions with the complementary strand of a nucleotide sequence selected from the group consisting of SEQ ID NO: 1, nucleotides 64-1230 of SEQ ID NO: 1, SEQ ID NO: 28, nucleotides 73-1230 of SEQ ID NO: 28, SEQ ID NO: 30, and nucleotides 67-1209 of SEQ ID NO: 30. In this case, stringent conditions or highly stringent conditions are as defined above.

Such a nucleic acid mutant is also a nucleic acid encoding a protein having β-galactoside-α2,3-sialyltransferase activity, wherein the nucleic acid shares a homology of at least 60% or more, preferably 65% or more, 70% or more, 75% or more, 80% or more, 85% or more, 90% or more, 95% or more, 98% or more, or 99% or more, and more preferably 99.5% or more with a nucleotide sequence selected from the group consisting of SEQ ID NO: 1, nucleotides 64-1230 of SEQ ID NO: 1, SEQ ID NO: 28, nucleotides 73-1230 of SEQ ID NO: 28, SEQ ID NO: 30, and nucleotides 67-1209 of SEQ ID NO: 30. In this case, the homology between nucleic acid and nucleotide sequence may be determined as described above.

Such a nucleic acid mutant is further a nucleic acid encoding a protein having β-galactoside-α2,3-sialyltransferase activity, wherein the protein comprises an amino acid sequence sharing a homology of at least 60% or more, preferably 65% or more, 70% or more, 75% or more, 80% or more, 85% or more, 90% or more, 95% or more, 98% or more, or 99% or more, and more preferably 99.5% or more with an amino acid sequence selected from the group consisting of SEQ ID NO: 2, amino acids 22-409 of SEQ ID NO: 2, SEQ ID NO: 29, amino acids 25-409 of SEQ ID NO: 29, SEQ ID NO: 31, and amino acids 23-402 of SEQ ID NO: 31. In this case, the homology between amino acid sequences can be determined as described above.

Microorganisms Expressing β-galactoside-α2,3-sialyltransferase

The inventors of the present invention have found that microorganisms belonging to the Vibrionaceae express a novel β-galactoside-α2,3-sialyltransferase. Thus, the present invention provides microorganisms expressing β-galactoside-α2,3-sialyltransferase. The microorganisms of the present invention are those belonging to the Vibrionaceae and having the ability to produce β-galactoside-α2,3-sialyltransferase, preferably those belonging to *Vibrio* spp., or alternatively, preferably those belonging to *Photobacterium* spp., more preferably those belonging to *Photobacterium phosphoreum*. Examples of microorganisms belonging to the Vibrionaceae having the ability to produce β-galactoside-α2,3-sialyltransferase include *Photobacterium phosphoreum* strain JT-ISH-467 (Accession No. NITE BP-88), *Photobacterium* sp. strain JT-ISH-224 (Accession No. NITE BP-87), and *Vibrio* sp. strain JT-FAJ-16 (Accession No. NITE BP-98). It should be noted that the above microorganisms of the Vibrionaceae are marine bacteria, which are separated from sea water or marine products such as fish and shellfish. For example, the strains of the present invention were separated from squid in Ishikawa prefecture for *Photobacterium phosphoreum* strain JT-ISH-467, from barracuda in Ishikawa prefecture for *Photobacterium* sp. strain JT-ISH-224, and from horse mackerel in Fukuoka prefecture for *Vibrio* sp. strain JT-FAJ-16.

The microorganisms of the present invention can be separated using screening procedures as shown below, by way of example. Sea water, sea sand, sea mud or a marine product is used as a microorganism source. Sea water, sea sand and sea mud may be used directly or further diluted with sterilized sea water for use as an inoculation source. In the case of small marine animals, their surface slime or the like is collected by scrubbing with a loop and is then used as an inoculation source; or alternatively, their internal organs are homogenized in sterilized sea water and the resulting fluid is used as an inoculum. These inocula are applied onto agar plates such as marine broth agar 2216 medium (Becton Dickinson) or sodium chloride-supplemented nutrient agar medium (Becton Dickinson) to obtain marine microorganisms growing under various temperature conditions. After the resulting microorganisms have been pure-cultured in a routine manner, each microorganism is cultured using a liquid medium such as marine broth 2216 medium (Becton Dickinson) or sodium chloride-supplemented nutrient broth medium (Becton Dickinson). After the microorganisms are fully grown, the cells are collected by centrifugation from each culture solution. To the collected cells, 20 mM cacodylate buffer (pH 6.0) containing 0.2% Triton X-100 (Kanto Kagaku, Japan) is added, and the cells are suspended therein. This cell suspension is ultrasonicated under ice cooling to homogenize the cells. This cell homogenate is used as an enzyme solution and measured for its sialyltransferase activity in a routine manner, to thereby obtain a strain having sialyltransferase activity.

The above screening procedures were also used for obtaining the strains of the present invention, i.e., *Photobacterium phosphoreum* strain JT-ISH-467, *Photobacterium* sp. strain JT-ISH-224 and *Vibrio* sp. strain JT-FAJ-16. Their microbiological properties as well as physiological and biochemical properties will be detailed in Example 1, along with species identification based on nucleotide sequence analysis of the 16 S rRNA gene.

*Photobacterium phosphoreum* strain JT-ISH-467 was deposited on Mar. 14, 2005 under NITE BP-88, *Photobacterium* sp. strain JT-ISH-224 on Mar. 11, 2005 under NITE BP-87, and *Vibrio* sp. strain JT-FAJ-16 on May 23, 2005 under NITE BP-98 with the National Institute of Technology and Evaluation, Patent Microorganisms Depositary (NPMD; 2-5-8 Kazusakamatari, Kisarazu, Chiba, Japan).

Method for Producing β-galactoside-α2,3-sialyltransferase (1) Method for Producing β-galactoside-α2,3-sialyltransferase by Culturing Microorganisms Expressing the Enzyme In an embodiment of the present invention, the β-galactoside-α2,3-sialyltransferase of the present invention is derived from microorganisms belonging to the Vibrionaceae, and is obtained as follows: a microorganism having the ability to produce 1-galactoside-α2,3-sialyltransferase is cultured in a medium and allowed to produce β-galactoside-α2,3-sialyltransferase, which is then collected.

Microorganisms used for this purpose are not limited in any way as long as they belong to the Vibrionaceae and have the ability to produce β-galactoside-α2,3-sialyltransferase. Among microorganisms of the Vibrionaceae, preferred are those belonging to *Vibrio* spp. or *Photobacterium* spp., and more preferred are those belonging to *Photobacterium phosphoreum*. Examples of microorganisms for use in the method of the present invention include *Photobacterium phosphoreum* strain JT-ISH-467 (Accession No. NITE BP-88), *Photobacterium* sp. strain JT-ISH-224 (Accession No. NITE BP-87) and *Vibrio* sp. strain JT-FAJ-16 (Accession No. NITE BP-98).

For use in culturing the above microorganisms, the culture medium contains ingredients available to these microorganisms, including a carbon source, a nitrogen source and minerals. Such a carbon source includes peptone, tryptone, casein lysate, meat extract and glucose, with peptone being preferred for use. As a nitrogen source, yeast extract is preferred for use. Salts include sodium chloride, iron citrate, magnesium chloride, sodium sulfate, calcium chloride, potassium chloride, sodium carbonate, sodium bicarbonate, potassium bromide, strontium chloride, sodium borate, sodium silicate, sodium fluoride, ammonium nitrate and disodium hydrogen phosphate, which are preferably used in combination as appropriate.

Alternatively, marine broth 2216 medium (Becton Dickinson) containing the above ingredients may be used. Further, artificial sea water containing the above salts in appropriate amounts may also be used, supplemented with peptone, yeast extract or the like. Culture conditions will somewhat vary depending on the medium composition and/or the type of strain. For example, in the case of culturing *Photobacterium phosphoreum* strain JT-ISH-467, the culture temperature is 10° C. to 28° C., preferably 20° C. to 25° C., and the culture period is 8 to 48 hours, preferably 16 to 24 hours.

Since a target enzyme exists within microbial cells, any of known cell homogenization techniques such as ultrasonic disruption, French press homogenization, glass bead homogenization or Dynomil homogenization can be performed to separate and purify the target enzyme from the resulting cell homogenate. In the method of the present invention, a preferred cell homogenization technique is ultrasonic disruption. For example, after centrifugation to remove solid matter from the cell homogenate, the resulting cell homogenate supernatant can be purified to give an electrophoretically single band, e.g., by column chromatography on a commercially available column such as an anion exchange column, a cation exchange column, a gel filtration column, a hydroxyapatite column, a CDP-hexanolamine agarose column, a CMP-hexanolamine agarose column and/or a hydrophobic column, as well as Native-PAGE, which are used in combination as appropriate.

It should be noted that although β-galactoside-α2,3-sialyltransferase may be completely purified, the 1-galactoside-α2,3-sialyltransferase of the present invention may be in either purified or partially purified form because it has sufficient activity even in partially purified form.

(2) Method for Producing Recombinant β-galactoside-α2,3-sialyltransferase

The present invention provides an expression vector carrying a nucleic acid encoding β-galactoside-α2,3-sialyltransferase, and a host cell containing the expression vector. Moreover, the present invention also provides a method for producing a recombinant β-galactoside-α2,3-sialyltransferase protein, which comprises culturing a host cell containing the expression vector under conditions suitable for recombinant protein expression, and collecting the expressed recombinant protein.

To produce the recombinant β-galactoside-α2,3-sialyltransferase protein of the present invention, an expression vector chosen depending on the host to be used is inserted with a nucleic acid sequence encoding β-galactoside-α2,3-sialyltransferase that is operably linked to a suitable transcription or translation regulatory nucleotide sequence derived from a gene of mammalian, microorganism, viral, insect or other origin. Examples of such a regulatory sequence include a transcription promoter, an operator or an enhancer, a mRNA ribosome binding site, as well as suitable sequences regulating the initiation and termination of transcription and translation.

Such a nucleic acid sequence encoding β-galactoside-α2,3-sialyltransferase to be inserted into the vector of the present invention may or may not comprise a leader sequence corresponding to nucleotides 1-63 of SEQ ID NO: 1, nucleotides 1-72 of SEQ ID NO: 28 or nucleotides 1-66 of SEQ ID NO: 30, which may be replaced by a leader sequence derived from other organisms. Leader sequence replacement enables the design of an expression system which allows secretion of the expressed protein into the extracellular environment of host cells.

Moreover, the recombinant β-galactoside-α2,3-sialyltransferase protein of the present invention may also be expressed as a fusion protein by inserting a vector with a nucleic acid designed such that a nucleic acid encoding a His tag, a FLAG™ tag, glutathione-S-transferase or the like is linked downstream of a nucleic acid encoding the enzyme. When the enzyme of the present invention is expressed as a fusion protein in this way, such a fusion protein can facilitate purification and detection of the enzyme.

Host cells suitable for protein expression of β-galactoside-α2,3-sialyltransferase include prokaryotic cells, yeast or higher eukaryotic cells. Suitable cloning and expression vectors for use in bacterial, fungal, yeast and mammalian host cells are described, for example, in Pouwels et al., Cloning Vectors: A Laboratory Manual, Elsevier, New York, (1985) (which is hereby incorporated by reference in its entirety).

Prokaryotic organisms include Gram-negative or Gram-positive bacteria such as E. coli or Bacillus subtilis. When a prokaryotic cell such as E. coli is used as a host, a β-galactoside-α2,3-sialyltransferase protein may be designed to have an N-terminal methionine residue for the purpose of facilitating recombinant polypeptide expression within prokaryotic cells. This N-terminal methionine may be cleaved from the expressed recombinant β-galactoside-α2,3-sialyltransferase protein.

Expression vectors for use in prokaryotic host cells generally contain one or more phenotype selectable marker genes. Such a phenotype selectable marker gene is, for example, a gene imparting antibiotic resistance or auxotrophy. Examples of expression vectors suitable for prokaryotic host cells include commercially available plasmids such as pBR322 (ATCC37017) or derivatives thereof. pBR322 contains genes for ampicillin and tetracycline resistance, and thereby facilitates identification of transformed cells. DNA sequences of a suitable promoter and a nucleic acid encoding. β-galactoside-α2,3-sialyltransferase are inserted into this pBR322 vector. Other commercially available vectors include, for example, pKK223-3 (Pharmacia Fine Chemicals, Uppsala, Sweden) and pGEM1 (Promega Biotech., Madison, Wis., United States).

Promoter sequences generally used in expression vectors for prokaryotic host cells include tac promoter, β-lactamase (penicillinase) promoter, and lactose promoter (Chang et al., Nature 275:615, 1978; and Goeddel et al., Nature 281:544, 1979, which are hereby incorporated by reference in their entirety).

Alternatively, a recombinant β-galactoside-α2,3-sialyltransferase protein may be expressed in yeast host cells, preferably using Saccharomyces (e.g., S. cerevisiae). Other genera of yeast, such as Pichia or Kluyveromyces, may also be used. Yeast vectors often contain an origin of replication sequence from 2μ yeast plasmid, an autonomously replicating sequence (ARS), a promoter region, sequences for polyadenylation, sequences for transcription termination, and a selectable marker gene. A yeast α-factor leader sequence can also be used to induce secretion of a recombinant β-galactoside-α2,3-sialyltransferase protein. There are also known other leader sequences that are suitable for facilitating recombinant polypeptide secretion from yeast hosts. Procedures for yeast transformation are described, for example, in Hinnen et al., Proc. Natl. Acad. Sci. USA, 75: 1929-1933, 1978 (which is hereby incorporated by reference in its entirety).

Mammalian or insect host cell culture systems can also be used to express a recombinant β-galactoside-α2,3-sialyltransferase protein. Established cell lines of mammalian origin can also be used for this purpose. Transcription and translation control sequences for mammalian host cell expression vectors may be obtained from the viral genome. Promoter and enhancer sequences commonly used are derived from polyomavirus, adenovirus 2, etc. DNA sequences derived from the SV40 viral genome (e.g., SV40 origin, early and late promoters, enhancers, splice sites, polyadenylation sites) may also be used to provide other gene elements for expression of structural gene sequences in mammalian host cells. Vectors for use in mammalian host cells can be constructed, for example, by the method of Okayama and Berg (Mol. Cell. Biol., 3: 280, 1983, which is hereby incorporated by reference in its entirety).

One method of the present invention for producing a (β-galactoside-α2,3-sialyltransferase protein comprises culturing host cells transformed with an expression vector carrying a nucleic acid sequence encoding a β-galactoside-α2,3-sialyltransferase protein, under conditions allowing expression of the protein. Then, in a manner suitable for the expression system used, the (β-galactoside-α2,3-sialyltransferase protein is collected from the culture medium or cell extract.

Means for purifying a recombinant β-galactoside-α2,3-sialyltransferase protein are selected, as appropriate, depending on such factors as what type of host was used and whether the protein of the present invention is to be secreted into the culture medium. For example, means for purifying a recombinant β-galactoside-α2,3-sialyltransferase protein include column chromatography on an anion exchange column, a cation exchange column, a gel filtration column, a hydroxyapatite column, a CDP-hexanolamine agarose column, a CMP-hexanolamine agarose column and/or a hydrophobic column, as well as Native-PAGE or combinations thereof. Alternatively, when a recombinant β-galactoside-α2,3-sialyltransferase is expressed in a form fused with a tag or the like for easy purification, affinity chromatographic techniques may be used for purification. For example, when a histidine tag, a FLAG™ tag or glutathione-S-transferase (GST) is fused, purification can be accomplished by affinity chromatography using a Ni-NTA (nitrilotriacetic acid) column, an anti-FLAG antibody-bound column or a glutathione-bound column, respectively.

Although a recombinant β-galactoside-α2,3-sialyltransferase may be purified to give an electrophoretically single band, the β-galactoside-2,3-sialyltransferase of the present invention may be in either purified or partially purified form because it has sufficient activity even in partially purified form.

Antibody

The present invention provides an antibody against the β-galactoside-α2,3-sialyltransferase protein of the present invention. The antibody of the present invention may be prepared against the β-galactoside-α2,3-sialyltransferase protein of the present invention or a fragment thereof. A fragment of the f-β-galactoside-α2,3-sialyltransferase of the present invention used for this purpose is a fragment having a sequence comprising at least 6 amino acids, at least 10 amino acids, at least 20 amino acids or at least 30 amino acids of the amino acid sequence of the enzyme.

Such an antibody may be prepared by immunizing the f-β-galactoside-α2,3-sialyltransferase of the present invention or a fragment thereof into animals used for antibody preparation in the art including, but not limited to, mice, rats, rabbits, guinea pigs and goats. The antibody may be either polyclonal or monoclonal. The antibody can be prepared based on antibody preparation techniques well known to those skilled in the art.

The antibody of the present invention can be used for collecting the β-galactoside-α2,3-sialyltransferase protein of the present invention by affinity purification. The antibody of the present invention can also be used for detecting the β-galactoside-α2,3-sialyltransferase protein of the present invention in assays such as western blotting and ELISA.

Method for Preparing Sialylated Sugar Chain

In one embodiment, the present invention provides a method for preparing a sialylated sugar chain by using the sialyltransferase of the present invention. The method of the present invention is a method for preparing a sialylated sugar chain, which comprises:

(i) preparing a solution containing the β-galactoside-α2,3-sialyltransferase of the present invention, a glycosyl donor substrate and a glycosyl acceptor substrate;

(ii) causing sialic acid transfer reaction in the solution; and (iii) obtaining the generated sialylated sugar chain from the reaction solution.

As used herein, the term "sialylated sugar chain" is intended to mean a sugar chain having sialic acid. In the method of the present invention, sialic acid in a glycosyl donor substrate is transferred to a glycosyl acceptor substrate through sialic acid transfer reaction catalyzed by the enzyme of the present invention, whereby a sialylated sugar chain is obtained.

Glycosyl donor substrates available for use in the method of the present invention are not limited in any way as long as they are substrates capable of serving as glycosyl donors in sialic acid transfer reaction catalyzed by the sialyltransferase of the present invention. A preferred glycosyl donor substrate available for use in the method of the present invention is CMP-sialic acid, and more preferred is CMP-NeuAc.

Glycosyl acceptor substrates available for use in the method of the present invention include, but are not limited to, complex carbohydrate sugar chains or oligosaccharides having, e.g., a galactose residue, a glucose residue, a mannose residue, a fucose residue, an N-acetylglucosamine residue or an N-acetylgalactosamine residue, as well as monosaccharides such as galactose, glucose, mannose, fucose, N-acetylglucosamine or N-acetylgalactosamine. As used herein, the term "complex carbohydrate" is a generic name for carbohydrate-containing biomolecules, including glycoproteins, proteoglycans and glycolipids. As used herein, the term "complex carbohydrate sugar chain" is intended to mean either a complex carbohydrate per se (e.g., glycoprotein, proteoglycan, glycolipid) or a sugar chain moiety thereof. Likewise, the term "oligosaccharide" is intended to mean a sugar composed of two or more monosaccharides linked via glycosidic linkage(s). There is no particular limitation on the number of monosaccharides constituting an oligosaccharide. The reducing end of such a monosaccharide or oligosaccharide may be modified with an alkyl group, a pyridylamino group, benzoyl group, a benzyl group, a p-nitrophenyl group, a 4-methylumbelliferyl group, and so on.

In the method of the present invention, the solution containing the enzyme of the present invention, a glycosyl donor substrate and a glycosyl acceptor substrate is a buffer. Non-limiting examples include acetate buffer, cacodylate buffer, phosphate buffer, TAPS buffer, Bis-Tris buffer, Tris buffer, CHES buffer, CAPS buffer, MOPS buffer, MES buffer, ADA buffer, PIPES buffer, ACES buffer, MOPSO buffer and HEPES buffer. In the method of the present invention, the pH of the solution containing the enzyme of the present invention, a glycosyl donor substrate and a glycosyl acceptor substrate is not limited in any way as long as it is a pH at which the enzyme of the present invention has enzyme activity; and is preferably pH 5 to 11, pH 5 to 10, pH 5 to 9, or pH 5 to 7.

In the method of the present invention, the temperature for sialic acid transfer reaction is not limited in any way as long as it is a temperature at which the enzyme of the present invention has enzyme activity; and it preferably ranges from 5° C. to 35° C., 10° C. to 35° C., 20° C. to 35° C., or 20° C. to 30° C.

In the method of the present invention, the step of obtaining the generated sialylated sugar chain from the reaction solution may be accomplished by using procedures known to those skilled in the art for purifying complex carbohydrate sugar chains and/or oligosaccharides. Examples include, but are not limited to, chromatographic procedures such as reversed-phase chromatography, gel filtration chromatography, ion exchange chromatography, hydroxyapatite chromatography, affinity chromatography, lectin chromatography, activated carbon chromatography and silica gel chromatography, as well as other procedures such as sugar chain fractionation/concentration by means of an ultrafiltration, and sugar chain crystallization, or combinations thereof.

The enzyme of the present invention is capable of transferring sialic acid in α2,3 linkage to many types of glycosyl acceptor substrates, as shown in Examples 4, 11, 12 and 13 described later. The method of the present invention for preparing a sialylated sugar chain allows easy preparation of sugar chains which generally could not have been prepared by using known sialyltransferases with high substrate specificity. In particular, there is no enzyme known to have the ability to efficiently transfer sialic acid to a sugar such as α-galactopyranoside, α-glucopyranoside, α-mannopyranoside, α-fucosynopyranoside or β-fucosynopyranoside. Thus, the method of the present invention provides a method for easy preparation of sialylated sugar chains in which sialic acid is added to these sugars.

Advantages of the Invention

By providing a novel β-galactoside-α2,3-sialyltransferase and a nucleic acid encoding the same, the present invention makes a contribution in terms of providing a means for synthesizing and producing sugar chains, which are now being shown to have important functions in the body. In particular, sialic acid is often located at the non-reducing ends of complex carbohydrate sugar chains in the body and is a very important sugar in terms of sugar chain functions. Thus, sialyltransferase is one of the most in demand enzymes among glycosyltransferases, and the provision of the novel sialyltransferase of the present invention meets such a high demand.

BRIEF DESCRIPTION OF DRAWINGS

FIG. 1-2 shows the results of HPLC analysis in an experiment designed to confirm the enzyme activity of a recombinant β-galactoside-α2,3-sialyltransferase derived from the strain JT-ISH-467.

FIG. 1-3 shows the results of HPLC analysis obtained from a control experiment (i.e., reaction using a reaction solution free from CMP-sialic acid as a glycosyl donor) in an experiment designed to confirm the enzyme activity of a recombinant β-galactoside-α2,3-sialyltransferase derived from the strain JT-ISH-467.

FIG. 2 shows amino acid sequence alignment of α2,3-sialyltransferases derived from *Photobacterium phosphoreum* strain JT-ISH-467, *Photobacterium* sp. strain JT-ISH-224 and *Vibrio* sp. strain JT-FAJ-16 (SEQ ID NOs: 2, 29 and 31, respectively), α2,6-sialyltransferase (JC5898) from *Photobacterium damselae* (SEQ ID NO: 46), as well as a putative protein PM0188 (AAK02272) of *Pasteurella multocida* subsp. *multocida* strain Pm70 (SEQ ID NO: 47). For α2,3-sialyltransferase derived from the strain JT-ISH-467, underlined regions represent amino acid sequences determined from the purified protein.

FIG. 3-1 is a graph showing the effect of reaction pH on the enzyme activity of β-galactoside-α2,3-sialyltransferase produced by the strain JT-ISH-467. In the graph, plots indicated by solid squares, solid circles, solid triangles, solid diamonds, open squares and open circles represent the results measured in acetate buffer, cacodylate buffer, phosphate buffer, TAPS buffer, CHES buffer and CAPS buffer, respectively.

FIG. 3-2 presents graphs showing the effect of reaction pH on the enzyme activity of recombinant β-galactoside-α2,3-sialyltransferases. FIGS. 3-2a, 3-2b and 3-2c are graphs showing the results obtained for recombinant β-galactoside-α2,3-sialyltransferases derived from the strains JT-ISH-467, JT-ISH-224 and JT-FAJ-16, respectively. In the graphs, plots indicated by solid squares, solid circles, solid triangles, solid diamonds, open squares and open circles represent the results measured in acetate buffer, cacodylate buffer, phosphate buffer, TAPS buffer, CHES buffer and CAPS buffer, respectively.

FIG. 4-1 is a graph showing the effect of reaction temperature on the enzyme activity of β-galactoside-α2,3-sialyltransferase produced by the strain JT-ISH-467.

FIG. 4-2 presents graphs showing the effect of reaction temperature on the enzyme activity of recombinant β-galactoside-α2,3-sialyltransferases. FIGS. 4-2a, 4-2b and 4-2c are graphs showing the results obtained for recombinant β-galactoside-α2,3-sialyltransferases derived from the strains JT-ISH-467, JT-ISH-224 and JT-FAJ-16, respectively.

Figure 1:
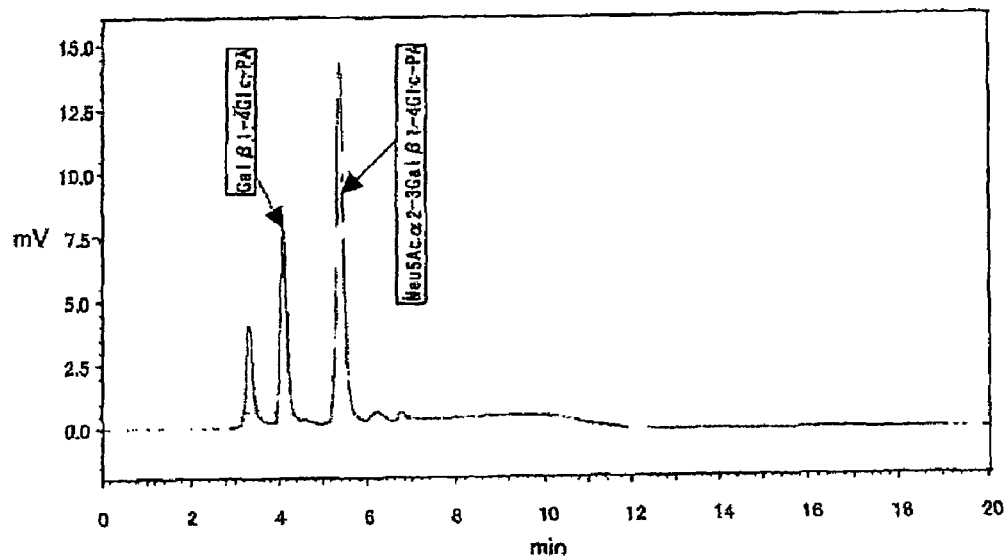
FIG. 1-1 shows the results of HPLC analysis obtained for standards (i.e., a mixture of deactivated crude enzyme solution, pyridylaminated lactose and pyridylaminated α2,3-sialyllactose (pyridylaminated 3'-sialyllactose)) in an experiment designed to confirm the enzyme activity of a recombinant (β-galactoside-α2,3-sialyltransferase derived from the strain JT-ISH-467.

The present invention will now be described in more detail by way of the following examples, which are not intended to limit the technical scope of the invention.

EXAMPLES

Example 1

Screening and Strain Identification of Microorganisms Expressing β-galactoside-α2,3-sialyltransferase Sea water, sea sand, sea mud or a marine product was used as an inoculum. This inoculum was applied onto agar plates containing marine broth agar 2216 medium (Becton Dickinson) to obtain microorganisms growing at 15° C., 25° C. or 30° C. After the resulting microorganisms were pure-cultured in a routine manner, each microorganism was cultured using a liquid medium composed of marine broth 2216 medium (Becton Dickinson). After the microorganisms were fully grown, the cells were collected from each culture solution by centrifugation. To the collected cells, 20 mM cacodylate buffer (pH 6.0) containing 0.2% Triton X-100 (Kanto Kagaku, Japan) was added, and the cells were suspended therein. This cell suspension was ultrasonicated under ice cooling to homogenize the cells. This cell homogenate was used as an enzyme solution and measured for its sialyltransferase activity, thus obtaining strains having sialyltransferase activity, i.e., JT-ISH-467, JT-ISH-224 and JT-FAJ-16. Incidentally, the strain JT-ISH-467 was obtained from the epidermis of Japanese common squid, the strain JT-ISH-224 was obtained from the internal organs of barracuda, and the strain JT-FAJ-16 was obtained from the internal organs of horse mackerel.

Sialyltransferase activity was measured as described in J. Biochem., 120, pp. 104-110 (1996) (which is hereby incorporated by reference in its entirety). More specifically, the enzymatic reaction was accomplished by using CMP-NeuAc (70 nmol, containing 25000 cpm CMP-NeuAc in which NeuAc was labeled with $^{14}C$, 356 cpm/nmol; NeuAc represents N-acetylneuraminic acid) as a glycosyl donor substrate, lactose (1.25 μmol) as a glycosyl acceptor substrate, NaCl added to give a concentration of 0.5 M, and the enzyme-containing reaction solution (30 μl) prepared as described above. The enzymatic reaction was carried out at 25° C. for 10 to 30 minutes. After completion of the reaction, 1.97 ml of 5 mM phosphate buffer (pH 6.8) was added to the reaction solution, which was then applied to a Dowex 1×8 ($PO_4^{3-}$ form, 0.2×2 cm, BIO-RAD) column. The radioactivity was measured for the reaction product, i.e., sialyllactose contained in the eluate (0 to 2 ml) from this column to calculate the enzyme activity.

(i) Strain JT-ISH-467

The resulting strain JT-ISH-467 was found to have the following properties:

(Microbiological Properties)

(1) The cells are in bacillary form and have a size of 0.7 to 0.8 μm×1.5 to 2.0 μm.
(2) Motility: −
(3) Gram staining: −
(4) Spore: −

(Physiological and Biochemical Properties)

(1) Growth temperature: + at 4° C., + at 25° C., − at 30° C.
(2) Colony color: not producing characteristic colony pigment
(3) O/F test: +/−
(4) Catalase test: −
(5) Oxidase test: +
(6) Acid production from glucose: −
(7) Gas generation from glucose: −
(8) Photogenesis: +
(9) Reduction of nitrate: +
(10) Indole formation: +
(11) Glucose acidification: −
(12) Arginine dihydrolase: +
(13) Urease: −
(14) Esculin hydrolysis: −
(15) Gelatin hydrolysis: −
(16) β-Galactosidase: +
(17) Glucose assimilation: −
(18) L-Arabinose assimilation: −
(19) D-Mannose assimilation: −
(20) D-Mannitol assimilation: −
(21) N-Acetyl-D-glucosamine assimilation: −
(22) Maltose assimilation: −
(23) Potassium gluconate assimilation: −
(24) n-Capric acid assimilation: −
(25) Adipic acid assimilation: −
(26) dl-Malic acid assimilation: −
(27) Sodium citrate assimilation: −
(28) Phenyl acetate assimilation: −
(29) Cytochrome oxidase: +
(30) GC content of DNA isolated from bacterial cells (mol %): 39.7%

(Nucleotide Sequence Analysis of 16 S rRNA Gene and Species Identification Based on DNA-DNA Hybridization)

The genomic DNA extracted from the strain JT-ISH-467 in a routine manner was used as a template for PCR to amplify the entire nucleotide sequence of the 16 S rRNA gene, thereby determining its nucleotide sequence. The nucleotide sequence is shown in SEQ ID NO: 3. This nucleotide sequence showed homology as high as 100% with the nucleotide sequence of the 16 S rRNA gene in *Photobacterium phosphoreum* the type strain ATCC11040. This result indicated that the JT-ISH-467 strain belongs to the genus *Photobacterium*. However, since the 16S rRNA gene is merely a part of the whole bacterial genome, identification analysis based on the nucleotide sequence of the 16 S rRNA gene is recognized as producing a very large error for the distance between very closely related organisms at species level. For this reason, DNA-DNA hybridization testing, which is commonly used for quantitative evaluation of the relatedness among strains within the same genus, was used for species determination. Total DNAs of the strain JT-ISH-467 and *Photobacterium phosphoreum* the type strain NCIMB1282 (which is the same strain as ATCC11040) were extracted and tested. As a result, a homology level (DNA-DNA relatedness) as high as 84.7% was obtained. Since DNA-DNA homology between the same species is usually 60% or more, the JT-ISH-467 strain was identified to be *Photobacterium phosphoreum*. DNA-DNA hybridization testing was accomplished by photobiotin labeling using microplates, as described in "Experimental Procedures for Classification and Identification of Microorganisms" (edited by Kenichiro Suzuki, Akira Hiraishi and Akira Yokota, Springer-Verlag, Tokyo, September 2001, hereby incorporated by reference in its entirety).

(ii) Strain JT-ISH-224

The resulting strain JT-ISH-224 was found to have the following properties:

(Microbiological Properties)

(1) The cells are in bacillary form and have a size of 0.7 to 0.8 μm×1.0 to 1.5 μm.
(2) Motility: +
(3) Gram staining: −
(4) Spore: −

(Physiological and Biochemical Properties)

(1) Growth temperature: − at 4° C., + at 25° C., + at 30° C., − at 37° C.
(2) Colony color: not producing characteristic colony pigment
(3) O/F test: +/−
(4) Catalase test: +
(5) Oxidase test: +
(6) Acid production from glucose: +
(7) Gas generation from glucose: +
(8) Photogenesis: −
(9) Reduction of nitrate: +
(10) Indole formation: +
(11) Glucose acidification: −
(12) Arginine dihydrolase: +
(13) Urease: −
(14) Esculin hydrolysis: −
(15) Gelatin hydrolysis: −
(16) β-Galactosidase: +
(17) Glucose assimilation: −
(18) L-Arabinose assimilation: −
(19) D-Mannose assimilation: −
(20) D-Mannitol assimilation: −
(21) N-Acetyl-D-glucosamine assimilation: −
(22) Maltose assimilation: −
(23) Potassium gluconate assimilation: −
(24) n-Capric acid assimilation: −
(25) Adipic acid assimilation: −
(26) dl-Malic acid assimilation: −
(27) Sodium citrate assimilation: −
(28) Phenyl acetate assimilation: −
(29) Cytochrome oxidase: +
(30) O/129 sensitivity: 10 μg−, 15 μg+
(31) GC content of DNA isolated from bacterial cells (mol %): 39.4%

(Nucleotide Sequence Analysis of 16 S rRNA Gene)

The genomic DNA extracted from the strain JT-ISH-224 in a routine manner was used as a template for PCR to amplify the entire nucleotide sequence of the 16 S rRNA gene, thereby determining its nucleotide sequence. The nucleotide sequence is shown in SEQ ID NO: 32.

The strain JT-ISH-224 was shown to belong to the Vibrionaceae, based on its morphological observations including growth on marine agar, bacillary form, Gram staining, fermentative glucose degradation and O/129 sensitivity, along with the results from the physiological and biochemical property tests. Moreover, the DNA nucleotide sequence of the 16S rRNA gene in the JT-ISH-224 strain was found to share the highest homology (99.2%) with the sequence of the 16 S rRNA gene in *Photobacterium phosphoreum* the type strain ATCC11040, and the second highest homology (99.1%) with the sequence of the 16 S rRNA gene in *Photobacterium iliopiscarium* the type strain ATCC51760. These results indicated that the JT-ISH-224 strain is a microorganism belonging to the genus *Photobacterium* (*Photobacterium* sp.).

(iii) Strain JT-FAJ-16

The resulting JT-FAJ-16 strain was found to have the following properties:

(Microbiological Properties)

(1) The cells are in bacillary form and have a size of 0.7 to 0.8 μm×1.2 to 1.5 μm.
(2) Motility: −
(3) Gram staining: −
(4) Spore: −

(Physiological and Biochemical Properties)

(1) Growth temperature: +w at 4° C., + at 25° C., + at 30° C., + at 37° C.
(2) Colony color: light-yellow to cream
(3) O/F test: +/+
(4) Catalase test: +
(5) Oxidase test: +
(6) Acid production from glucose: +
(7) Gas generation from glucose: −
(8) Reduction of nitrate: +
(9) Indole formation: −
(10) Glucose acidification: +
(11) Arginine dihydrolase: −
(12) Urease: −
(13) Esculin hydrolysis: +
(14) Gelatin hydrolysis: −
(15) β-Galactosidase: +
(16) Glucose assimilation: −
(17) L-Arabinose assimilation: −
(18) D-Mannose assimilation: −
(19) D-Mannitol assimilation: −
(20) N-Acetyl-D-glucosamine assimilation: −
(21) Maltose assimilation: −
(22) Potassium gluconate assimilation: −
(23) n-Capric acid assimilation: −
(24) Adipic acid assimilation:
(25) dl-Malic acid assimilation: −
(26) Sodium citrate assimilation: −
(27) Phenyl acetate assimilation: −
(28) Cytochrome oxidase: +
(29) O/129 sensitivity: −
(30) Mannitol fermentation: +
(31) Inositol fermentation: +
(32) Arabinose fermentation: +
(33) Rhamnose fermentation: −
(34) Saccharose fermentation: −
(35) Growht in NaCl: 3% NaCl+, 4% NaCl+, 6% NaCl+
(36) Starch hydrolysis: −
(37) Tween 80 decomposition: −
(38) $H_2S$ formation: −
(39) Acetoin formation (VP test): −

(Nucleotide Sequence Analysis of 16 S rRNA Gene)

The genomic DNA extracted from the strain JT-FAJ-16 in a routine manner was used as a template for PCR to amplify the entire nucleotide sequence of the 16 S rRNA gene, thereby determining its nucleotide sequence. The nucleotide sequence is shown in SEQ ID NO: 33.

The strain JT-FAJ-16 was shown to belong to the Vibrionaceae, based on its morphological observations including growth on marine agar, bacillary form, Gram staining, fermentative glucose degradation and O/129 sensitivity, along with the results from the physiological and biochemical property tests. Moreover, the DNA nucleotide sequence of the 16 S rRNA gene in the JT-FAJ-16 strain was found to share the highest homology (99.5%) with the sequence of the 16 S rRNA gene in a *Vibrio rumoiensis* the type strain. These' results indicated that the JT-FAJ-16 strain is a microorganism belonging to the genus *Vibrio* (*Vibrio* sp.).

Example 2

Extraction and Purification of β-galactoside-α2,3-sialyltransferase from *Photobacterium phosphoreum* JT-ISH-467

From colonies of *Photobacterium phosphoreum* strain JT ISH-467 subcultured on marine agar 2216 plates, the cells were collected with a loop, inoculated into 10 ml marine broth 2216 liquid medium and cultured with shaking at 25° C. at 180 rpm for 8 hours.

Main culturing was accomplished in the following manner. Marine broth 2216 medium (300 ml) supplemented with 20 g/L Bacto Peptone and 4 g/L Bacto Yeast Extract was charged into a 1000 ml baffle flask and sterilized in an autoclave (121° C., 15 minutes). The same medium was prepared in 36 flasks (10.8 L in total). Each flask was inoculated with the above culture solution (10 ml) and cultured with shaking at 25° C. at 180 rpm for 24 hours. The cultured medium was centrifuged to collect the cells (about 60 g on a wet weight basis).

The cells were suspended in 990 ml of 20 mM cacodylate buffer (pH 6.0) containing 0.2% Triton X-100 and 3 M sodium chloride, and ultrasonically homogenized under ice cooling. The cell homogenate was centrifuged at 4° C. at 100,000×g for 1 hour to obtain the supernatant. The resulting supernatant was introduced into a dialysis membrane tube and dialyzed at 4° C. against 20 mM cacodylate buffer (pH 6.0) containing 0.2% Triton X-100 until sodium chloride was reduced to around 20 mM. Since precipitates were generated in the solution after dialysis, centrifugation was performed at 4° C. at 100,000×g for 1 hour to remove the precipitates.

This crude enzyme solution was loaded to an anion exchange column called HiPrep 16/10 DEAE FF (Amersham Biosciences), which had been equilibrated with 20 mM cacodylate buffer (pH 6.0) containing 0.2% Triton X-100 (surfactant). The column was eluted with a linear gradient up to 1 M sodium chloride in 20 mM cacodylate buffer (pH 6.0) containing 0.2% Triton X-100 to thereby collect an enzymatically active fraction eluted at around 0.25 M sodium chloride concentration.

The collected fraction was diluted with 20 mM phosphate buffer (pH 6.0) and loaded to hydroxyapatite (Bio-Rad) which had been equilibrated with 20 mM phosphate buffer (pH 6.0) containing 0.2% Triton X-100, followed by elution with a linear gradient from 20 mM phosphate buffer (pH 6.0) containing 0.2% Triton X-100 to 500 mM phosphate buffer (pH 6.0) containing 0.2% Triton X-100 to thereby collect an enzymatically active fraction eluted at around 125 mM phosphate buffer concentration.

This fraction was loaded to a MonoQ 5/50 GL (Amersham Biosciences) anion exchange column. The column was eluted with a linear gradient up to 1 M sodium chloride in 20 mM cacodylate buffer (pH 6.0) containing 0.2% Triton X-100 to thereby collect an enzymatically active fraction eluted at around 300 mM sodium chloride concentration.

This fraction was diluted 10-fold with 20 mM cacodylate buffer (pH 7.0) containing 0.2% Triton X-100 and loaded to a MonoQ 5/50 GL (Pharmacia) anion exchange column. The column was eluted with a linear gradient up to 1 M sodium chloride in 20 mM cacodylate buffer (pH 7.0) containing 0.2% Triton X-100 to thereby collect an enzymatically active fraction eluted at around 300 mM sodium chloride concentration.

This fraction was diluted 2-fold with 20 mM cacodylate buffer (pH 7.0) containing 0.2% Triton X-100 and 0.2 M sodium chloride, and then fractionated on a HiLoad 16/60 Superdex 200 prep grade (Amersham Biosciences) gel filtration column. The column was eluted with 20 mM cacodylate buffer (pH 7.0) containing 0.2% Triton X-100 and 0.2 M sodium chloride.

The active fraction was electrophoresed on an SDS-polyacrylamide gel (the concentration of the acrylamide gel: 12.5%), indicating that the target enzyme showed a single band with a molecular weight of about 39,000. The specific activity of this fraction was about 350-fold higher than that of the cell homogenate (Table 1).

As to purification of α2,3-sialyltransferase derived from the JT-ISH-467 strain from a crude enzyme solution, Table 1 shows the enzyme activity of the sample after each of the purification steps mentioned, above. The enzyme activity was measured by the method reported in J. Biochem. 120, pp. 104-110 (1996), in the same manner as described in Example 1. For protein quantification, a Coomassie Protein Assay Reagent (PIERCE) was used according to the instruction manual attached thereto. One enzyme unit (1 U) was defined as the amount of enzyme required to transfer 1 micromole of sialic acid per minute.

TABLE 1

Purification of α2,3-sialyltransferase derived from strain JT-ISH-467 from crude enzyme solution

| Purification step | Volume (ml) | Total protein (mg) | Total activity (U) | Specific activity (U/mg) | Yield (%) | Purification degree (fold) |
|---|---|---|---|---|---|---|
| Crude enzyme solution | 950 | 2,930 | 21.3 | 0.0073 | 100 | 1 |
| DEAE | 90 | 468 | 4.0 | 0.0085 | 19 | 1.2 |
| Hydroxyapatite | 85 | 129 | 2.7 | 0.0212 | 13 | 2.9 |
| Mono Q (pH 6) | 1 | 1.64 | 0.073 | 0.0448 | 0.34 | 6.2 |
| Mono Q (pH 7) | 0.5 | 0.138 | 0.023 | 0.164 | 0.11 | 22.5 |
| Superdex 200 | 1.5 | 0.0047 | 0.012 | 2.50 | 0.044 | 343.6 |

Example 3

Determination of Binding Mode of Sialic Acid Using Pyridylaminated Sugar Chain

Using the enzyme obtained in Example 2, the enzymatic reaction was carried out using a pyridylaminated sugar chain as a glycosyl acceptor substrate. The pyridylaminated sugar chain used for analysis was pyridylaminated lactose (Galβ1-4Glc-PA, Takara Bio Inc., Japan). The glycosyl acceptor substrate, CMP-NeuAc and the enzyme were dissolved at 2.0 µM, 5.7 µM and 20 mU/ml, respectively, in 25 µl of 20 mM cacodylate buffer (pH 6.0), and then reacted at 25° C. for 3 hours. After the reaction, the reaction solution was treated at 100° C. for 2 minutes to inactivate the enzyme, followed by HPLC to analyze the reaction product.

The HPLC system used was Shimadzu LC10A (Shimadzu Corporation, Japan) and the analytical column used was Takara PALPAK Type R (Takara Bio Inc., Japan). The column which had been equilibrated with 100 mM acetate-triethylamine (pH 5.0) containing 0.15% N-butanol was injected with the reaction solution diluted with Eluent A (100 mM acetate-triethylamine, pH 5.0). For elution of the pyridylaminated sugar chain, Eluent A (100 mM acetate-triethylamine, pH 5.0) and Eluent B (100 mM acetate-triethylamine containing 0.5% n-butanol, pH 5.0) were used to successively elute the pyridylaminated sugar chain with a linear gradient of 30% to 100% Eluent B (0 to 35 minutes) and then 100% Eluent B (35 to 50 minutes). The analysis was performed under the following conditions: flow rate: 1 ml/min, column temperature: 40° C., detection: fluorescence (Ex: 320 nm, Em: 400 nm).

The results indicated that pyridylaminated α2,3-sialyllactose (pyridylaminated 3'-sialyllactose) was synthesized from pyridylaminated lactose when using this enzyme.

Example 4

Transfer of Sialic Acid to Monosaccharides and Disaccharides (Preparation of Sialic Acid-Containing Sugar Chains) Using (β-galactoside-α2,3-sialyltransferase Produced by Strain JT-ISH-467

(Material and Method)

A cell homogenate prepared from the strain JT-ISH-467 was partially purified by ion exchange chromatography, hydroxyapatite chromatography, and gel filtration chromatography. The thus partially purified α2,3-sialyltransferase was used in the following experiment in order to confirm the transfer of sialic acid to various monosaccharides and disaccharides.

Sialic Acid Transfer Reaction Using Various Glycosyl Acceptor Substrates

The enzymatic reaction was carried out at 25° C. for 4 hours in a reaction solution (24 µl) prepared to contain CMP-$^{14}$C-NeuAc as a glycosyl donor substrate (400 nmol (15600 cpm), final concentration in the reaction solution: 16.6 mM), any of various glycosyl acceptor substrates (10 µmol, final concentration in the reaction solution: 200 mM), sialyltransferase (0.13 mU) and NaCl (final concentration in the reaction solution: 500 mM). The monosaccharides and disaccharides used as glycosyl acceptor substrates were the following 6 substances: methyl-α-D-galactopyranoside (Gal-α-OMe), methyl-β-D-galactopyranoside (Gal-β-OMe), N-acetylgalactosamine (GalNAc), lactose (Gal-β1,4-Glc), N-acetyllactosamine (Gal-β1,4-GlcNAc), and methyl-β-D-galactopyranosyl-β-1,3-N-acetylglucosaminide (Gal-β1,3-GlcNAc-β-OMe).

After completion of the enzymatic reaction, 1.98 ml of 5 mM phosphate buffer (pH 6.8) was added to the reaction solution to stop the enzymatic reaction. Then, the enzymatic reaction solution was diluted with 5 mM phosphate buffer (pH 6.8) and applied in a volume of 2 ml to a AG1-x2 Resin ($PO_4^{3-}$ form, 0.2×2 cm) column. This column was prepared as follows: AG1-x2 Resin (OH⁻ form, BIO-RAD) was suspended in 1 M phosphate buffer (pH 6.8), and after 30 minutes, the resin was washed with distilled water and then suspended in distilled water. The eluate (0 to 2 ml) from this column was measured for its radioactivity. The eluate from this column contains the unreacted glycosyl acceptor substrate and the $^{14}$C-NeuAc (N-acetylneuraminic acid)-bound reaction product which was generated by the reaction, but unreacted CMP-$^{14}$C-NeuAc is still retained on the column. Thus, the radioactivity of $^{14}$C from each sialic acid-containing sugar chain generated as a result of the enzymatic reaction arises exclusively from the reaction product, so that the radioactivity of this fraction can be used to calculate the enzyme activity.

In the manner described above, the radioactivity of NeuAc transferred to each glycosyl acceptor substrate was measured to calculate the amount of transferred sialic acid.

(Results)

Sialic acid was found to be transferred to all the 6 monosaccharides and disaccharides used as glycosyl acceptor substrates in this experiment (see Table 2). Among the sugars used as glycosyl acceptor substrates in this experiment, N-acetyllactosamine was found to be the highest in amount of transferred sialic acid.

TABLE 2

Sialyltransferase activity of α2,3-sialyltransferase derived from strain JT-ISH-467 toward various glycosyl acceptor substrates

| Acceptor substrate | Amount of transferred sialic acid |
| --- | --- |
| Gal-α-OMe | 60.0 nmol |
| Gal-β-OMe | 50.2 nmol |
| GalNAc | 37.8 nmol |
| Gal-β1,4-Glc | 57.9 nmol |
| Gal-β1,4-GlcNAc | 74.9 nmol |
| Gal-β1,3-GlcNAc-β-OMe | 71.1 nmol |

Example 5

Nucleotide Sequence Analysis and Transformation of Gene Encoding β-galactoside-α2,3-sialyltransferase Produced by *Photobacterium phosphoreum* Strain JT-ISH-467

(1) Purification of Genomic DNA and Preparation of Genomic Library

From a cell pellet of the strain JT-ISH-467 (about 0.5 g), genomic DNA (about 100 μg) was prepared using a Qiagen Genomic-tip 100/G (Qiagen) in accordance with the instructions attached to the kit. Relative to 1-2 μg of DNA, 0.1 to 0.2 units of Sau3AI, a four base-cutter enzyme, was used for partial digestion of the DNA. The reaction buffer used was one attached to the enzyme and the reaction conditions were set at 37° C. for 30 minutes. After the reaction, EDTA (pH 8.0) was added at a final concentration of 25 mM to the reaction solution, followed by phenol/chloroform treatment. The genomic DNA was collected by ethanol precipitation and dissolved in 400 μl TE. In a centrifugal tube (Hitachi 40PA), a 40-10% gradient was prepared from 40% sucrose buffer (20 mM Tris pH 8.0, 5 mM EDTA pH 8.0, 1 M NaCl) and 10% sucrose buffer using a gradient preparation unit, and the above partially-digested DNA solution was overlayed thereon. Using an ultracentrifuge (Hitachi SCP70H, rotor: SRP28SA), the tube was centrifuged at 26,000 rpm at 20° C. for 15 hours. After centrifugation, a hole was made with a 25G needle at the bottom of the tube to collect every 1 ml aliquots from the solution at the bottom. Using a submarine electrophoretic chamber, a part of each collected sample containing the genomic DNA was electrophoresed on a 0.5-0.6% agarose gel/TAE buffer at 26 V for 20 hours to observe a fraction containing DNA of 9-16 kb size. As a marker, λ/HindIII was used. After addition of 2.5 ml TE to reduce the sucrose concentration, the fraction containing the DNA fragment of 9-16 kb size was ethanol precipitated, rinsed and dissolved in a small volume of TE.

λDASH II (Stratagene) was used as a vector to create a genomic library of the strain JT-ISH-467. The λDASH II/BamHI vector and the genomic DNA fragment were ligated overnight at 12° C. using a Stratagene ligation kit. After the reaction, the reaction solution was reacted with GigaPack III Gold Packaging extract, whereby the λ vector carrying the genomic DNA was incorporated into phage particles. The phage solution was stored at 4° C. in 500 μl SM buffer and 20 μl chloroform. *E. coli* XL1-Blue MRA(P2) (Stratagene) was grown in LBMM (LB 0.2% maltose 10 mM MgSO$_4$) to A$_{600}$=0.5, and 200 μl of this culture solution was incubated with an appropriate amount of the phage solution at 37° C. for 15 minutes. This solution was mixed with 4 ml NZY top agarose kept at 48° C., and plated in a NZY agar plate (a plastic dish of 9 cm diameter). The plate was cultured overnight at 37° C. and the number of plaques was counted to calculate the titer. As a result, the library size was calculated to be about 300,000 pfu (plaque forming unit).

(2) Primer Design and Probe Preparation

A Procise 494 cLC Protein Sequencing System (Applied Biosystems) was used to determine the amino-terminal (N-terminal) amino acid sequence and internal amino acid sequences of β-galactoside-α2,3-sialyltransferase from the strain JT-ISH-467.

Determination of the N-terminal amino acid sequence was accomplished as follows. The sialyltransferase was subjected to SDS-polyacrylamide gel electrophoresis on a 5/20% gradient gel (ATTO). After electrophoresis, the enzyme was adsorbed onto a PVDF membrane, and the sequence of amino-terminal 10 amino acids was determined with an amino acid sequencer. As a result, the N-terminal amino acid sequence of this enzyme was XNSDSKHNNS (SEQ ID NO: 4).

Also, determination of internal amino acid sequences was accomplished as follows. The sialyltransferase was subjected to SDS-polyacrylamide gel electrophoresis on a 5/20% gradient gel (ATTO). After staining the gel, a band of interest was excised and treated at 35° C. for 20 hours in lysyl endopeptidase-containing Tris buffer (pH 8.5). Then, the entire solution was applied to reversed-phase HPLC (column: Symmetry C18 3.5 μm) to separate fragment peptides. Analysis with an amino acid sequencer indicated that internal amino acid sequences of this enzyme had the following sequences: SLDSMILTNEIK (SEQ ID NO: 5), FYNFTGFNPE (SEQ ID NO: 6) and GHPSATYNQQIIDAHNMIEIY (SEQ ID NO: 7).

Based on the thus determined partial amino acid sequences of α2,3-sialyltransferase derived from *Photobacterium phosphoreum* JT-ISH-467, i.e., the N-terminal amino acid sequence XNSDSKHNNS (SEQ ID NO: 4) and two of the three internal amino acid sequences: FYNFTGFNPE (SEQ ID NO: 6) and GHPSATYNQQIIDAHNMIEIY (SEQ ID NO: 7), the following degenerate primers were designed and synthesized. Namely, the three primers shown in Table 3 below (I represents inosine) were synthesized from the N-terminal amino acid sequence XNSDSKHNNS (SEQ ID NO: 4).

TABLE 3

Table 3

| Name | Sequence 5'-3' | Mix rate | Length |
|---|---|---|---|
| 467N-RV | AAY WSI GAY WSI AAR CAY AAY AA (SEQ ID NO: 8) | 256 | 23mer |
| 467N-RV2 | GAY WSI AAR CAY AAY AAY WS (SEQ ID NO: 9) | 512 | 20mer |
| 467N-RV3 | AAY WSN GAY WSI AAR CAY AAY AA (SEQ ID NO: 10) | 1024 | 23mer |

In the table, Y represents thymine or cytosine; W represents thymine
or adenine; S represents cytosine or guanine; R represents adenine or
guanine; N represents adenine, guanine, cytosine or thymine; and
I represents inosine.

Also, the four primers shown in Table 4 below were synthesized from the internal amino acid sequence GHPSATYNQQIIDAHNMIEIY (SEQ ID NO: 7).

TABLE 4

Table 4

| Name | Sequence 5'-3' | Mix rate | Length |
|---|---|---|---|
| 467in1RV | ATH ATH GAY GCN CAY AAY ATG (SEQ ID NO: 11) | 288 | 21mer |
| 467in1FW | CAT RTT RTG NGC RTC DAT DAT (SEQ ID NO: 12) | 288 | 21mer |
| 467in1RV2 | TAY AAY CAR CAR ATH ATH GAY GC (SEQ ID NO: 13) | 288 | 23mer |
| 467in1FW2 | GCR TCD ATD ATY TGY TGR TTR TA (SEQ ID NO: 14) | 288 | 23mer |

In the table, H represents thymine, cytosine or adenine; Y represents thymine
or cytosine; R represents adenine or guanine; D represents
adenine, guanine
or thymine; and N represents adenine, guanine, cytosine or thymine.

Moreover, the two primers shown in Table 5 below were synthesized from the internal amino acid sequence FYNFTGFNPE (SEQ ID NO: 6).

TABLE 5

Table 5

| Name | Sequence 5'-3' | Mix rate | Length |
|---|---|---|---|
| 467in2RV | TAY AAY TTY ACN GGN TTY AAY CC (SEQ ID NO: 15) | 512 | 23mer |
| 467in2RN | GGR TTR AAN CCN GTR AAR TTR TA (SEQ ID NO: 16) | 512 | 23mer |

In the table, Y represents thymine or cytosine; R represents
adenine or guanine; and N represents adenine, guanine,
cytosine or thymine.

These primers were used for PCR, in which the strain JT-ISH-467 genomic DNA extracted and purified in (1) above was used as a template, to amplify partial-length DNA of the JT-ISH-467 α2,3-sialyltransferase gene, which served as a probe for library screening. As to primer combinations, the following 13 combinations in total were used: 9 combinations of the three N-terminal sequence-derived primers with 467 in1FW (SEQ ID NO: 12), 467 in1FW2 (SEQ ID NO: 14) or 467in2FW (SEQ ID NO: 16); 2 combinations of 467 in1RV (SEQ ID NO: 11) or 467 in1RV2 (SEQ ID NO: 13) with 467 in2FW (SEQ ID NO: 16); and 2 combinations of 467 in2RV (SEQ ID NO: 15) with 467 in1FW (SEQ ID NO: 12) or 467 in1FW2 (SEQ ID NO: 14). Each PCR reaction was carried out in 50 μl reaction solution containing 250 ng genomic DNA, 5 μl 10× Ex taq buffer, 4 μl 12.5 mM dNTPs, 5 μmol primer for each sequence and 0.5 Ex taq (Takara Bio Inc., Japan), using a Program Temp Control System PC-700 (ASTEK) under the following conditions: 96° C. for 3 minutes, (96° C. for 1 minute, 50° C. for 1 minute, 72° C. for 2 minutes)×40 cycles, and 72° C. for 6 minutes. As a result, amplification of PCR products was observed in 9 primer combinations (i.e., except for 467N-RV (SEQ ID NO: 8) & 467 in1FW (SEQ ID NO 12), 467N-RV (SEQ ID NO: 8) & 467 in2FW (SEQ ID NO: 16), 467 in1RV (SEQ ID NO: 11) & 467 in2FW (SEQ ID NO: 16), and 467 in2RV (SEQ ID NO: 15) & 467 in1FW (SEQ ID NO: 12)). Among these PCR products, one derived from the combination 467N-RV3 (SEQ ID NO: 10) & 467 in1FW (SEQ ID NO: 12) which allowed specific and high-efficiency amplification was cloned into vector pCR2.1TOPO (Invitrogen). Ligation was carried out according to the instructions attached to the vector kit. The DNA was introduced into *E. coli* TB1 by electroporation and the plasmid DNA was extracted in a routine manner (Sambrook et al. 1989, Molecular Cloning, A laboratory manual, 2nd edition (which is hereby incorporated by reference in its entirety)). This clone was analyzed by PCR with M13 primers (Takara Bio Inc., Japan) to determine the nucleotide sequence of the PCR product from both ends using an ABI PRISM fluorescent sequencer (Model 310 Genetic Analyzer, Perkin Elmer).

A homology search with the BLAST program was made for the determined DNA nucleotide sequence (929 bp: SEQ ID NO: 17) against the GeneBank database of the National Center for Biotechnology Information (NCBI). As a result, there was no DNA sequence with significant homology. This means that the DNA nucleotide sequence identified by the present invention for the α2,3-sialyltransferase gene from *Photobacterium phosphoreum* strain JT-ISH-467 is a novel sequence. Next, this nucleotide sequence was translated into amino acids and subjected again to a BLAST search, detecting 30% homology with α2,6-sialyltransferase (JC5898) from *Photobacterium damselae*, 26% homology with a putative protein PM0188 (AAK02272) of *Pasteurella multocida* subsp. *multocida* strain Pm70, and 21% homology with a putative protein HD0053 (AAP95068) of *Haemophilus ducreyi* strain 35000HP. Moreover, the translated amino acid sequence was found to contain the whole of the above internal amino acid sequences FYNFTGFNPE (SEQ ID NO: 6) and SLDSMILTNAIK (SEQ ID NO: 5) determined directly from the purified enzyme, as well as parts of the N-terminal amino acid sequence XNSDSKHNNS (SEQ ID NO: 4) and the internal amino acid sequence GHPSATYNQQIIDAHNMIEIY (SEQ ID NO: 7). These results indicated that the cloned DNA was a part of the α2,3-sialyltransferase gene from *Photobacterium phosphoreum* strain JT-ISH-467, and that the amino acid sequence of α2,3-sialyltransferase from *Photobacterium phosphoreum* strain JT-ISH-467 according to the present invention was a novel amino acid sequence showing as low as 30% homology with the reported sequences.

(3) Screening and Gene Cloning

The DNA fragment cloned in (2) above, composed of a part of the α2,3-sialyltransferase gene from *Photobacterium phosphoreum* strain JT-ISH-467, was excised from the pCR2.1 TOPO vector with a restriction enzyme EcoRI and used as a probe to screen the *Photobacterium phosphoreum* strain JT-ISH-467-derived genomic DNA library created in (1) above. In a round dish of 9 cm diameter, about 300-500 pfu phages were plated together with XL1-blue MRA(P2) host cells according to the instructions attached to a λDASH II/BamHI vector kit (Stratagene). Plaques were contacted with a Hybond-N+ nylon membrane filter (Amersham), treated with alkali according to the instructions attached to the membrane to cause DNA denaturation, and then fixed on the membrane. The probe was labeled with $^{32}P$ using a rediprime II™ DNA labelling system (Amersham Biosciences). Hybridization was carried out overnight at 65° C. in 0.5 M sodium phosphate buffer pH 7.2, 7% SDS, 1 mM EDTA, and washing conditions were set as follows: twice at 65° C. for 15 minutes in 40 mM sodium phosphate buffer pH 7.2, 1 mM EDTA, 5% SDS, followed by twice at 65° C. for 15 minutes in 40 mM sodium phosphate buffer pH 7.2, 1% SDS, 1 mM EDTA. During primary screening, 24 positive clones were obtained from about 5,000 pfu phages. Secondary screening (also serving as plaque purification) was performed on 18 of the resulting clones. As a result, it was possible to obtain 6 selected and purified plaques.

These plaques were collected, and each was plated in a NZY plate together with *E. coli* XL1-blue MRA(P2) at several ten thousand pfu per plate and incubated overnight at 37° C. SM buffer was added in 4 ml volumes to 6 plates with confluent plaques, and the plates were allowed to stand overnight at 4° C. Phage plate lysates were collected with Pasteur pipettes, and λDNA was extracted and purified from each lysate with a QIAGEN Lambda Mini Kit (QIAGEN). These 6 λDNAs and the total genomic DNA of the strain JT-ISH-467 purified in (1) were digested with restriction enzymes EcoRI and HindIII, and fractionated by 0.7% agarose gel electrophoresis, followed by alkaline blotting with 0.4 M NaOH to transfer the gel onto a Hybond-N+ nylon membrane filter (Amersham Biosciences). Southern hybridization was performed on this filter, as described above, using the above 929 bp probe (SEQ ID NO: 17). As a result, EcoRI digestion detected a band of 9 kb or larger, while HindIII digestion detected a band of 4.6 kb for each λDNA and the genomic DNA. Then, each λDNA was digested again with HindIII and electrophoresed on an agarose gel to collect a 4.6 kb HindIII fragment, which was then cloned in a routine manner into a HindIII site of plasmid vector pBluescript SK(-).

Next, to determine the entire nucleotide sequence of the α2,3-sialyltransferase gene from *Photobacterium phosphoreum* strain JT-ISH-467, the primers shown in Table 6 below were synthesized on the basis of the partial DNA sequence of the gene (described above, 929 bp; SEQ ID NO: 17).

TABLE 6

| Name | Sequence 5'-3' | Length |
|---|---|---|
| 467-23STinRV1 | TGTTGATAGAGCAACATTACC (SEQ ID NO: 18) | 21mer |
| 467-23STinRV2 | TGGTAATACCTTATGGGCAG (SEQ ID NO: 19) | 20mer |
| 467-23STinRV3 | GAACAGCAACGGCAGAGC (SEQ ID NO: 20) | 18mer |
| 467-23STinRV4 | CTAATTCAATTCAAGGATTGG (SEQ ID NO: 21) | 21mer |

TABLE 6-continued

| Name | Sequence 5'-3' | Length |
|---|---|---|
| 487-23STinFW1 | TGGTAATGTTGCTCTATCAAC (SEQ ID NO: 22) | 21mer |
| 467-23STinFW2 | ACTGCCCATAAGGTATTACC (SEQ ID NO: 23) | 20mer |
| 467-23STinFW3 | GCTCTGCCGTTGCTGTTC (SEQ ID NO: 24) | 18mer |

Using these primers, the 4.6 kb HindIII fragment was analyzed for its internal nucleotide sequence with an ABI PRISM fluorescent sequencer (Model 310 Genetic Analyzer, Perkin Elmer) to analyze internal and surrounding nucleotide sequences of the α2,3-sialyltransferase gene from *Photobacterium phosphoreum* strain JT-ISH-467. As a result, the sequence of SEQ ID NO: 1 in the Sequence Listing was obtained. This sequence corresponds to the entire nucleotide sequence of the open reading frame (ORF) of the α2,3-sialyltransferase gene from *Photobacterium* phosphoreum strain JT-ISH-467. Since there is an in-frame translation termination codon upstream of the first ATG, this ATG codon is a possible translation initiation codon for this gene.

The ORF of the α2,3-sialyltransferase gene from *Photobacterium phosphoreum* strain JT-ISH-467 was composed of 1230 nucleotides and encoded 409 amino acids. This amino acid sequence is shown in SEQ ID NO: 2 in the Sequence Listing. This amino acid sequence contains all of the entire 4 amino acid sequences determined from the purified enzyme. Although the first residue of the N-terminal amino acid sequence has not been decoded, the corresponding amino acid deduced from the gene was Cys (cysteine). Moreover, since the N-terminus of the mature protein corresponds to the 22 nd Cys of the sequence shown in SEQ ID NO: 2 in the Sequence Listing, the sequence of the first 21 amino acids was believed to be processed and removed in *Photobacterium phosphoreum*. Genetic information processing software GENETYX Ver. 7 (Genetyx Corporation, Japan) was used to analyze full-length homology of the α2,3-sialyltransferase protein and gene from *Photobacterium phosphoreum* strain JT-ISH-467 according to the present invention in comparison with their homologues. For the amino acid sequence, there was 32% homology with α-2,6-sialyltransferase (JC5898) from *Photobacterium damselae* and 28% homology with a putative protein PM0188 (AAK02272) of *Pasteurella multocida* subsp. *multocida* strain Pm70. For the gene DNA sequence, there was 53% and 51% homology with them, respectively.

(4) Construction of Expression Vector

To test whether the cloned gene had sialyltransferase activity, the full-length of the gene and its derivative modified to remove the N-terminal signal peptide region were each integrated into an expression vector to produce a protein in *E. coli* cells, followed by measuring the activity of this expressed protein.

Genetic information processing software GENETYX Ver. 7 was used to analyze the amino acid sequence of α2,3-sialyltransferase from *Photobacterium phosphoreum* strain JT-ISH-467, estimating that the N-terminal 24 amino acids would constitute the signal peptide. Then, primers 467-23ST-N0-Pci (SEQ ID NO: 27) and 467-23ST-C0-Bm (SEQ ID NO: 26) for cloning the full-length gene (herein referred to as "467-N0C0"), as well as primers 467-23ST-N2-Nco (SEQ ID NO: 25) and 467-23ST-C0-Bm (SEQ ID NO: 26) for cloning a gene encoding a protein lacking the amino acids of the signal peptide region (herein referred to as "467-N2C0") were designed and synthesized (Table 7).

TABLE 7

| Name | Sequence 5'-3' | Length |
|---|---|---|
| 467-23ST-N2-Nco | GGGCTGTA<u>CC</u> \|ATG\|GACTCTAAGCACAATAACTCAG (SEQ ID NO: 25) | 35 mer |
| 467-23ST-C0-Bm | CTTAGAAT<u>GGATCC</u>\|TTA\|CTGCAAATCACTTATCAAC (SEQ ID NO: 26) | 36 mer |
| 467-23ST-N0-Pci | AAGGGAAT<u>AC</u>\|ATG\|TTCGTTTTTTGTAAAAAAATA (SEQ ID NO: 27) | 34 mer |

Restriction enzyme sites PciI (467-23ST-N0-Pci), NcoI (467-23ST-N2-Nco) and BamHI (467-23ST-C0-Bm), which have been integrated into the cloning primers, are underlined. The translation initiation codon ATG and the complementary sequence TAA corresponding to the translation termination codon are boxed. Moreover, within the primer sequences, sequences annealing to the template DNA on the 3' side of the restriction enzyme sites are shown in bold type. The template DNA used for PCR was a plasmid carrying the above 4.6 kb HindIII fragment containing the full-length of the α2,3-sialyltransferase gene from *Photobacterium phosphoreum* strain JT-ISH-467. The reaction conditions for PCR were set as follows. In 50 μl reaction solution containing 100 ng template DNA, 5 μl 10× Ex taq buffer, 4 μl 2.5 mM dNTPs, 50 μmol primer and 0.5 μl Ex taq (Takara Bio Inc., Japan), PCR was carried out using a Program Temp Control System PC-700 (ASTEK) under the following conditions: 96° C. for 3 minutes, (96° C. for 1 minute, 50° C. for 1 minute, 72° C. for 2 minutes)×15 cycles, and 72° C. for 6 minutes. As a result, PCR products of approximately 1.2 kb and 1.1 kb were amplified for 467-N0C0 and 467-N2C0, respectively. In these PCR products, 467-N0C0 was double-digested with restriction enzymes PciI (New England Biolab) and BamHI (Takara Bio Inc., Japan), while 467-N2C0 was double-digested with restriction enzymes NcoI (Takara Bio Inc., Japan) and BamHI, followed by gel purification. pTrc99A (Pharmacia LKB) was used as a vector for *E. coli* expression. After being double-digested with restriction enzymes NcaI & BamHI and purified on a gel, this vector was ligated with each restriction enzyme-treated PCR product using a Takara Ligation Kit (Takara Bio Inc., Japan) and transfected into *E. coli* TB1. In a routine manner, the plasmid DNA was extracted and analyzed by restriction enzyme analysis to confirm the integration of the insert. To examine PCR-induced nucleotide changes, the entire nucleotide sequence was determined for two clones of 467-N0C0 and three clones of 467-N2C0. As a result, in the case of 467-N0C0, one clone (the first clone of ISH467-N0C0) had a nucleotide change from adenine (A) to guanine (G) at position 569 in the nucleotide sequence of SEQ ID NO: 1, which resulted in a codon change from AAC to AGC and hence an amino acid change from aspartic acid (Asn) to serine (Ser) at position 190 in the amino acid sequence of SEQ ID NO: 2. Asn and Ser are both members of polar amino acids. In contrast, another clone (the second clone of ISH467-N0C0) had no nucleotide change, and the nucleotide sequence of SEQ ID NO: 1 was confirmed for this clone. Next, the entire nucleotide sequence was determined for the three 467-N2C0 clones. As a result, it was determined that the first and second clones each had a nucleotide mutation leading to an amino acid replacement. Namely, the first clone of ISH467-N2C0 had a mutation from thymine (T) to cytosine (C) at position 476 in the nucleotide sequence of SEQ ID NO: 1, which resulted in a codon change from TTT to TCT and hence a replacement of phenylalanine (Phe) by serine (Ser) at position 159. The second clone of ISH467-N2C0 had a deletion of thymine (T) at position 78 in the nucleotide sequence of SEQ ID NO: 1, which resulted in a frameshift and thereby prevented proper protein translation. In contrast, the third clone of ISH467-N2C0 had no mutation and comprised the very same sequence covering nucleotides 73 to 1230 of SEQ ID NO: 1.

(5) Expression Induction and Activity Measurement

An induction experiment of protein expression was performed on the two 467-N0C0 clones and the three 467-N2C0 clones obtained in (4) above. A single colony of *E. coli* TB1 having the expression vector pTrc99A carrying each clone was inoculated into LB medium (5 ml) containing an antibiotic, ampicillin (final concentration 100 μg/mL), and pre-cultured at 30° C. to about $A_{600}$=0.5, followed by addition of IPTG (isopropyl-β-D(−)-thiogalactopyranoside, Wako Pure Chemical Industries, Ltd. Japan) at a final concentration of 1 mM. After culturing with shaking at 30° C. for an additional 4 hours, the cells in 2 ml culture solution were collected by centrifugation. These cells were suspended in 200 μl of 20 mM BisTris buffer (pH 7.0) containing 0.336% Triton X-100 and 0.5 M sodium chloride, and ultrasonically homogenized under ice cooling. The resulting homogenate was defined as a crude enzyme solution and provided for activity measurement. The reaction was carried out in duplicate, and the reaction composition was the same as shown in Example 1, except that the reaction time was set to 15 hours. As a result, as shown in Table 8 below, it was demonstrated that there was a factor transferring $^{14}$C-labeled NeuAc in the glycosyl donor CMP-NeuAc to the glycosyl acceptor substrate lactose, i.e., sialyltransferase activity in both crude enzyme solutions from the first and second clones of ISH467-N0C0. Likewise, sialyltransferase activity was also observed in both crude enzyme solutions from the first and third clones of ISH467-N2C0. In contrast, sialyltransferase activity was not contained in either a crude enzyme solution from the second clone of ISH467-N2C0 or a reaction solution containing no crude enzyme solution. These results indicated that *E. coli* cells introduced with the first or second clone of ISH467-N0C0 or the first or third clone of ISH467-N2C0 expressed sialyltransferase.

TABLE 8

Sialyltransferase activity in *E. coli* homogenate with recombinant β-galactoside-α2,3-sialyltransferase gene from JT-ISH-467 strain

| Crude enzyme solution | Radioactivity (cpm) | | |
|---|---|---|---|
| | Round 1 | Round 2 | Average |
| ISH467-N0C0 first clone | 8496 | 7486 | 7991 |
| ISH467-N0C0 second clone | 7097 | 7809 | 7453 |
| ISH467-N2C0 third clone | 8547 | 8481 | 8514 |
| Absence | 667 | 609 | 638 |
| ISH467-N2C0 first clone | 10514 | 9033 | 9773.5 |
| ISH467-N2C0 second clone | 685 | 689 | 687 |
| Absence | 948 | 914 | 931 |

(6) Confirmation of α2,3 sialyltransferase Activity

The crude enzyme solution from (5) above was used to examine whether sialyltransferase expressed by *E. coli* cells introduced with the first clone of ISH467-N2C0 had α2,3 sialyltransferase activity. As in the case of Example 3, pyridylaminated lactose (Galβ1-4Glc-PA, PA-Sugar Chain 026, Takara Bio Inc., Japan) was used as a glycosyl acceptor to carry out the enzymatic reaction. After the reaction, the reaction solution was heated at 95° C. for 5 minutes to inactivate the enzyme, followed by HPLC analysis. It should be noted that the enzymatic reaction was accomplished at 25° C. for 6 hours using pyridylaminated lactose and CMP-sialic acid dissolved at 2.0 μM and 5.7 μM, respectively, in 25 μl of 20 mM cacodylate buffer (pH 6.0) (Reaction 1). On the other hand, a control experiment (Reaction 2) was carried out using a reaction solution free from CMP-sialic acid. Further, to clarify the retention time of standards, the crude enzyme solution was inactivated by thermal treatment (95° C., 5 minutes) and tested in the presence of pyridylaminated lactose and pyridylaminated α2,3-sialyllactose (pyridylaminated 3'-sialyllactose) (Neu5Acα2-3Galβ1-4Glc-PA, PA-Sugar Chain 029, Takara Bio Inc., Japan).

The analysis results obtained for the standards (FIG. 1-1) showed that the retention time was 4.1 minutes for pyridylaminated lactose and 5.4 minutes for pyridylaminated α2,3-sialyllactose (pyridylaminated 3'-sialyllactose). This indicated that the peak having a retention time of 5.3 minutes (FIG. 1-2), which was not detected in Reaction 2 (FIG. 1-3), corresponded to pyridylaminated α2,3-sialyllactose (pyridylaminated 3'-sialyllactose). Namely, it was proven that sialyltransferase expressed by *E. coli* cells introduced with the first clone of ISH467-N2C0 had α2,3 sialyltransferase activity.

For the first and second clones of ISH467-N0C0 as well as the third clone of ISH467-N2C0, the same procedure was also repeated to examine whether sialyltransferases expressed by *E. coli* cells introduced with these clones had α2,3 sialyltransferase activity. As a result, a peak of pyridylaminated α2,3-sialyllactose (pyridylaminated 3'-sialyllactose) was detected for each clone as a reaction product in the reaction catalyzed by *E. coli*-expressed sialyltransferase. Thus, these enzymes were found to have α2,3 sialyltransferase activity.

Example 6

Cloning and Nucleotide Sequence Analysis of β-galactoside-α2,3-sialyltransferase Gene from *Photobacterium* sp. Strain JT-ISH-224, and *E. coli* Expression of the Gene (1) Confirmation of β-galactoside-α2,3-sialyltransferase Activity in JT-ISH-224 Strain and the Presence of Its Enzyme Gene To determine whether there was a homologue of the α2,3-sialyltransferase gene derived from *Photobacterium phosphoreum* strain JT-ISH-467, genomic Southern hybridization was performed on *Photobacterium* sp. strain JT-ISH-224 that was found to have sialyltransferase activity in Example 1. Genomic DNA was prepared from a cell pellet of the JT-ISH-224 strain, as described in Example 5(1). According to the procedure described in Example 5(3), the genomic DNA of the JT-ISH-224 strain was then digested with a restriction enzyme EcoRI or HindIII and fractionated by 0.7% agarose gel electrophoresis, followed by alkaline blotting with 0.4 M NaOH to transfer the gel onto a Hybond-N+ nylon membrane filter (Amersham Biosciences). Southern hybridization was performed on this filter, as described in Example 5(3), using as a probe the above partial fragment (929 bp; SEQ ID NO: 17) of the α2,3-sialyltransferase gene from the strain JT-ISH-467, except that the hybridization and washing temperatures were set to 55° C. As a result, EcoRI digestion detected a band of 16 kb, while HindIII digestion detected bands of 5 kb and 2.7 kb. These results indicated that the JT-ISH-224 strain had a homologue of the α2,3-sialyltransferase gene derived from the JT-ISH-467 strain.

(2) Cloning of α2,3-sialyltransferase Gene from Strain JT-ISH-224

Next, the α2,3-sialyltransferase gene of the JT-ISH-224 strain was cloned. λDASH II (Stratagene) was used to construct a genomic library from the genomic DNA of the strain JT-ISH-224, as described in Example 5(1). The partial fragment (929 bp; SEQ ID NO: 17) of the α2,3-sialyltransferase gene from the strain JT-ISH-467 was used as a probe to screen the genomic library of the strain JT-ISH-224, except that the hybridization and washing temperatures were set to 55° C., as in the case of Example 6(1). As a result, 12 clones were obtained up to the end of secondary screening (also serving as plaque purification), 6 of which were treated with a QIAGEN Lambda Mini Kit (QIAGEN) to purify their λDNAs, as described in Example 5(3). Further, 3 of these λDNA samples and the total genomic DNA of the strain JT-ISH-224 were digested with a restriction enzyme EcoRI or HindIII. Each digest was fractionated by agarose gel electrophoresis and transferred onto a nylon membrane filter, as described above. This filter was provided for Southern analysis using as a probe the partial fragment (929 bp; SEQ ID NO: 17) of the α2,3-sialyltransferase gene from the strain JT-ISH-467. The hybridization and washing temperatures were set to 55° C. As a result, EcoRI digestion detected a band of 12 kb or larger, while HindIII digestion detected two bands of 5 kb and 2.7 kb for each of the 3 λDNA samples and the total genomic DNA of the strain JT-ISH-224. Then, each λDNA sample was digested again with HindIII, followed by gel purification to purify these two DNA fragments of 5 kb and 2.7 kb, each of which was then cloned in a routine manner into a HindIII site of plasmid vector pBluescript SK(−).

Next, nucleotide sequences at both ends of the 5 kb HindIII fragment and the 2.7 kb HindIII fragment were determined for these clones using M13 primers (Takara Bio Inc., Japan) in an ABI PRISM fluorescent sequencer (Model 310 Genetic Analyzer, Perkin Elmer). As a result, amino acid sequences deduced from the DNA sequence on one side of the 5 kb fragment and the DNA sequence on one side of the 2.7 kb fragment showed homology with sialyltransferase when analyzed by database search. To completely determine DNA of the gene for the enzyme of the strain JT-ISH-224, the primer shown in Table 9 below was synthesized on the basis of the DNA sequence obtained from the 2.7 kb HindIII fragment, and used for nucleotide sequencing.

TABLE 9

| Name | Sequence 5'-3' | Length |
|---|---|---|
| 224-23ST-inRV1 | CAGGAACTGCAACAGCA-GAG (SEQ ID NO: 34) | 20mer |

As a result, the sequence of SEQ ID NO: 28 in the Sequence Listing was obtained. This sequence corresponds to the entire nucleotide sequence of the open reading frame (ORF) of the α2,3-sialyltransferase gene from the strain JT-ISH-224. Since there is an in-frame translation termination codon upstream of the first ATG, this ATG codon is a possible translation initiation codon for this gene. The ORF of the α2,3-sialyltransferase gene derived from *Photobacterium* sp. strain JT-ISH-224 was composed of 1230 nucleotides and encoded 409 amino acids, as in the case of the α2,3-sialyltransferase gene from *Photobacterium phosphoreum* strain JT-ISH-467. This amino acid sequence is shown in SEQ ID NO: 29 in the Sequence Listing. The gene had an internal HindIII site. GENETYX Ver. 7 was used to analyze nucleic acid and amino acid sequences, indicating that the α2,3-sialyltransferase gene from the strain JT-ISH-224 had 92% homology with the α2,3-sialyltransferase gene from the strain JT-ISH-467. For the amino acid sequence, there was 92% homology with α2,3-sialyltransferase from the strain JT-ISH-467. Moreover, the amino acid sequence of α2,3-sialyltransferase from the strain JT-ISH-224 had 33% homology with α2,6-sialyltransferase (JC5898) from *Photobacterium damselae* and 29% homology with a putative protein PM0188 (AAK02272) of *Pasteurella multocida* subsp. *multocida* strain Pm70. For the gene DNA sequence, there was 54% and 50% homology with them, respectively.

(3) Construction of Expression Vector

To test whether the cloned gene had sialyltransferase activity, the full-length of the gene and its derivative modified to remove the N-terminal signal peptide region were each integrated into an expression vector to produce a protein in *E. coli* cells, followed by measuring the activity of this expressed protein.

Genetic information processing software GENETYX Ver. 7 was used to analyze the amino acid sequence of α2,3-sialyltransferase from the strain JT-ISH-224, estimating that the N-terminal 24 amino acids would constitute the signal peptide. Then, primers 224-23ST-N0-Pci (SEQ ID NO: 35) and 224-23ST-C0new-Bm (SEQ ID NO: 37) for cloning the full-length gene (herein referred to as "224-N0C0"), as well as primers 224-23ST-N1-Nco (SEQ ID NO: 36) and 224-23ST-C0new-Em (SEQ ID NO: 37) for cloning a gene encoding a protein lacking the amino acids of the signal peptide region (herein referred to as "224-N1C0") were designed and synthesized (Table 10).

TABLE 10

| Name | Sequence 5'-3' | Length |
|---|---|---|
| 224-23ST-N0-Pci | AAGGGAAT<u>AC</u> ATG TTCGTTTTTTGTAAAAAAATG (SEQ ID NO: 35) | 34 mer |
| 224-23ST-N1-Nco | GGGATGTA<u>CC</u> ATG GACTCTAATCACAATAACTCAG (SEQ ID NO: 36) | 35 mer |
| 224-23ST-C0new-Bm | ATTAAAAT<u>GGATCC</u> TTA CTGCAAATCACTTATCAAC (SEQ ID NO: 37) | 36 mer |

Restriction enzyme sites PciI (224-23ST-N0-Pci), NcoI (224-23ST-N-1-Nco) and BamHI (224-23ST-C0new-Bm), which have been integrated into the cloning primers, are underlined. The translation initiation codon ATG and the complementary sequence TAA corresponding to the translation termination codon are boxed. Moreover, within the primer sequences, sequences annealing to the template DNA are shown in bold type. In the case of primer 224-23ST-N0-Pci, cytosine (C) located immediately after the translation initiation codon ATG is replaced by thymine (T) as a result of introducing the PciI site for the subsequent cloning. For this reason, the amino acid sequence located immediately after the translation initiation methionine is changed from leucine (Leu) to phenylalanine (Phe). This mutation was judged to be less likely to cause a great change in enzyme activity because both Leu and Phe are members of hydrophobic amino acids and because this site is within the signal peptide region.

Subsequently, PCR was carried out to amplify the α2,3-sialyltransferase gene from the strain JT-ISH-224 for use in integration into an expression vector. The template DNA used was the above λDNA containing the α2,3-sialyltransferase gene from the strain JT-ISH-224. The reaction conditions for PCR were set as follows. In 50 µl reaction solution containing 100 ng template DNA, 5 µl 10× Ex taq buffer, 4 µl 2.5 mM dNTPs, 50 pmol primer and 0.5 µl Ex taq (Takara Bio Inc., Japan), PCR was carried out using a Program Temp Control System PC-700 (ASTEK) under the following conditions: 96° C. for 3 minutes, (96° C. for 1 minute, 50° C. for 1 minute, 72° C. for 2 minutes)×15 cycles, and 72° C. for 6 minutes. As a result, PCR products of approximately 1.2 kb and 1.1 kb were amplified for 224-N0C0 and 224-N1C0, respectively. These PCR products were double-digested with restriction enzymes PolI (New England Biolab) and BamHI (for 224-N0C0) or with restriction enzymes NcoI and BamHI (for 224-N1C0), followed by gel purification. pTrc99A was used as a vector for E. coli expression. After being double-digested with restriction enzymes NcoI & BamHI and purified on a gel, this vector was ligated with each restriction enzyme-treated PCR product using a Takara Ligation Kit (Takara Bio Inc., Japan) and transformed into E. coli TB1. In a routine manner, the plasmid DNA was extracted and analyzed by restriction enzyme analysis to confirm the integration of the insert. Further, the entire nucleotide sequence was confirmed for 224-N0C0 (the first clone of ISH224-N0C0) and 224-N1C0 (the first clone of ISH224-N1C0). As a result, the first clone of ISH224-N0C0 was confirmed to have the above replacement of Leu by Phe, but there was no other mutation in its nucleotide sequence. Likewise, the first clone of ISH224-N1C0 had no mutation in its nucleotide sequence and comprised a desired nucleotide sequence, i.e., nucleotides 73 to 1230 of SEQ ID NO: 28 in the Sequence Listing.

(4) Expression Induction and Activity Measurement

In the same manner as shown in Example 5(5), an induction experiment of protein expression was performed on 2 clones, i.e., the first clone of ISH224-N0C0 and the first clone of ISH224-N1C0 to measure their enzyme activity. As a result, as shown in Table 11 below, sialyltransferase activity was observed in both crude enzyme solutions from the first clone of ISH224-N0C0 and the first clone of ISH224-N1C0.

TABLE 11

Sialyltransferase activity in E. coli homogenate with JT-ISH-224-derived recombinant homologue of β-galactoside-α2,3-sialyltransferase gene from strain JT-ISH-467

| Crude enzyme solution | Radioactivity (cpm) | | |
|---|---|---|---|
| | Round 1 | Round 2 | Average |
| ISH224-N0C0 first clone | 9273 | 8468 | 8870.5 |
| ISH224-N1C0 first clone | 9330 | 9415 | 9672.5 |
| Absence | 667 | 609 | 638 |

(5) Confirmation of α-2,3 sialyltransferase Activity

In the same manner as shown in Example 5(6), the first clone of ISH224-N0C0 and the first clone of ISH224-N1C0 were each introduced into E. coli cells to express the encoded enzyme, followed by reaction using pyridylaminated lactose as a glycosyl acceptor to examine the enzyme for its α-2,3 sialyltransferase activity. As a result of HPLC evaluation on the reaction product of each sialyltransferase expressed by E. coli cells, a peak of pyridylaminated α2,3-sialyllactose (pyridylaminated 3'-sialyllactose) was detected for each clone. This result indicated that sialyltransferase from the strain JT-ISH-224 had α-2,3 sialyltransferase activity.

Example 7

Cloning and Nucleotide Sequence Analysis of β-galactoside-α2,3-sialyltransferase Gene from Vibrio sp. Strain JT-FAJ-16, and E. coli Expression of the Gene (1) Confirmation of β-galactoside-α2,3-sialyltransferase Activity in JT-FAJ-16 Strain and the Presence of Its Enzyme Gene To determine whether there was a homologue of the α2,3-sialyltransferase gene from Photobacterium phosphoreum strain JT-ISH-467, genomic Southern hybridization was performed on Vibrio sp. strain JT-FAJ-16 that was found to have sialyltransferase activity in Example 1. Genomic DNA was prepared from a cell pellet of the strain JT-FAJ-16, as described in Example 5(1). According to the procedure described in Example 5(3), the genomic DNA was then digested with restriction enzymes EcoRI and HindIII and fractionated by 0.7% agarose gel electrophoresis, followed by alkaline blotting with 0.4 M NaOH to transfer the gel onto a Hybond-N+ nylon membrane filter (Amersham Biosciences). Southern hybridization was performed on this filter, as described in Example 5(3), using the above 929 bp probe (SEQ ID NO: 17), except that the hybridization and washing temperatures were set to 55° C. As a result, EcoRI digestion detected a band of 3.6 kb, while HindIII digestion detected a band of 7 kb. This indicated that the JT-FAJ-16 strain had a homologue of the α2,3-sialyltransferase gene from the strain JT-ISH-467.

(2) Cloning of α2,3-sialyltransferase Gene Derived from JT-FAJ-16 Strain

Next, the α2,3-sialyltransferase gene of the JT-FAJ-16 strain was cloned. λDASH II (Stratagene) was used to construct a genomic library from the genomic DNA of the strain JT-FAJ-16, as described in Example 5(1). The partial fragment (929 bp; SEQ ID NO: 17) of the α2,3-sialyltransferase gene from the strain JT-ISH-467 was used as a probe to screen the genomic library of the strain JT-FAJ-16, except that the hybridization experiment was performed using an ECL direct labelling & detection system (Amersham Biosciences). The probe was prepared according to the instructions attached to the kit. Hybridization was accomplished at 37° C. for 4 hours using the hybridization buffer included in the kit, which was supplemented with 5% (w/v) blocking reagent and 0.5 M NaCl. Washing was performed twice in 0.4% SDS, 0.5×SSC at 50° C. for 20 minutes and once in 2×SSC at room temperature for 5 minutes. Signal detection was performed according to the instructions attached to the kit.

As a result, the primary screening (also serving as plaque purification) resulted in 12 clones, 6 of which were treated with a QIAGEN Lambda Mini Kit (QIAGEN) to purify their λDNAs, as described in Example 5(3). Further, these λDNA samples and the total genomic DNA of the strain JT-FAJ-16 were digested with a restriction enzyme EcoRI. Each digest was fractionated by agarose gel electrophoresis and transferred onto a nylon membrane filter, as described above. This filter was provided for Southern analysis with an ECL system under the same conditions as shown above using as a probe the partial fragment (929 bp; SEQ ID NO: 17) of the α2,3-sialyltransferase gene from the strain JT-ISH-467. As a result, a band of 3.6 kb was detected for each of the 6λDNA samples and the total genomic DNA of the strain JT-FAJ-16. Then, each λDNA sample was digested again with EcoRI, followed by gel purification to purify this 3.6 kb DNA fragment, which was then cloned in a routine manner into an EcoRI site of plasmid vector pBluescript SK(−).

Next, nucleotide sequences at both ends were determined for the 3.6 kb EcoRI fragment that appeared to contain the α2,3-sialyltransferase gene from the strain JT-FAJ-16, using M13 primers (Takara Bio Inc., Japan) in an ABI PRISM fluorescent sequencer (Model 310 Genetic Analyzer, Perkin Elmer). As a result, an amino acid sequence deduced from the DNA sequence at one end showed 27% homology with α2,6-sialyltransferase (JC5898) from *Photobacterium* damselae when analyzed by database search. To completely determine the entire nucleotide sequence of the α2,3-sialyltransferase gene of the strain JT-FAJ-16, the primers shown in Table 12 below were synthesized on the basis of the DNA sequence obtained from the 3.6 kb EcoRI fragment, and used for nucleotide sequencing.

TABLE 12

Table 12

| Name | Sequence 5'-3' | Length |
|---|---|---|
| FAJEc3.6RV1 | TTC AAA ACT GCC TGA GTC AG (SEQ ID NO: 38) | 20mer |
| FAJEc3.6RV2 | ATT TCA TGG TCT AGA TAC CC (SEQ ID NO: 39) | 20mer |

Based on the resulting nucleotide sequence data, the primers shown in Table 13 below were further designed and synthesized to determine the entire nucleotide sequence.

TABLE 13

Table 13

| Name | Sequence 5'-3' | Length |
|---|---|---|
| FAJ23STinFW3 | CTG ACT CAG GCA GTT TTG AA (SEQ ID NO: 40) | 20mer |
| FAJ23STinFW4 | GAA AGC AAC TCT CTC AAT GGG (SEQ ID NO: 41) | 21mer |
| FAJ23STinRV3 | ATA AAC CCA TTG AGA GAG TTG (SEQ ID NO: 42) | 21mer |

As a result, the sequence of SEQ ID NO: 30 in the Sequence Listing was obtained. This sequence corresponds to the entire nucleotide sequence of the open reading frame (ORF) of the α2,3-sialyltransferase gene from the strain JT-FAJ-16. Since there is an in-frame translation termination codon upstream of the first ATG, this ATG codon is a possible translation initiation codon for this gene. The ORF of the α2,3-sialyltransferase gene from the strain JT-FAJ-16 was composed of 1209 nucleotides and encoded 402 amino acids. This amino acid sequence is shown in SEQ ID NO: 31 in the Sequence Listing. GENETYX Ver. 7 was used to analyze nucleic acid and amino acid sequences, indicating that the α2,3-sialyltransferase gene from the strain JT-FAJ-16 had 69.7% and 68% homology with the α2,3-sialyltransferase genes from the strains JT-ISH-467 and JT-ISH-224, respectively. For the amino acid sequence, there was 64.7% and 64.8% homology with them, respectively. Moreover, the amino acid sequence of α2,3-sialyltransferase from the JT-FAJ-16 strain had 30.5% homology with α2,6-sialyltransferase (JC5898) from *Photobacterium damselae* and 27.3% homology with a putative protein PM0188 (AAK02272) of *Pasteurella multocida* subsp. *multocida* strain Pm70. For the gene DNA sequence, there was 51.2% and 48.3% homology with them, respectively.

(3) Construction of Expression Vector

To test whether the cloned gene had sialyltransferase activity, the full-length of the gene and its derivative modified to remove the N-terminal signal peptide region were each integrated into an expression vector to produce a protein in *E. coli* cells, followed by measuring the activity of this expressed protein.

Genetic information processing software GENETYX Ver. 7 was used to analyze the amino acid sequence of α2,3-sialyltransferase from the strain JT-FAJ-16, estimating that the N-terminal 22 amino acids would constitute the signal peptide. Then, primers FAJ23STN0-BspHI (SEQ ID NO: 43) and FAJ23STC0-BamHI (SEQ ID NO: 45) for cloning the full-length gene (herein referred to as "FAJ-N0C0"), as well as primers FAJ23STN1-BspHI (SEQ ID NO: 44) and FAJ23STC0-BamHI (SEQ ID NO: 45) for cloning a gene encoding a protein lacking the amino acids of the signal peptide region (herein referred to as "FAJ-N1C0") were designed and synthesized (Table 14).

TABLE 14

| Name | Sequence 5'-3' | Length |
|---|---|---|
| FAJ23STN0-BspHI | TGGATAACTC ATG AAAAACATTATAACAAAAAGAATG (SEQ ID NO: 43) | 37 mer |
| FAJ23STN1-BspHI | TATTATCGTC ATG AACAATGATAACAGCACTACC (SEQ ID NO: 44) | 34 mer |
| FAJ23STC0-BamHI | TCTTTTTAGGATCC TTA AATGTCGCTGATTAGTTTTAT (SEQ ID NO: 45) | 38 mer |

Restriction enzyme sites BspHI (FAJ23STN0-BspHI, FAJ23STN1-BspHI) and BamHI (FAJ23STC0-BamHI), which have been integrated into the cloning primers, are underlined. The translation initiation codon ATG and the complementary sequence TAA corresponding to the translation termination codon are boxed. Moreover, within the primer sequences, sequences annealing to the template DNA are shown in bold type. PCR was carried out using these primers to amplify the α2,3-sialyltransferase gene from the strain JT-FAJ-16 for use in integration into an expression vector. The template DNA used was the above 3.6 kb DNA fragment containing the gene. The reaction conditions for PCR were set as follows. In 50 μl reaction solution containing 300 ng template DNA, 5 μl 10× Ex taq buffer, 4 μl 2.5 mM dNTPs, 50 pmol primer and 0.5 μl Ex taq (Takara Bio Inc., Japan), PCR was carried out using a Program Temp Control System PC-700 (ASTEK) under the following conditions: 96° C. for 3 minutes, (96° C. for 1 minute, 50° C. for 1 minute, 72° C. for 2 minutes)×10 cycles, and 72° C. for 6 minutes. As a result, PCR products of approximately 1.2 kb and 1.1 kb were amplified for FAJ-N0C0 and FAJ-N1C0, respectively. These PCR products were each cloned into a TA cloning vector pCR2.1TOPO (Invitrogen) according to the instructions attached to a TA cloning kit (Invitrogen). The *E. coli* used was TB1. The plasmid was purified from the resulting colonies in a routine manner, and the introduction of each PCR product into the vector was confirmed with a restriction enzyme EcoRI. The plasmid samples confirmed for the introduction were double-digested with restriction enzymes BspHI and BamHI, followed by gel purification to purify a fragment of 1.2 kb (FAJ-N0C0) or 1.1 kb (FAJ-N1C0). Using a Takara Ligation Kit (Takara Bio Inc., Japan), these DNA samples were each ligated to a vector for *E. coli* expression, pTrc99A, which had been double-digested with restriction enzymes NcoI and BamHI. Each vector was integrated into *E. coli* TB1 cells. In a routine manner, the plasmid DNA was extracted and analyzed by restriction enzyme analysis to confirm the integration of the insert. Further, the entire nucleotide sequence was confirmed for one selected clone of FAJ-N0C0 (the first clone of FAJ-N0C0) and two selected clones of FAJ-N1C0 (the first and second clones of FAJ-N1C0). As a result, the first clone of FAJ-N0C0 had no mutation in its nucleotide sequence and comprised a desired nucleotide sequence, i.e., nucleotides 1 to 1209 of SEQ ID NO: 30 in the Sequence Listing. On the other hand, in the case of FAJ-N1C0, its first clone had no mutation in its nucleotide sequence and comprised a desired nucleotide sequence, i.e., nucleotides 67 to 1209 of SEQ ID NO: 30 in the Sequence Listing. The second clone had a nucleotide change from adenine (A) to guanine (G) at position 631 in SEQ ID NO: 30. This resulted in a codon change from ACA to GCA and hence an amino acid change from threonine (Thr) to alanine (Ala). Any other nucleotide replacement was not found in this clone.

(4) Expression Induction and Activity Measurement

In the same manner as shown in Example 5(5), an induction experiment of protein expression was performed on 3 clones, i.e., the first clone of FAJ-N0C0 as well as the first and second clones of FAJ-N1C0 to measure their enzyme activity. As a result, as shown in Table 15 below, sialyltransferase activity was observed in all crude enzyme solutions from the first clone of FAJ-N0C0 as well as the first and second clones of FAJ-N1C0.

TABLE 15

Sialyltransferase activity in *E. coli* homogenate with JT-FAJ-16-derived recombinant homologue of β-galactoside-α2,3-sialyltransferase gene from strain JT-ISH-467

| Crude enzyme solution | Radioactivity (cpm) | | |
|---|---|---|---|
| | Round 1 | Round 2 | Average |
| FAJ-N0C0 first clone | 11012 | 12056 | 11534 |
| FAJ-N1C0 first clone | 5664 | 6724 | 6194 |
| FAJ-N1C0 second clone | 6169 | 6158 | 6163.5 |
| Absence | 232 | 110 | 171 |

(5) Confirmation of α2,3-sialyltransferase Activity

In the same manner as shown in Example 5(6), the first clone of FAJ-N0C0 as well as the first and second clones of FAJ-N1C0 were each introduced into *E. coli* cells to express the encoded enzyme, followed by reaction using pyridylaminated lactose as a glycosyl acceptor to examine the enzyme for its α2,3 sialyltransferase activity. As a result of HPLC analysis on the reaction product of each sialyltransferase expressed by *E. coli* cells, a peak of pyridylaminated α2,3-sialyllactose (pyridylaminated 3'-sialyllactose) was detected for each clone. This result indicated that sialyltransferase from the strain JT-FAJ-16 had α2,3 sialyltransferase activity.

Example 8

Multialignment Analysis on Amino Acid Sequences of Various Sialyltransferase Proteins Genetic information processing software GENETYX Ver. 7 (Genetyx Corporation, Japan) was used for multialignment analysis. As a result, alignment as shown in FIG. 2 was found for α2,3-sialyltransferases from *Photobacterium phosphoreum* strain JT-ISH-467, *Photobacterium* sp. strain JT-ISH-224 and *Vibrio* sp. strain JT-FAJ-16 (SEQ ID NOs: 2, 29 and 31, respectively), α2,6-sialyltransferase (JC5898) from *Photobacterium damselae*, as well as a putative protein PM0188 (AAK02272) of *Pasteurella multocida* subsp. *multocida* strain Pm70. It should be noted that for α2,3-sialyltransferase from the strain JT-ISH-467, underlined regions represent amino acid sequences determined from the purified protein.

Example 9

Optimum pH and Optimum Temperature for Enzyme Activity of (β-galactoside-α2,3-sialyltransferase Purified enzymes were prepared to examine the optimum pH and temperature for β-galactoside-α2,3-sialyltransferase produced by the strain JT-ISH-467 as well as recombinant β-galactoside-α2,3-sialyltransferases produced by the third clone of ISH467-N2C0, the first clone of ISH224-N1C0 and the first clone of FAJ-N1C0.

(1) Optimum pH for Enzyme Activity

Acetate buffer (pH 4.0, pH 4.5 and pH 5.0), cacodylate buffer (pH 5.0, pH 5.5, pH 6.0, pH 6.5 and pH 7.0), phosphate buffer (pH 7.0, pH 7.5 and pH 8.0), TAPS buffer (pH 8.0, pH 8.5 and pH 9.0), CHES buffer (pH 9.0, pH 9.5 and pH 10.0) and CAPS buffer (pH 10.0, pH 10.5 and pH 11.0) were prepared and used for enzyme activity measurement at 25° C. at various pH values.

Figures 1, 2:
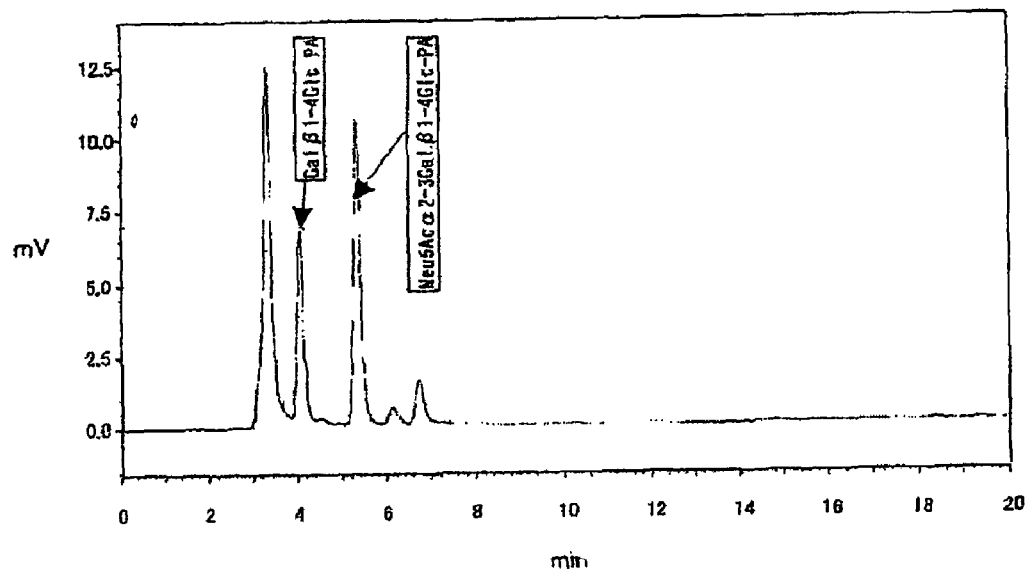
Figures 1, 2, 3:
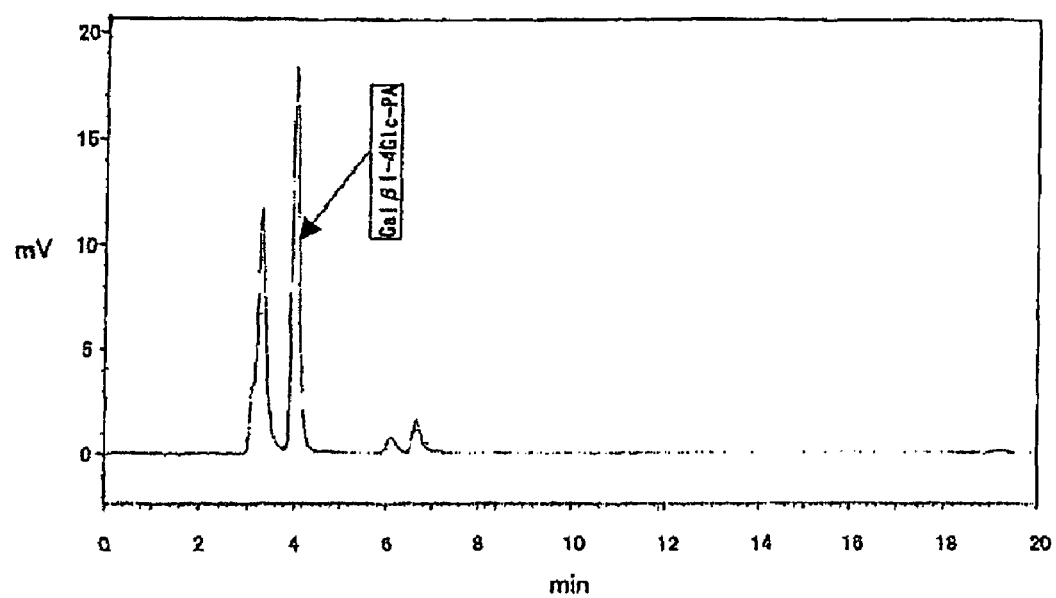
Figures 1, 3:
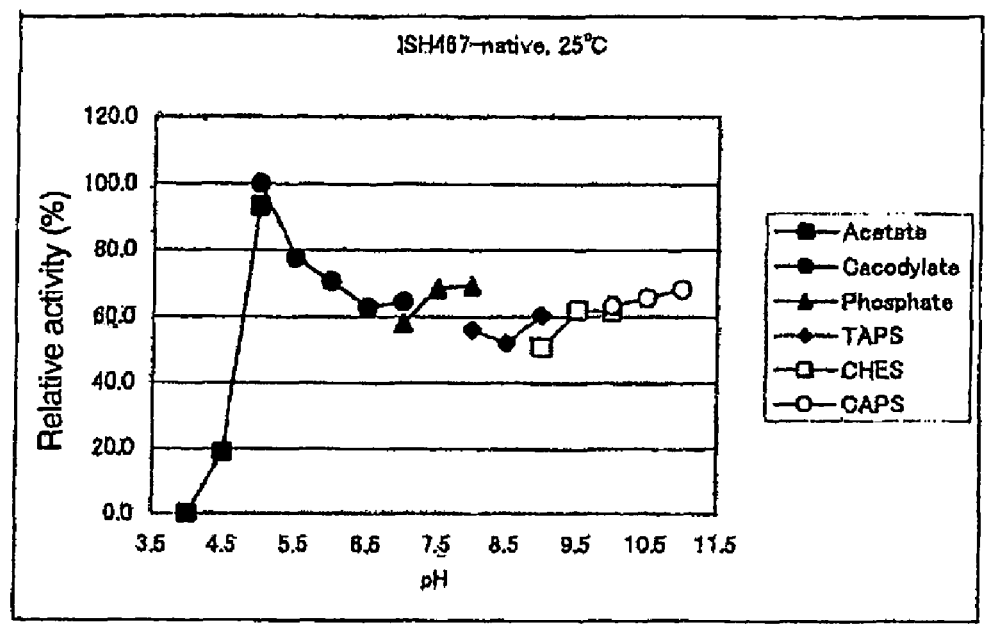
Figures 2, 3:
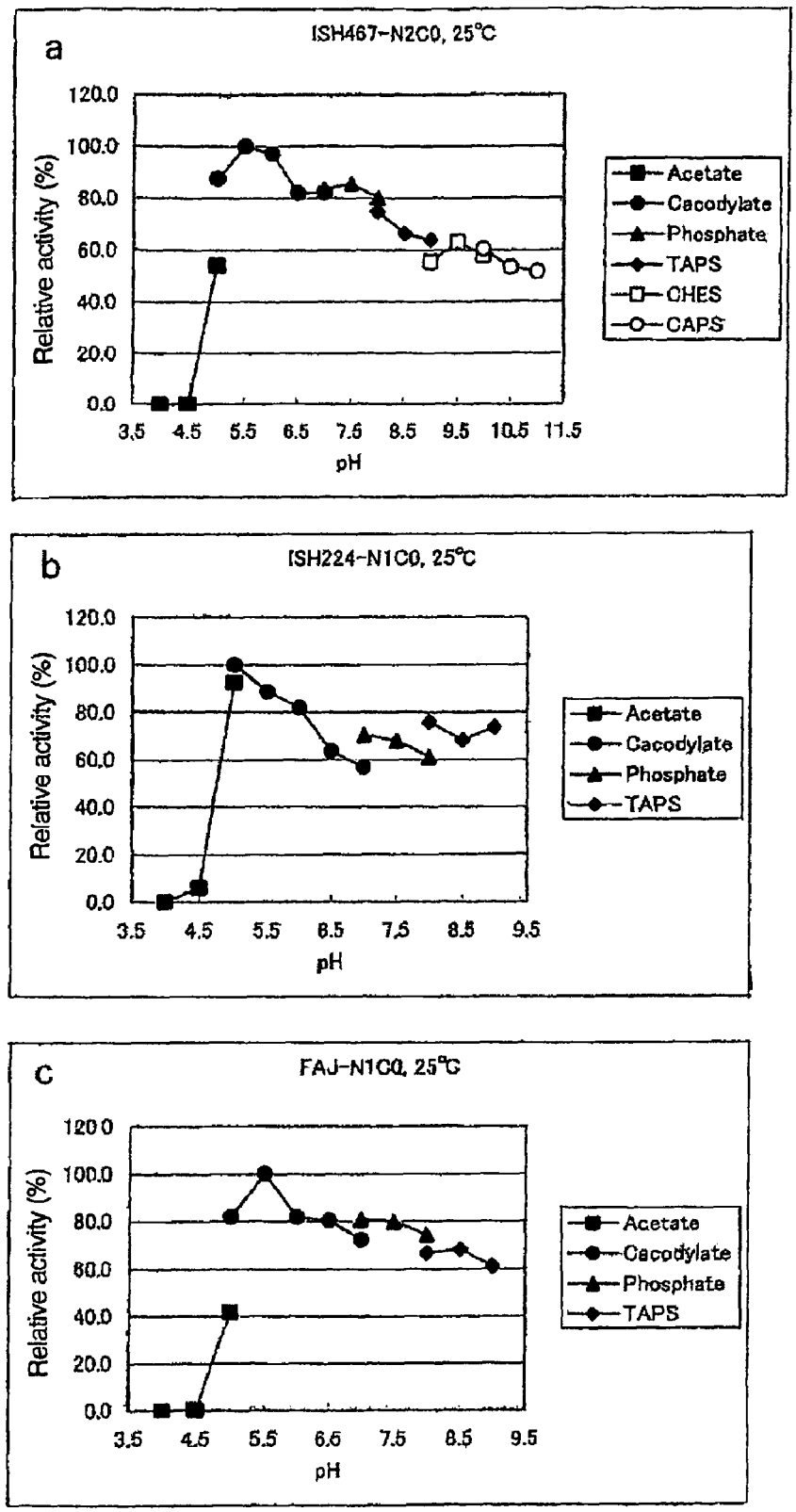

As shown in FIGS. 3-1 and 3-2, the enzyme activity was maximum at pH 5.0 for β-galactoside-α2,3-sialyltransferase produced by the strain JT-ISH-467, at pH 5.5 for the third clone of ISH467-N2C0, at pH 5.0 for the first clone of ISH224-N1C0, and at pH 5.5 for the first clone of FAJ-N1C0. Moreover, all the enzymes showed high activity at pH 5.0 up to pH 7.0 or pH 9.0. It should be noted that enzyme activity at each pH was expressed as relative activity, assuming that the enzyme activity at pH where it reached a maximum was set to 100.

(2) Optimum Temperature for Enzyme Activity

The enzyme activity was measured at an interval of 5° C. starting from 5° C. up to 45° C. and at pH 5.0 for β-galactoside-α2,3-sialyltransferase produced by the strain JT-ISH-467, in cacodylate buffer (pH 5.5) for the third clone of ISH467-N2C0, in cacodylate buffer (pH 5.0) for the first clone of ISH224-N1C0, and in cacodylate buffer (pH 5.5) for the first clone of FAJ-N1C0.

Figures 1, 4:
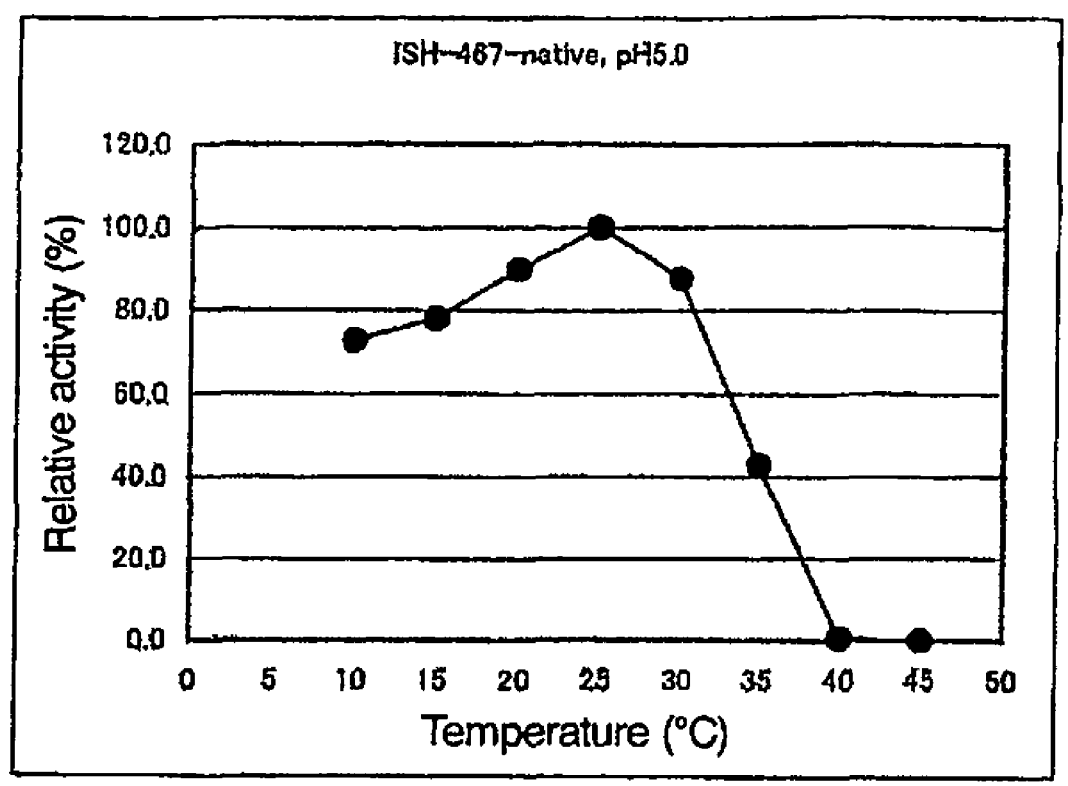
Figures 2, 4:
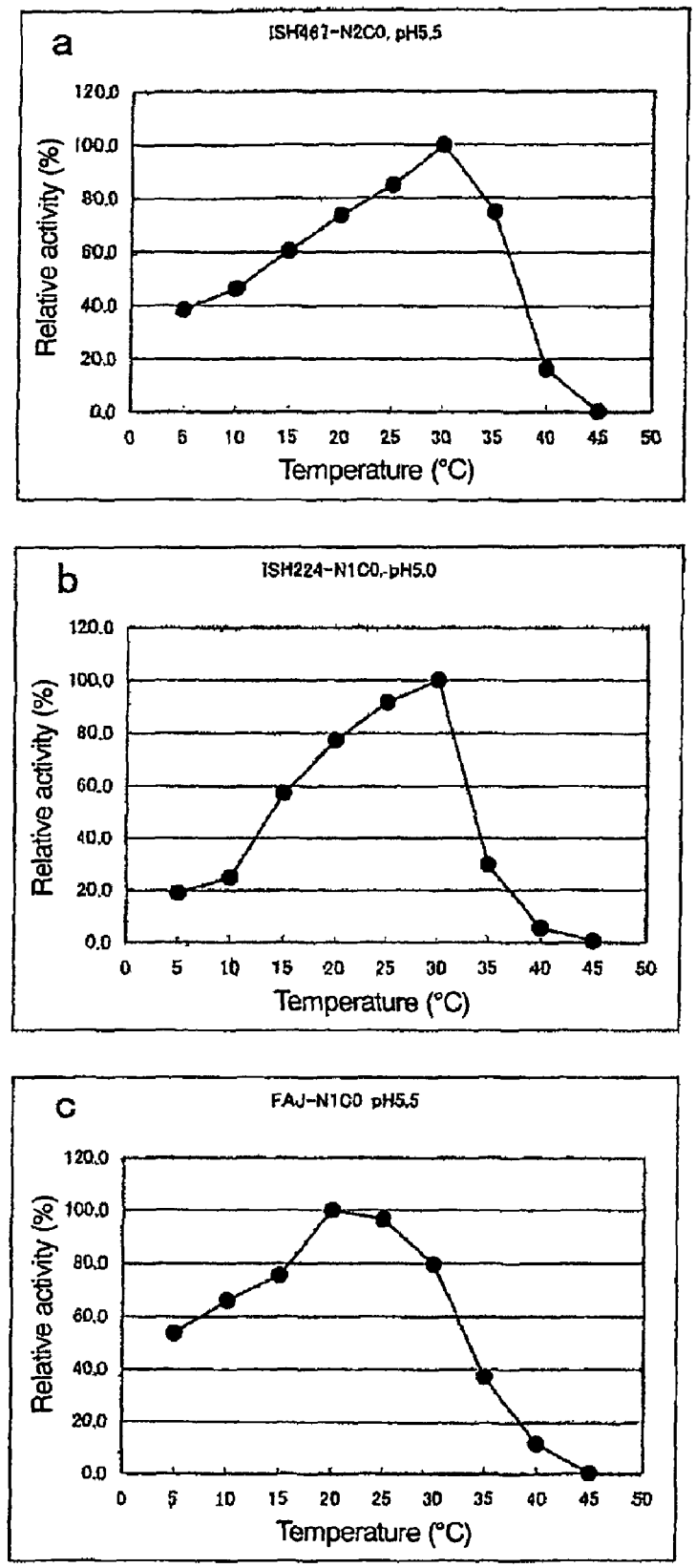

As a result, as shown, in FIGS. 4-1 and 4-2, the enzyme activity was maximum at 25° C. for β-galactoside-α2,3-sialyltransferase produced by the strain JT-ISH-467, at 25° C. for the third clone of ISH467-N2C0, at 30° C. for the first clone of ISH224-N1C0, and at 20° C. for the first clone of FAJ-N1C0. Moreover, all the enzymes showed high activity at 15° C. or 20° C. up to 30° C. or 35° C. It should be noted that enzyme activity at each temperature was expressed as relative activity, assuming at that the enzyme activity at a temperature where it reached a maximum was set to 100.

Example 10

Mass Spectrometry of β-galactoside-α2,3-sialyltransferase

Purified enzymes prepared for β-galactoside-α2,3-sialyltransferase produced by *Photobacterium phosphoreum* strain JT-ISH-467 as well as recombinant β-galactoside-α2,3-sialyltransferases produced by the second clone of ISH467-N0C0, the third clone of ISH467-N2C0, the first clone of ISH224-N1C0 and the first clone of FAJ-N1C0 were analyzed by mass spectrometry with a laser desorption ionization-time of flight/mass spectrometer (MALDI-TOFMS AXIMA-CFR, Shimadzu Corporation, Japan), indicating that they had molecular weights of 45,026 Da, 45,023 Da, 44,075 Da, 43,996 Da and 43,921 Da, respectively.

In the case of the third clone of ISH467-N2C0, the first clone of ISH224-N1C0 and the first clone of FAJ-N1C0, the results of mass spectrometry were in agreement with the molecular weights deduced from their amino acid sequences. However, in the case of β-galactoside-α2,3-sialyltransferase produced by *Photobacterium phosphoreum* strain JT-ISH-467 and the second clone of ISH467-N0C0, the results of mass spectrometry were not in agreement with the molecular weights deduced from their amino acid sequences. This may be because the amino acid sequences of these two enzymes contain a consensus sequence called lipobox (Leu-Gly-Gly-Cys; amino acid residues 19-22 of SEQ ID NO: 2), which caused cleavage at the amino terminus of Cys in this consensus sequence and lipid addition to Cys in the lipobox within bacterial cells (Madan Babu, M. and Sankaran, K., Bioinformatics., 18, 641-643 (2002)).

Example 11

Comparison Of Acceptor Substrate (Monosaccharide, Disaccharide and Trisaccharide) Specificity of Recombinant β-galactoside-α2,3-sialyltransferase (Material and Method)

Cell homogenates prepared from *E. coli* cells introduced with the third clone of ISH467-N2C0, the first clone of ISH224-N1C0 and the first clone of FAJ-N1C0 were each purified by ion exchange chromatography and hydroxyapatite chromatography to give an electrophoretically single band. The thus purified β-galactoside-α2,3-sialyltransferases were used in the following experiment in order to examine the presence or absence of sialyltransferase activity toward various monosaccharides, disaccharides and trisaccharides.

Sialic Acid Transfer Reaction Using Various Glycosyl Acceptor Substrates

A reaction solution (24 μl) was prepared to contain CMP-$^{14}$C-NeuAc-containing CMP-NeuAc as a glycosyl donor substrate (21.9 nmol, final concentration in the reaction solution: 0.874 mM), any of various glycosyl acceptor substrates dissolved in 20 mM cacodylate buffer (pH 5.0) (1 μmol, final concentration in the reaction solution: 42 mM), sialyltransferase (in an amount as indicated in the footnotes of the tables below) and NaCl (final concentration in the reaction solution: 500 mM), and reacted under conditions as indicated in the footnotes of the tables below. The monosaccharides used as glycosyl acceptor substrates were the following 10 types: methyl-α-D-galactopyranoside (Gal-α-OMe), methyl-(β-D-galactopyranoside (Gal-β-OMe), methyl-α-D-glucopyranoside (Glc-α-OMe), methyl-β-D-glucopyranoside (Glc-β-OMe), methyl-α-D-mannopyranoside (Man-α-OMe), methyl-β-D-mannopyranoside (Man-β-OMe), methyl-α-D-fucopyranoside (Fuc-α-OMe), methyl-β-D-fucopyranoside (Fuc-β-OMe), N-acetylgalactosamine (GalNAc), and N-acetylglucosamine (GalNAc). The disaccharides used were the following 5 types: lactose (Gal-β1,4-Glc), N-acetyllactosamine (Gal-β1,4-GlcNAc), methyl-β-D-galactopyranosyl-β1,3-N-acetylglucosaminide (Gal-β1,3-GlcNAc-β-OMe), methyl-α-D-galactopyranosyl-α1,3-galactopyranoside (Gal-α-1,3-Gal-α-OMe), and methyl-β-D-galactopyranosyl-β1,3-galactopyranoside (Gal-β1,3-Gal-β-OMe). The trisaccharide used was 2'-fucosyllactose (Fuc-α1,2-Galβ1,4-Glc). It should be noted that the final concentration was set to 8.4 mM for the sugar chains shown in Table 18, i.e., methyl-α-D-galactopyranosyl-α1,3-galactopyranoside (Gal-α1,3-Gal-α-OMe), methyl-β-D-galactopyranosyl-β1,3-galactopyranoside (Gal-β1,3-Gal-β-OMe) and 2'-fucosyllactose (Fuc-α1,2-Gal-β1,4-Glc).

After completion of the enzymatic reaction, 1.98 ml of 5 mM phosphate buffer (pH 6.8) was added to the reaction solution to stop the enzymatic reaction. Then, the enzymatic reaction solution was diluted with 5 mM phosphate buffer (pH 6.8) and applied in a volume of 2 ml to a AG1–×2 Resin ($PO_4^{3-}$ form, 0.2×2 cm) column. This column was prepared as follows: AG1-x 2 Resin (OH$^-$ form, BIO-RAD) was suspended in 1 M phosphate buffer (pH 6.8), and after 30 minutes, the resin was washed with distilled water and then suspended in distilled water. The eluate (0 to 2 ml) from this column was measured for its radioactivity. The eluate from this column contains the unreacted glycosyl acceptor substrate and the $^{14}$C-NeuAc (N-acetylneuraminic acid)-bound reaction product which was generated by the reaction, but unreacted CMP-14C-NeuAc is still retained on the column. Thus, the radioactivity of $^{14}$C from each sialic acid-containing sugar chain generated as a result of the enzymatic reaction arises exclusively from the reaction product, so that the radioactivity of this fraction can be used to calculate the enzyme activity.

In the manner described above, the radioactivity of NeuAc transferred to each glycosyl acceptor substrate was measured to calculate the amount of transferred sialic acid.

(Results)

Sialic acid was found to be efficiently transferred to all the 16 monosaccharides, disaccharides and trisaccharide used as glycosyl acceptor substrates in this experiment (Tables 16, 17 and 18). It should be noted that the relative activity toward each acceptor substrate was calculated assuming that the sialyltransferase activity toward lactose was set to 100.

TABLE 16

Acceptor substrate specificity (No. 1)

| Acceptor substrate | | ISH467-N2C0 Sialyltransferase activity | | ISH224-N1C0 Sialyltransferase activity | | FAJ-N1C0 Sialyltransferase activity | |
|---|---|---|---|---|---|---|---|
| Name | Structural formula | nmol/min | Relative activity (%) | nmol/min | Relative activity (%) | nmol/min | Relative activity (%) |
| Methylαgalactopyranoside | Galα-OMe | 10.5 | 134 | 9.5 | 113 | 10.3 | 135 |
| Methylβgalactopyranoside | Galβ-OMe | 9.1 | 116 | 8.9 | 105 | 8.7 | 114 |
| Methylαglucopyranoside | Glcα-OMe | 6.2 | 79 | 4.3 | 51 | 4.7 | 62 |
| Methylβglucopyranoside | Glcβ-OMe | 3.6 | 46 | 3.7 | 43 | 4.0 | 52 |
| Methylαmannopyranoside | Manα-OMe | 5.5 | 71 | 4.7 | 56 | 4.3 | 57 |
| N-Acetylgalactosamine | GalNAc | 5.4 | 69 | 5.8 | 69 | 4.4 | 58 |
| N-Acetylglucosamine | GlcNAc | 5.0 | 63 | 5.7 | 68 | 4.2 | 55 |
| Lactose | Galβ1,4-Glc | 7.8 | 100 | 8.4 | 100 | 7.6 | 100 |
| Lactosamine | Galβ1,4-GlcNAc | 9.2 | 118 | 9.7 | 115 | 9.6 | 127 |
| Methylβ-galactopyranosyl-β1,3-N-acetylglucosaminide | Galβ1,3-GlcNAcβ-OMe | 9.6 | 122 | 9.4 | 111 | 9.4 | 124 |

Reaction conditions

Reaction composition:

| | |
|---|---|
| 1 μmol Acceptor substrate (20 mM cacodylate buffer, pH 5.0) | 11.8 μl |
| CMP-$^{14}$C-NeuAc-containing CMP-NeuAc (21.9 nmol (about 20000 cpm)) | 4.8 μl |
| Enzyme solution | 5 μl (about 2.5 mU) |
| 5 M NaCl | 2.4 μl |
| Reaction temperature: | 20° C. |
| Reaction time: | 14 hours |

TABLE 17

Acceptor substrate specificity (No. 2)

| Acceptor substrate | | ISH467-N2C0 Sialyltransferase activity | | ISH224-N1C0 Sialyltransferase activity | |
|---|---|---|---|---|---|
| Name | Structural formula | nmol/min | Relative activity (%) | nmol/min | Relative activity (%) |
| Methylαgalactopyranoside | Galα-OMe | 10.38 | 452 | 8.49 | 823 |
| Methylβgalactopyranoside | Galβ-OMe | 5.77 | 251 | 3.54 | 343 |
| Methylαglucopyranoside | Glcα-OMe | 1.11 | 48 | 0.70 | 68 |
| Methylβglucopyranoside | Glcβ-OMe | 0.76 | 33 | 0.27 | 26 |
| Methylαmannopyranoside | Manα-OMe | 1.38 | 60 | 1.11 | 108 |
| Methylβmannopyranoside | Manβ-OMe | 1.45 | 63 | 1.03 | 100 |
| Methylαfucopyranoside | Fucα-OMe | 1.13 | 49 | 0.70 | 68 |
| Methylβfucopyranoside | Fucβ-OMe | 0.97 | 42 | 0.50 | 48 |
| N-Acetylgalactosamine | GalNAc | 0.99 | 43 | 0.78 | 76 |
| N-Acetylglucosamine | GlcNAc | 0.91 | 40 | 0.51 | 50 |
| Lactose | Galβ1,4-Glc | 2.29 | 100 | 1.03 | 100 |
| Lactosamine | Galβ1,4-GlcNAc | 2.36 | 103 | 0.99 | 96 |
| Methylβ-galactopyranosylβ1,3-N-acetylglucosaminide | Galβ1,3-GlcNAcβ-OMe | 2.95 | 129 | 1.98 | 192 |

Reaction conditions

Reaction composition:

| | |
|---|---|
| 1 μmol Acceptor substrate (20 mM cacodylate buffer, pH 5.0) | 11.8 μl |
| CMP-$^{14}$C-NeuAc-containing CMP-NeuAc (21.9 nmol (about 18500 cpm)) | 4.8 μl |
| Enzyme solution | 5 μl |
| 5 M NaCl | 2.4 μl |
| Reaction temperature: | 30° C. |
| Reaction time: | 0.5 minutes or 2 minutes |
| Enzyme amount: | 2.3 mU per reaction for ISH467-N2C0, 1.0 mU per reaction for ISH224-N1C0 |

TABLE 18

Acceptor substrate specificity (No. 3)

| Acceptor substrate | | ISH467-N2C0 Sialyltransferase activity | | ISH224-N1C0 Sialyltransferase activity | |
| --- | --- | --- | --- | --- | --- |
| | | Relative activity | | Relative activity | |
| Name | Structural formula | nmol/min | (%) | nmol/min | (%) |
| Methylα-galactopyranosylα1,3-galactopyranoside | Galα1,3-Galα-OMe | 7.17 | 308 | 8.80 | 528 |
| Methylβ-galactopyranosylβ1,3-galactopyranoside | Galβ1,3-Galβ-OMe | 5.17 | 222 | 5.52 | 331 |
| 2'-Fucosyllactose | 2'-Fuc-Galβ1,4-Glc | 0.76 | 46 | 0.78 | 52 |
| Lactose | Galβ1,4-Glc | 1.64 | 100 | 1.51 | 100 |

Reaction conditions

Reaction composition:

| | |
| --- | --- |
| 0.2 μmol Acceptor substrate (20 mM cacodylate buffer, pH 5.0) | 11.8 μl |
| CMP-$^{14}$C-NeuAc-containing CMP-NeuAc (21.9 nmol (about 18500 cpm)) | 4.8 μl |
| Enzyme solution | 5 μl |
| 5 M NaCl | 2.4 μl |
| Reaction temperature: | 30° C. |
| Reaction time: | 2 minutes |
| Enzyme amount: | 23 mU per reaction for ISH467-N2C0, 1.0 mU per reaction for ISH224-N1C0 |

Example 12

Acceptor Substrate Specificity of Recombinant β-galactoside-α2,3-sialyltransferase Toward Glycoprotein Cell homogenates prepared from *E. coli* cells introduced with the third clone of ISH467-N2C0, the first clone of ISH224-N1C0 and the first clone of FAJ-N1C0 were each purified by ion exchange chromatography and hydroxyapatite chromatography to give an electrophoretically single band. The thus purified β-galactoside-α2,3-sialyltransferases were used in the following experiment in order to examine the presence or absence of sialyltransferase activity toward glycoproteins.

As a glycosyl acceptor substrate, asialofetuin was used. Asialofetuin (2 mg) was dissolved in 1 ml of 20 mM Bis-tris buffer (pH 6.0) and used as a glycosyl acceptor substrate solution. As a glycosyl donor substrate, CMP-$^{14}$C-NeuAc-containing CMP-NeuAc was used. The glycosyl acceptor substrate solution (40 μl), the glycosyl donor substrate (5 μl, 22.8 nmol (about 19,000 cpm)) and any of the enzyme solutions (5 μl, 10 mU each) were mixed and incubated at 25° C. for 2 hours to cause sialic acid transfer reaction. After completion of the reaction, the reaction solution was gel-filtered by being applied to a Sephadex G-50 Superfine (0.8× 18.0 cm) equilibrated with 0.1 M sodium chloride. A glycoprotein-containing eluate fraction (2-4 ml fraction) from gel filtration was collected and measured for its radioactivity using a liquid scintillation counter to quantify sialic acid transferred to the glycosyl acceptor substrate.

As a result, as shown in Table 19, all the enzymes were found to have the ability to transfer sialic acid to asialofetuin.

TABLE 19

Acceptor substrate specificity (No. 4)

| Enzyme solution | Radioactivity (cpm) |
| --- | --- |
| ISH467-N2C0 | 1729 |
| ISH224-N1C0 | 3301 |
| FAJ-N1C0 | 2865 |
| Absence | 9 |

Reaction conditions

Reaction composition:

| | |
| --- | --- |
| Asialofetuin solution | 10 μl |
| Enzyme solution | 5 μl |
| 5 mM CMP-sialic acid (in 20 mM cacodylate buffer (pH 5)) + $^{14}$C-CMP-sialic acid | 5 μl |

Example 13

Acceptor Substrate Specificity of Recombinant β-galactoside-α2,3-sialyltransferase Toward PA Sugar Chain Cell homogenates prepared from *E. coli* cells introduced with the third clone of ISH467-N2C0, the first clone of ISH224-N1C0 and the first clone of FAJ-N1C0 were each purified by ion exchange chromatography and hydroxyapatite chromatography to give an electrophoretically single band. The thus purified β-galactoside-α2,3-sialyltransferases were used in the following experiment in order to examine the presence or absence of sialyltransferase activity toward PA sugar chains.

In the same manner as described in Example 3, the enzymatic reaction was carried out using, as a glycosyl acceptor, pyridylaminated lactose (Galβ1-4Glc-PA, PA-Sugar Chain 026, Takara Bio Inc., Japan), pyridylaminated GM1-pentasaccharide (Galβ1-3GalNAcβ1-4(Neu5Acα2-3)Galβ1-4Glc-PA, PA-Sugar Chain 032, Takara Bio Inc., Japan) or pyridylaminated GD1b-hexasaccharide (Galβ1-3GalNAcβ1-4(Neu5Acα2-8Neu5Acα2-3)Galβ1-4Glc-PA, PA-Sugar Chain 034, Takara Bio Inc., Japan) under conditions as indicated in the footnote of the table below. After completion of the reaction, the reaction solution was thermally treated at 95° C. for 5 minutes to deactivate the enzyme, followed by HPLC analysis.

As a result, when using PA-Sugar Chain 026 as an acceptor substrate, a peak having the same elution time as PA-Sugar Chain 029 standard was detected for each enzyme. Likewise, when using PA-Sugar Chain 032 as an acceptor substrate, a peak having the same elution time as PA-Sugar Chain 033 standard was detected, while when using PA-Sugar Chain 034 as an acceptor substrate, a peak having the same elution time as PA-Sugar Chain 036 standard was detected. Thus, recombinant β-galactoside-α2,3-sialyltransferases from the strains JT-ISH-467, JT-ISH-224 and JT-FAJ-16 were found to have the ability to transfer sialic acid in α-2,3 linkage to galactose located at the non-reducing end of each tested PA sugar chain.

TABLE 20

Acceptor substrate specificity (No. 5)

| Acceptor substrate | | ISH467-N2C0 Sialyltransferase activity | ISH224-N1C0 Sialyltransferase activity | FAJ-N1C0 Sialyltransferase activity |
|---|---|---|---|---|
| Name | Structural formula | | | |
| PA-Sugar Chain 026 | Galβ1-4Glc-PA | + | + | + |
| PA-Sugar Chain 032 | Galβ1-3GalNAcβ1-4(Neu5Acα2-3)Galβ1-4Glc-PA | + | + | + |
| PA-Sugar Chain 034 | Galβ1-3GalNAcβ1-4(Neu5Acα2-8Neu5Acα2-3)Galβ1-4Glc-PA | + | + | + |

Reaction conditions

Reaction composition:

| | |
|---|---|
| PA sugar chain (10 pmol/μl) | 2.5 μl |
| 5 mM CMP-sialic acid (in 20 mM cacodylate buffer (pH 5)) | 5 μl |
| 3M NaCl | 2.5 μl |
| Enzyme solution | 5 μl (0.1 mU) |

Reaction temperature: 20° C.
Reaction time: 3 hours for ISH467-N2C0, 16 hours for ISH224-N1C0, 24 hours for FAJ-N1C0

Industrial Applicability

By providing a novel f-β-galactoside-α2,3-sialyltransferase and a nucleic acid encoding the same, the present invention provides a means for synthesizing and producing sugar chains which are being shown to have important functions in the body. In particular, sialic acid is often located at the non-reducing ends of complex carbohydrate sugar chains in the body and is a very important sugar in terms of sugar chain functions. Thus, sialyltransferase is one of the most in demand enzymes among glycosyltransferases. The novel sialyltransferase of the present invention can be used for the development of pharmaceuticals, functional foods and other products where sugar chains are applied.

The invention claimed is:

1. An isolated protein comprising an amino acid sequence selected from the group consisting of SEQ ID NO: 2, amino acid residues 22-409 of SEQ ID NO: 2, SEQ ID NO: 29, and amino acid residues 25-409 of SEQ ID NO: 29.

2. An isolated protein having β-galactoside-α2,3-sialyltransferase activity, which comprises an amino acid sequence comprising conservative substitution of one or more amino acids in, and sharing an amino acid homology of at least 90% or more with, an amino acid sequence selected from the group consisting of SEQ ID NO: 2, amino acid residues 22-409 of SEQ ID NO: 2, SEQ ID NO: 29, and amino acid residues 25-409 of SEQ ID NO: 29.

3. An isolated protein having β-galactoside-α2,3-sialyltransferase activity, which comprises an amino acid sequence sharing an amino acid homology of at least 90% or more with an amino acid sequence selected from the group consisting of SEQ ID NO: 2, amino acid residues 22-409 of SEQ ID NO: 2, SEQ ID NO: 29, and amino acid residues 25-409 of SEQ ID NO: 29.

4. An isolated protein having β-galactoside-α2,3-sialyltransferase activity, which is encoded by a nucleic acid comprising a nucleotide sequence selected from the group consisting of SEQ ID NO: 1, nucleotides 64-1230 of SEQ ID NO: 1, SEQ ID NO: 28, and nucleotides 73-1230 of SEQ ID NO: 28.

5. An isolated protein having β-galactoside-α2,3-sialyltransferase activity, which is encoded by a nucleic acid comprising a nucleotide sequence hybridizable under conditions including hybridization at 65° C. in 0.5M sodium phosphate pH 7.2, 1 mM EDTA, 7% SDS, 1% BSA, and washing at 65° C. in 40 mM sodium phosphate buffer pH 7.2, 1 mM EDTA, 5% SDS, 0.5% BSA and at 65° C. in 40 mM sodium phosphate buffer pH 7.2, 1 mM EDTA, 1% SDS with the full length complementary strand of a nucleotide sequence selected from the group consisting of SEQ ID NO: 1 and SEQ ID NO: 28.

6. The isolated protein according to claim 3, which is obtained from a microorganism which belongs to Vibrionaceae.

7. An isolated nucleic acid encoding a protein comprising an amino acid sequence selected from the group consisting of SEQ ID NO: 2, amino acid residues 22-409 of SEQ ID NO: 2, SEQ ID NO: 29, and amino acid residues 25-409 of SEQ ID NO: 29.

8. An isolated nucleic acid encoding a protein having β-galactoside-α2,3-sialyltransferase activity, wherein the protein comprises an amino acid sequence comprising conservative substitution of one or more amino acids in, and sharing an amino acid homology of at least 90% or more with, an amino acid sequence selected from the group consisting of SEQ ID NO: 2, amino acid residues 22-409 of SEQ ID NO: 2, SEQ ID NO: 29, and amino acid residues 25-409 of SEQ ID NO: 29.

9. An isolated nucleic acid encoding a protein having β-galactoside-α2,3-sialyltransferase activity, wherein the protein comprises an amino acid sequence sharing a homology of at least 90% with an amino acid sequence selected from the group consisting of SEQ ID NO: 2, amino acid residues 22-409 of SEQ ID NO: 2, SEQ ID NO: 29, and amino acid residues 25-409 of SEQ ID NO: 29.

10. An isolated nucleic acid comprising a nucleotide sequence selected from the group consisting of SEQ ID NO: 1, nucleotides 64-1230 of SEQ ID NO: 1, SEQ ID NO: 28, and nucleotides 73-1230 of SEQ ID NO: 28.

11. An isolated nucleic acid encoding a protein having β-galactoside-α2,3-sialyltransferase activity, wherein the nucleic acid comprises a nucleotide sequence hybridizable under conditions including hybridization at 65° C. in 0.5M sodium phosphate pH 7.2, 1 mM EDTA, 7% SDS, 1% BSA, and washing at 65° C. in 40 mM sodium phosphate buffer pH 7.2, 1 mM EDTA, 5% SDS, 0.5% BSA and at 65° C. in 40 mM sodium phosphate buffer pH 7.2, 1 mM EDTA, 1% SDS, with the full length complementary strand of a nucleotide sequence selected from the group consisting of SEQ ID NO: 1 and SEQ ID NO: 28.

12. A recombinant vector comprising the nucleic acid according to claim 9.

13. An isolated host cell transformed with the recombinant vector according to claim 12.

14. An isolated microorganism of the Vibrionaceae, which expresses the protein according to claim 1.

15. The microorganism according to claim 14, which is *Photobacterium phosphoreum* strain JT-ISH-467 (Accession No. NITE BP-88), or *Photobacterium* sp. strain JT-ISH-224 (Accession No. NITE BP-87).

16. A method for producing a recombinant protein having β-galactoside-α2,3-sialyltransferase activity, which comprises the following steps:
   1) transforming and isolating a host cell with a recombinant vector comprising the nucleic acid according to claim 7;
   2) culturing the transformed host cell; and
   3) isolating the protein having β-galactoside-α2,3-sialyltransferase activity from the cultured host cell or the culture supernatant.

17. A method for preparing a sialylated sugar chain, which comprises:
   (i) preparing a solution containing the protein according to claim 1, a glycosyl donor substrate and a glycosyl acceptor substrate;
   (ii) causing sialic acid transfer reaction in the solution; and
   (iii) obtaining the generated sialylated sugar chain from the reaction solution.

18. The isolated protein of claim 1, which comprises SEQ ID NO: 2.

19. The method of claim 16, wherein said nucleic acid encodes a protein comprising SEQ ID NO: 2.

* * * * *